US008163892B2

(12) United States Patent
Fujiwara et al.

(10) Patent No.: US 8,163,892 B2
(45) Date of Patent: Apr. 24, 2012

(54) ONCOLYTIC VIRUS REPLICATING SELECTIVELY IN TUMOR CELLS

(75) Inventors: Toshiyoshi Fujiwara, Okayama (JP); Noriaki Tanaka, Tottori (JP); Satoru Kyo, Ishikawa (JP); Yoshiko Shirakiya, Okayama (JP); Takeshi Kawashima, Okayama (JP)

(73) Assignee: Oncolys Biopharma, Inc., Tokyo (JP)

( * ) Notice: Subject to any disclaimer, the term of this patent is extended or adjusted under 35 U.S.C. 154(b) by 0 days.

(21) Appl. No.: 12/839,264

(22) Filed: Jul. 19, 2010

(65) Prior Publication Data

US 2011/0044949 A1 Feb. 24, 2011

Related U.S. Application Data

(63) Continuation-in-part of application No. 10/520,901, filed as application No. PCT/JP03/08573 on Jul. 7, 2003, now abandoned.

(30) Foreign Application Priority Data

Jul. 8, 2002 (JP) ................................ 2002-198941

(51) Int. Cl.
*C07H 21/02* (2006.01)
*C07H 21/04* (2006.01)
*C12N 15/00* (2006.01)
*A61K 48/00* (2006.01)

(52) U.S. Cl. .................. 536/23.1; 435/320.1; 514/44 R

(58) Field of Classification Search ................ 536/23.1; 435/320.1; 514/44 R
See application file for complete search history.

(56) References Cited

U.S. PATENT DOCUMENTS 6,692,736 B2 2/2004 Yu et al.
2003/0104625 A1 6/2003 Cheng et al.
2005/0048466 A1 3/2005 Qian et al.
2005/0214923 A1* 9/2005 Yu et al. ..................... 435/235.1
2006/0029596 A1* 2/2006 Wold et al. ................. 424/130.1
2007/0099933 A1 5/2007 Heinrich et al.

FOREIGN PATENT DOCUMENTS

WO WO9933998 A3 8/1999
WO WO0042208 A1 7/2000
WO WO0046355 A2 8/2000
WO WO0040741 A9 10/2001
WO WO0220754 A2 3/2002
WO WO0173093 A3 9/2002

OTHER PUBLICATIONS

Bisland et al., Modulation of telomerase promoter tumor selectivity in the context of oncolytic adenoviruses, Cancer Res. 67(3):1299-307, 2007.*

Kyo et al., Understanding and exploiting hTERT promoter regulation for diagnosis and treatment of human cancers, Cancer Sci. 99(8):1528-38, 2008.*

Dobson, Gene therapy progress and prospects: magnetic nanoparticle-based gene delivery. Gene Ther. 13(4): 283-7 (2006).

Fujiwara et al., Phase 1 Trial of Intratumoral Administration of OBP-301, A Novel Telomerase-Specific Oncolytic Virus, in Patients with Advanced Solid Cancer: Evaluation of Biodistribution and Immune Response, Gene & Cell Therapy (1 page).

Hiyama et al., “Immunohistochemical detection of telomerase (hTERT) protein in human cancer tissues and a subset of cells in normal tissues, ” NEOPLASIA (New York, NY) 3(1):17-26 (2001).

Holt et al., “Role of telomerase in cellular proliferation and cancer”, J. of Cellular Phys., LISS, New York, NY, U.S.A., 180(1)10-18 (1999).

Johnson-Saliba et al. Gene therapy: optimizing DNA delivery to the nucleus. Curr Drug Targets. 2(4): 371-99 (2001).

Kim et al., “Antitumoral effects of recombinant adenovirus YKL-1001, conditionally replicating in α-fetoprotein-producing human liver cancer cells”, Cancer Letters, 180:23-32 (2002).

Komata et al., “Caspase-8 Gene Therapy Using the Human Telomerase Reverse Transcriptase Promoter for Malignant Glioma Cells”, Human Gene Therapy, 13:1015-1025 (2002).

Kurihara et al., “Selectivity of a replication-competent adenovirus for human breast carcinoma cells expressing the MUCI antigen”, The J. of Clin. Investigation 106(6):763-771, (2000).

Li et al., “A hepatocellular carcinoma-specific adenovirus variant, CV890, eliminates distant human liver tumers in combination with doxorubicin”, Cancer Res., American Assoc. for Cancer Res., Baltimore, MD, U.S.A., 61 (17):6428-6436 (2001).

Nemunaitis et al., “A Phase 1 Study of Telomerase-specific Replication Competent Oncolytic Adenovirus (Telomelysin) for Various Solid Tumors”, The American Society of Gene & Cell Therapy, Molecular Therapy (2010) 18(2): 429-434—online publication Nov. 24, 2009.

Pouton and Seymour, Key issues in non-viral gene delivery, Adv Drug Deliv Rev. 46(1-3): 187-203, (2001).

Read et al., Barriers to gene delivery using synthetic vectors, Adv Genet. 53: 19-46 (2005).

Rodriquez et al., “Prostate Attenuated Replication Competent Adenovirus (ARCA) CN706:A Selective Cytotoxic for Prostate-specific Antigen-positive Prostate Cancel Cells”, Cancer Res. 57:2559-2563 (1997).

Zhang et al., “Identification of Human Ureoplakin II Promoter and Its Use in the Construction of CG8840, a Urothelium-specific Andenovirus Variant That Eliminates Established Bladder Tumors in Combination with Docetaxel”, Cancer Res., 62:3743-3750 (2002).

* cited by examiner

*Primary Examiner* — Wu-Cheng Winston Shen
(74) *Attorney, Agent, or Firm* — Fish & Richardson P.C.

(57) ABSTRACT

By using a virus having a gene sequence comprising a telomerase promoter and an E1 gene (preferably a sequence comprising E1A gene, IRES sequence and E1B gene) or by using an anticancer agent comprising the virus, the virus replicates in cancer cells to thereby produce an efficient anticancer effect.

5 Claims, 10 Drawing Sheets

ONCOLYTIC VIRUS REPLICATING SELECTIVELY IN TUMOR CELLS

This application is a continuation-in-part application of U.S. application Ser. No. 10/520,901, which is the U.S. National Phase under 35 U.S.C. §371 of International Patent Application No. PCT/JP2003/008573, filed Jul. 7, 2003, and claims the benefit of priority under 35 U.S.C. §119(a)-(d) of JP application 2002-198941 filed on Jul. 8, 2002. Each of the aforementioned applications is hereby incorporated by reference in its entirety.

REFERENCE TO SEQUENCE LISTING

Pursuant to 37 C.F.R. 1.821(c), a sequence listing is submitted herewith as an ASCII compliant text file named "Sequence Listing.txt" that was created on Jul. 19, 2010 and has a size of 106,772 bytes. The content of the aforementioned file named "Sequence listing.txt" is hereby incorporated by reference in its entirety.

TECHNICAL FIELD

The present invention relates to a virus showing antitumor effect by replicating in tumor cells; a polynucleotide contained in the virus; an anticancer agent comprising the virus; and a method of treating cancers using the virus.

BACKGROUND ART

At present, gene therapy is performed as one method for treating cancers. However, since a gene is introduced into diseased tissue or the like with a non-replication competent virus vector in gene therapy, the gene can be applied to only those regions around target cells taking into consideration the safety of the human body. Also, in the gene therapy currently practiced, satisfactory therapeutic effect cannot be achieved because of low efficiency in gene transfer.

It is known that telomerase activity is often enhanced in malignantly transformed cells or immortalized cell strains, whereas telomerase activity is hardly detected in normal somatic cells excluding such as germ line cells, blood lineage cells and epithelial stem cells.

Under circumstances, it is a major object of the present invention to let a virus grow in tumor cells by utilizing the telomerase activated therein to thereby bring death to the tumor cells efficiently.

DISCLOSURE OF THE INVENTION

Figure 1:
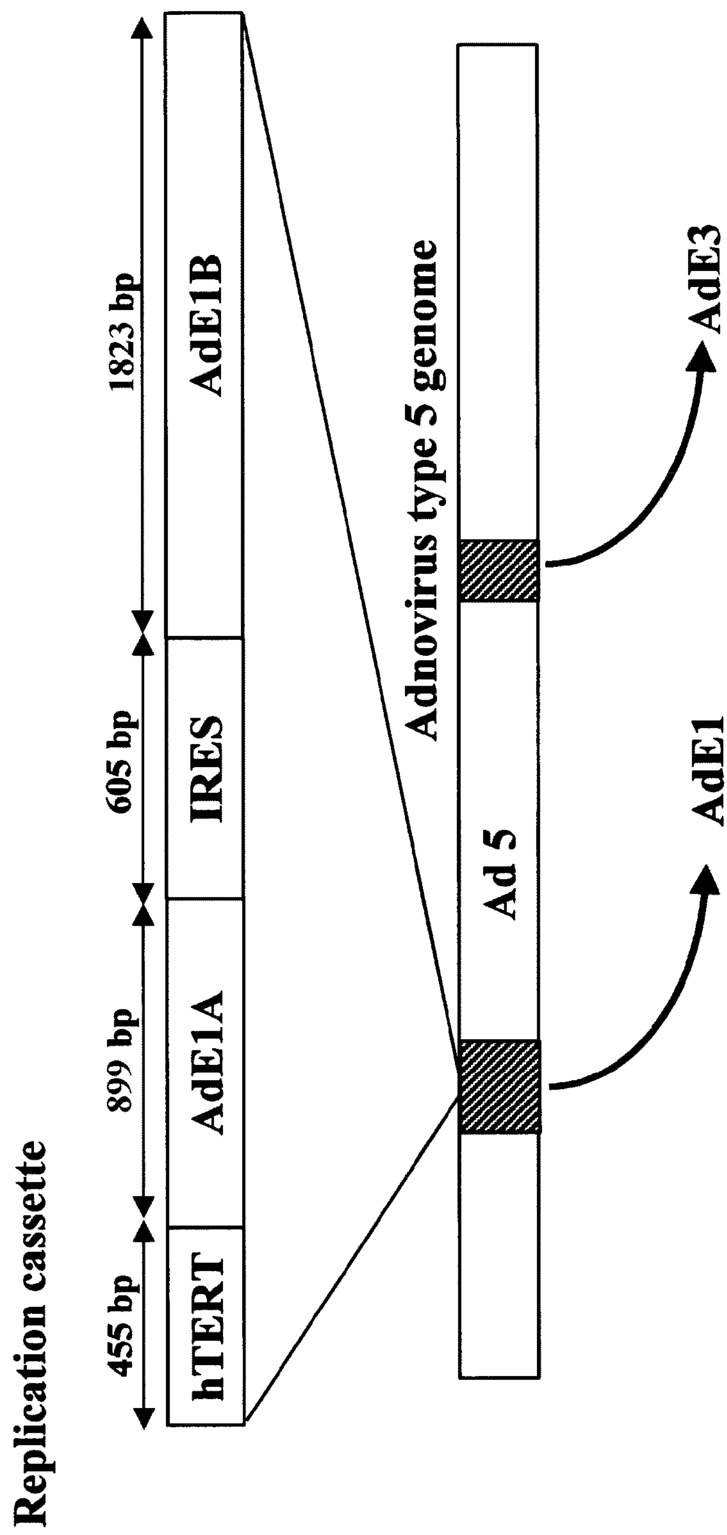
FIG. 1 shows a schematic drawing of the structure of a oncolytic virus replicating selectively in tumor cells. A replication cassette consisting of hTERT promoter, E1A gene, IRES sequence and E1B gene is inserted in the E1 gene region which non-replication competent virus vectors lack.

The present inventors have found for the first time that, by infecting cancer cells with a virus having a telomerase promoter and replication ability, it is possible to let the virus replicate in the cancer cells and bring death to them. Thus, the present invention has been achieved.

The present invention relates to the following items 1 to 11.

1. A polynucleotide cassette comprising an hTERT promoter operably linked with an E1A gene, an IRES sequence and an E1B gene in this order.
2. The polynucleotide cassette according to item 1 above, wherein the E1A gene comprises a nucleotide sequence selected from the group consisting of:

a) the nucleotide sequence of SEQ ID NO: 1; and
b) a nucleotide sequence having at least 90% identity to the nucleotide sequence of SEQ ID NO: 1, wherein the nucleotide sequence encodes a polypeptide having an E1A activity.

3. The polynucleotide cassette according to item 1 above, wherein the E1B gene comprises a nucleotide sequence selected from the group consisting of:

a) the nucleotide sequence of SEQ ID NO: 2 or 9; and
b) a nucleotide sequence having at least 90% identity to the nucleotide sequence of SEQ ID NO: 2 or 9, wherein the nucleotide sequence encodes a polypeptide having an E1B activity.

4. The polynucleotide cassette according to item 1 above, wherein the IRES sequence comprises a nucleotide sequence selected from the group consisting of:

a) the nucleotide sequence of SEQ ID NO: 3 or 10; and
b) a nucleotide sequence having at least 90% identity to the nucleotide sequence of SEQ ID NO: 3 or 10, wherein the nucleotide sequence has an IRES activity.

5. The polynucleotide cassette according to item 1 above, wherein the hTERT promoter comprises a nucleotide sequence selected from the group consisting of:

a) the nucleotide sequence of SEQ ID NO: 4; and
b) a nucleotide sequence having at least 90% identity to the nucleotide sequence of SEQ ID NO: 4, wherein the nucleotide sequence has an hTERT promoter activity.

6. The polynucleotide cassette according to item 1 above, comprising a nucleotide sequence selected from the group consisting of:

a) the nucleotide sequence of SEQ ID NO: 11 or 12; and
b) a nucleotide sequence having at least 90% identity to the nucleotide sequence of SEQ ID NO:11 or 12, wherein the nucleotide sequence encodes a polypeptide having an activity to enable an adenovirus to replicate selectively in tumor cells.

7. A recombinant adenovirus comprising the polynucleotide cassette according to any one of items 1 to 6 above.
8. The recombinant adenovirus according to item 7 above, comprising a nucleotide sequence selected from the group consisting of:
a) the nucleotide sequence of SEQ ID NO: 13; and
b) a nucleotide sequence having at least 90% identity to the nucleotide sequence of SEQ ID NO:13, wherein the nucleotide sequence encodes a polypeptide having an activity to enable an adenovirus to replicate selectively in tumor cells.
9. The recombinant adenovirus according to item 7 above, comprising a nucleotide sequence selected from the group consisting of:
a) the nucleotide sequence of SEQ ID NO: 14; and
b) a nucleotide sequence having at least 90% identity to the nucleotide sequence of SEQ ID NO:14, wherein the nucleotide sequence encodes a recombinant adenovirus having an activity to replicate selectively in tumor cells.
10. A method of treating a cancer comprising administering an effective amount of the recombinant adenovirus according to any one of items 7 to 9 above to a patient in need thereof.
11. The method according to item 10, wherein the cancer is at least one cancer selected from the group consisting of stomach cancer, large bowel cancer, lung cancer, liver cancer, prostate cancer, pancreas cancer, esophagus cancer, bladder cancer, gallbladder/bile duct cancer, breast cancer, uterine cancer, thyroid cancer and ovarian cancer, osteosarcoma and brain tumor.

DETAILED DESCRIPTION OF THE INVENTION

The present invention is characterized by bringing death to cancer cells by infecting cancer cells with a virus having a telomerase promoter and replication ability and letting the virus grow in the cancer cells, based on the finding that a wide variety of cancer cells have telomerase activity.

The virus used in the present invention is not particularly limited. From the viewpoint of safety, adenovirus is preferable. Among adenovirus species, type 5 adenovirus is particularly preferable from the viewpoint of, for example, easiness in use.

E1 gene contained in viral polynucleotide refers to one of early genes of viruses. Viruses have early (E) genes and late (L) genes involved in their DNA replication. E1 gene encodes a protein involved in the regulation of transcription of viral genome.

The E1 gene used in the present invention may be derived from any virus. Preferably, an adenovirus-derived E1 gene is used.

It is known that E1 gene is composed of E1A, E1B and other elements. E1A protein encoded by E1A gene activates the transcription of a group of genes (E1B, E2, E4, etc.) necessary for the production of infectious virus.

In a preferred embodiment of the invention, the E1A gene comprises the nucleotide sequence of SEQ ID NO: 1 or a variant thereof. The variant of E1A comprises the nucleotide sequence having at least 90%, preferably at least 95%, more preferably at least 96%, and even more preferably at least 97%, 98%, or 99% identity to that of SEQ ID NO: 1, wherein the nucleotide sequence encodes a polypeptide having an E1A activity.

Identity of any two nucleotide sequences can be determined by those skilled in the art based, for example, on a BLAST 2.0 computer alignment. BLAST 2.0 searching is known in the art and is publicly available, for example, at ncbi.nlm.nih.gov/BLAST/.

E1B protein encoded by E1 B gene assists the accumulation of late gene (L gene) mRNA in the cytoplasm of the infected host cell to thereby inhibit the protein synthesis in the host cell. Thus, E1B protein promotes viral replication.

In a preferred embodiment of the invention, the E1B gene comprises the nucleotide sequence of SEQ ID NO: 2 or 9. In another preferred embodiment of the invention, the E1B gene comprises a variant of the nucleotide sequence of SEQ ID NO: 2 or 9. The variant of E1B comprises the nucleotide sequence having at least 90%, preferably at least 95%, more preferably at least 96%, and even more preferably at least 97%, 98%, or 99% identity to that of SEQ ID NO: 2 or 9, wherein the nucleotide sequence encodes a polypeptide having an E1B activity. The identity between the nucleotide sequences of SEQ ID NO: 2 and SEQ ID NO: 9 is about 99%.

In the present invention, a known E1 gene may be used as it is. Preferably, an E1 gene having an E1A gene, an IRES sequence and an E1B gene in this order (i.e., an E1 gene in which an IRES sequence is inserted between its E1A gene and E1B gene) is used. With the use of such an E1 gene, the replication ability of the virus of the invention will be high when a host cell has been infected with the virus.

As long as the effect of the invention can be achieved, at least one nucleotide may be inserted into at least one site selected from the group consisting of (a) between IRES sequence and E1A gene, (b) between IRES sequence and E1B gene, (c) upstream of E1A gene, and (d) downstream of E1B gene. As long as the effect of the invention can be achieved, at least one, preferably several nucleotides may be substituted, deleted, inserted or added in the E1A gene, IRES sequence, E1B gene or E1 gene.

"IRES sequence" is a protein synthesis initiation signal specific to picornavirus. It is believed that this sequence serves as a ribosome-binding site because it contains a complementary sequence to the 3' terminal sequence of 18S ribosomal RNA. It is known that picornavirus-derived mRNA is translated via this sequence.

Translation efficiency from IRES sequence is high. Even from the middle of mRNA, protein synthesis is performed in a cap structure non-dependent manner. Therefore, in the virus of the present invention, both E1A gene and E1B gene located downstream of the IRES sequence are translated independently by a promoter from human telomerase.

In a preferred embodiment of the invention, the IRES sequence comprises the nucleotide sequence of SEQ ID NO: 3 or 10. In another preferred embodiment of the invention, the IRES sequence comprises a variant of the nucleotide sequence of SEQ ID NO: 3 or 10. The variant of the IRES sequence comprises the nucleotide sequence having at least 90%, preferably at least 95%, more preferably at least 96%, and even more preferably at least 97%, 98%, or 99% identity to that of SEQ ID NO: 3 or 10, wherein the nucleotide sequence has an IRES activity. The identity between the nucleotide sequences of SEQ ID NO:3 and SEQ ID NO: 10 is about 97%.

In the present invention, it is preferable that E1 gene has a promoter from human telomerase upstream thereof, because such a promoter is capable of promoting the replication of the virus of the invention in cancer cells having telomerase activity. The promoter from human telomerase is not particularly limited as long as the promoter is derived from human. Among all, hTERT promoter is preferable.

hTERT is a gene encoding human telomerase reverse transcriptase. A number of transcription factor-binding sequences are confirmed in a 1.4 kbp region upstream of the 5' end of this gene. This region is believed to be hTERT promoter. In particular, a 181 bp sequence located upstream of the translation initiation site is a core region important for the expression of the downstream gene.

In the present invention, any sequence comprising this core region may be used as a promoter from human telomerase. Preferably, an upstream sequence of approximately 378 bp containing the core region completely is used. It has been confirmed that this sequence of approximately 378 bp is equivalent to the 181 bp core region alone in gene expression efficiency.

In a preferred embodiment of the invention, the hTERT promoter comprises the nucleotide sequence of SEQ ID NO: 4 or a variant thereof. The variant of the hTERT promoter comprises the nucleotide sequence having at least 90%, preferably at least 95%, more preferably at least 96%, and even more preferably at least 97%, 98%, or 99% identity to that of SEQ ID NO: 4, wherein the nucleotide sequence has an hTERT promoter activity.

A gene having the telomerase promoter of the invention and the E1 gene of the invention (a gene comprising E1A gene, IRES gene and E1B gene) may be obtained by conventional genetic engineering techniques.

As the E1 gene, an E1 gene from a known virus having that gene may be used. Preferably, an E1 gene derived from adenovirus is used.

Alternatively, E1A gene and E1B gene may be amplified from E1 gene-expressing cells (preferably, E1 gene-expressing 293 cells or the like) by RT-PCR and/or DNA-PCR using primers such as E1A-S, E1A-AS, E1B-S and E1B-AS. If necessary, their sequences are confirmed using a conventional method such as TA cloning. Then, E1A and E1B DNA fragments may be cut out using a known restriction enzyme such as EcoRI.

E1A and E1B may be inserted into a known vector such as pIRES by conventional genetic engineering techniques to thereby prepare E1A-IRES-E1B sequence within the vector. Subsequently, hTERT promoter sequence which was cut out with restriction enzymes such as MluI and BglII may be inserted into the XhoI site or the like located upstream of E1A. As a result, a polynucleotide cassette comprising an hTERT promoter operably linked with an E1A gene, an IRES sequence and an E1B gene in this order can be obtained.

In a preferred embodiment of the invention, hTERT promoter and E1A gene, E1A and IRES sequence, IRES sequence and E1B gene may be linked by spacer sequences. It is known that, there are many cases in which the shorter the spacer sequences are, the higher the translation efficiency of genes is. Meanwhile, the longer the spacer sequences are, the more the number of restriction enzyme sites that can be utilized is, and therefore, a vector can be easily constructed. In view of these matters, length of the spacer sequence is, preferably 0 to about 100 base pair, more preferably 0 to about 50 base pair, even more preferably 0 to about 35 base pair. Example sequence of spacer is a nucleotide sequence shown in SEQ ID NO: 27, 28 or 29. It is difficult for one of skill in the art that hTERT promoter and E1A gene, E1A and IRES sequence, IRES sequence and E1B gene is linked by such short spacer sequences and the recombinant virus of the invention is constructed.

In another preferred embodiment of the invention, the polynucleotide cassette comprises the nucleotide sequence of SEQ ID NO: 11 or 12 or a variant thereof. The variant of the polynucleotide cassette comprises the nucleotide sequence having at least 90%, preferably at least 95%, more preferably at least 96%, and even more preferably at least 97%, 98%, or 99% identity to that of SEQ ID NO: 11 or 12, wherein the nucleotide sequence encodes a polypeptide having an activity to enable an adenovirus to replicate selectively in tumor cells. The activity can be determined by infecting the adenovirus to tumor cells and measuring viral titer of the adenovirus (see e.g., Example 4 of the present specification).

If necessary, cytomegalovirus (CMV) promoter contained in a known vector such as pShuttle may be removed with restriction enzymes such as MfeI and NheI; then, a sequence cut out from phTERT-E1A-IRES-E1B with restriction enzymes NheI and NotI may be inserted into the site (resultant vector is designated "pSh-hAIB").

From the resultant pSh-hAIB, a sequence comprising necessary portions (including hTERT promoter, E1A gene, IRES sequence and E1B gene) may be cut out with restriction enzymes such as I-CeuI and PI-SceI, and then inserted into a viral DNA such as Adeno-X Viral DNA using a commercial kit such as Adeno-X Expression System (Clontech) (the resultant DNA is designated "AdenoX-hAIB").

The above-described sequence comprising hTERT promoter, E1A gene, IRES sequence and E1B gene may be inserted into any site of a viral gene as long as the effect of the present invention can be achieved. For example, in adenovirus for gene therapy from which E1 gene has been deleted, the above-described sequence is preferably inserted into the deleted site.

It is possible to linearize AdenoX-hAIB with a known restriction enzyme such as PacI and then transfect into cultured cells such as 293 cells, to thereby prepare a infectious recombinant adenovirus (the resultant virus is sometimes called the "virus of the present invention" or "TRAD"). The method of transfection is not particularly limited. From the viewpoint of efficiency, such methods as the calcium phosphate method or electroporation may be preferable.

In a preferred embodiment, the nucleotide sequence of the recombinant adenovirus comprises the above-described polynucleotide cassette comprising the nucleotide sequence of SEQ ID NO: 11 or 12 or a variant thereof. In another preferred embodiment, the nucleotide sequence of the recombinant adenovirus comprises that of SEQ ID NO: 13 or a variant thereof. The variant comprises the nucleotide sequence having at least 90%, preferably at least 95%, more preferably at least 96%, and even more preferably at least 97%, 98%, or 99% identity to that of SEQ ID NO: 13, wherein the nucleotide sequence encodes a polypeptide having an activity to enable an adenovirus to replicate selectively in tumor cells. The activity can be determined by infecting the adenovirus to tumor cells and measuring viral titer of the adenovirus (see e.g., Example 4 of the present specification). The nucleotide sequence of SEQ ID NO: 13 is the nucleotide sequence from the first position of the genome of the recombinant adenovirus to the position just before the first position of the E3 region thereof.

In another preferred embodiment, the nucleotide sequence of the recombinant adenovirus can be that of SEQ ID NO: 14 or a variant thereof. The variant can be the nucleotide sequence having at least 90%, preferably at least 95%, more preferably at least 96%, and even more preferably at least 97%, 98%, or 99% identity to that of SEQ ID NO: 14, wherein the nucleotide sequence encodes a recombinant adenovirus having an activity to replicate selectively in tumor cells. The activity can be determined by infecting the adenovirus to tumor cells and measuring viral titer of the adenovirus (see e.g., Example 4 of the present specification).

The thus obtained virus of the present invention can be replicated by conventional methods for viral replication, e.g. infecting host cells such as 293 cells with the virus.

The virus of the present invention may be used as an anticancer agent. This anticancer agent may be used not only for treating cancers but also for preventing postoperative relapse of cancers, preventing cancer metastasis and/or for prophylaxis of cancers.

The kinds of cancers to which the anticancer agent of the invention is applied are not particularly limited. The anticancer agent is applicable to any kind of cancer. For example, the anticancer agent is effective for cancers in the stomach, large bowel, lung, liver, prostate, pancreas, esophagus, bladder, gallbladder/bile duct, breast, uterus, thyroid, ovary, etc. as well as brain tumor and osteosarcoma. Among all, the anticancer agent is especially effective for solid tumor.

The anticancer agent of the invention may be applied to diseased sites as it is. Alternatively, the anticancer agent may be introduced into humans (target cells or organs) by any known method, e.g. intravenous, intramuscular, intraperitoneal or subcutaneous injection; inhalation through the nasal cavity, oral cavity or lung; oral administration; administration in the form of suppository; and administration in the form of external medicine.

The virus of the invention may be treated, for example, by the lyophilization method to enable easy handling and then used alone, or prepared into pharmaceutical compositions by mixing with known pharmaceutically acceptable carriers such as excipients, fillers, binders, lubricants; or known additives (including such as buffers, isotonic agents, chelating agents, coloring agents, preservatives, flagrances, flavoring agents, and sweetening agents).

The anticancer agent of the present invention may be administered orally or parenterally depending on the form of the agent, e.g. oral administration agents such as tablets, capsules, powders, granules, pills, liquids, syrups, etc. and parenteral administration agents such as injections, external medicines, suppositories, eye drops, etc. Preferably, local injection into muscle or abdominal cavity, or intravenous injection may be enumerated.

Dose levels are selected appropriately depending on the kind of active ingredient, the administration route, the target of administration, and the age, body weight, sex, symptoms and other conditions of the patient. Usually, dose levels may be selected so that the virus of the invention (the active ingredient) is administered at a daily dose of about $10^6$-$10^{11}$ PFU, preferably about $10^9$-$10^{11}$ PFU. This amount may be administered once a day, or may be divided into several portions and administered at several times a day.

When the virus of the invention is administered, it is also possible to use a known immunosuppressant or the like to suppress the immunity of the living body to thereby make the viral infection easy.

Further, the virus of the invention may be used jointly with at least one anticancer agent selected from the group consisting of non-replication competent viruses (such as virus comprising p53 gene) used in conventional gene therapy, known anticancer agents and radiation.

The virus of the invention infected to the living body (cancer cells or cancer tissues) is capable of replicating in the cancer cells and bringing death to those cells. By thus bringing death to cancer cells, the virus of the invention can treat cancers, inhibit the growth of tumor cells, and prevent metastasis of cancer cells.

It is believed that there is an extremely low possibility that the anticancer agent of the invention will produce side effects for the reasons described below. Thus, the anticancer agent of the invention can be said a very safe preparation.

(1) There is little telomerase activity in normal somatic cells, and yet adenovirus itself is hard to be infected to suspending cells such as hematopoietic cells. Therefore, when adenovirus is used in the present invention, still higher selectivity for tumor kinds is obtained.

(2) Since the virus of the invention has replication ability, it is possible to use this virus at a lower concentration than that of conventional non-replication competent virus used in conventional gene therapy.

(3) Even when the virus of the invention has been administered in excess, antiviral action works through ordinary immune reaction in the living body.

EXAMPLES

Hereinbelow, examples will be provided in order to illustrate the present invention in more detail. Needless to say, the present invention is not limited to these examples.

Example 1

<Preparation of TRAD>

An E1A gene of 899 bp was amplified from RNA extracted from 293 cells by RT-PCR using specific primers (E1A-S: SEQ ID NO: 5; E1A-AS: SEQ ID NO: 6). An E1B gene of 1823 bp was amplified from DNA extracted from 293 cells by DNA-PCR using primers (E1B-S: SEQ ID NO: 7; E1B-AS: SEQ ID NO: 8).

These PCR products were subjected to TA cloning (TA Cloning Kit Dual Promoter; Invitrogen) to thereby confirm their sequences. Then, DNA fragments of 899 bp (E1A) and 1823 bp (E1B) were cut out, respectively, with restriction enzyme EcoRI.

E1A and E1B were inserted into the MluI site and the SalI site of pIRES vector (Clontech), respectively, in the normal orientation (E1A-IRES-E1B).

A 455 bp hTERT promoter sequence which had been cut out with restriction enzymes MluI and BglII was inserted into the XhoI site located upstream of the E1A of E1A-IRES-E1B (phTERT-E1A-IRES-E1B).

The cytomegalovisus (CMV) promoter contained in pShuttle vector was removed by treatment with restriction enzymes MfeI and NheI. Then, a 3828 bp sequence cut out from phTERT-E1A-IRES-E1B using restriction enzymes NheI and NotI was inserted into that site (pSh-hAIB).

A 4381 bp sequence was cut out from pSh-hAIB using restriction enzymes I-CeuI and PI-SceI, and inserted into the Adeno-X Viral DNA of Adeno-X Expression System (Clontech) (AdenoX-hAIB). This AdenoX-hAIB was treated with restriction enzyme PacI for linearization and then transfected into 293 cells by the phosphate calcium method. Thus, a infectious recombinant adenovirus (TRAD) was prepared. A schematic drawing of TRAD is shown in FIG. 1.

Example 2

<Comparison of Telomerase Activities in Human Cancer Cells and Normal Cells>

Figure 2:
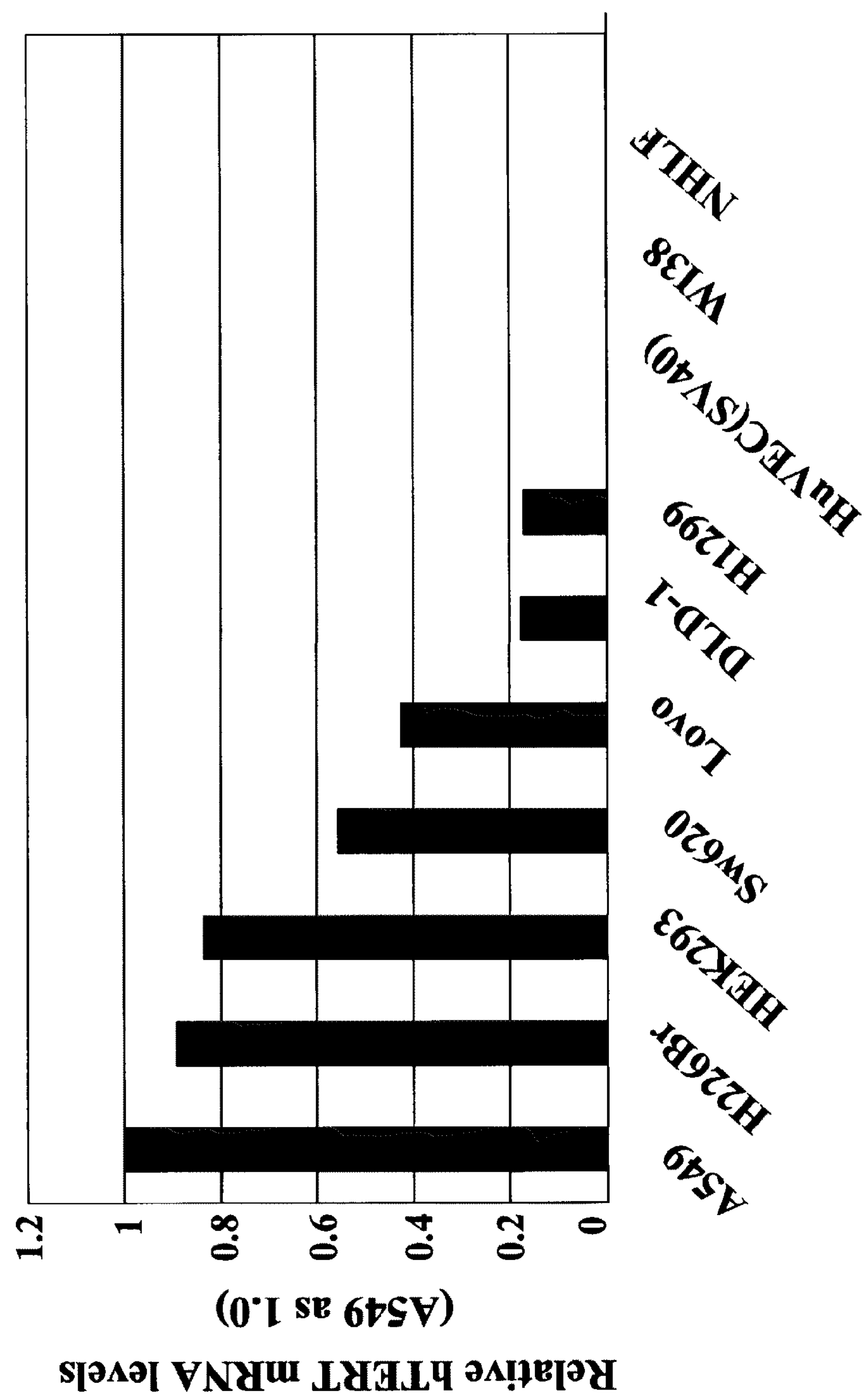
FIG. 2 shows comparison of telomerase activities in human cancer cells and normal cells.

RNA was extracted from the following 10 kinds of cells using RNAzol (Cinna/Biotecx): human lung cancer cells (A549, H226Br and H1299); human large bowel cancer cells (SW620, DLD-1 and LoVo); human embryonic kidney cell 293; human umbilical vascular endothelial cell HUVEC immortalized by the introduction of SV40 gene; and human normal fibroblast cells (WI38 and NHLF). The resultant RNA was subjected to real time quantitative reverse transcription (RT)-PCR using Light Cycler DNA TeloTAGGG Kit (Roche Molecular Biochemicals), followed by comparison of expression levels of hTERT gene in respective cells. The results are shown in FIG. 2.

When expression levels were compared taking the level in A549 cells (which showed the highest expression) as 1.0, hTERT gene expression from 0.18 to 1.00 was observed in cancer cells (such as A549, H226Br, H1299, SW620, DLD-1, Lovo) and 293 cells, whereas no expression was detected in immortalized cell HuVEC and normal cells (such as WI38, NHLF).

Example 3

<Expression of E1A and E1B mRNAs and Proteins after TRAD Infection in Human Cancer Cells and Normal Cells>

Human large bowel cancer cell SW620 and human normal fibroblast cell WI38 were cultured in vitro. Then, each cell was infected with TRAD at concentrations of MOI (multiplicity of infection) 0.1 and 1, followed by recovery of RNA after 36 hours. As a positive control, 293 cells were used.

The recovered RNA was reverse-transcribed using GeneAmp RNA PCR Core Kit. The resultant DNA was amplified 30 cycles in GeneAmp PCR System 9700 Thermal Cycler (PE Applied Biosystems) using primers for E1A gene and E1B gene. The PCR products were electrophoresed on 1.2% agarose gel and stained with ethidium bromide to thereby visualize bands (upper two panels in FIG. 3A). The intensities of the bands were measured with an image analyzer, quantitatively determined using GAPDH as an internal control and then shown in graphs (the bottom panel in FIG. 3A).

Human large bowel cancer cell SW620 and human normal fibroblast cell WI38 were cultured in vitro. Then, each cell was infected with TRAD at concentrations of MOI 0.1 and 1. After 48 hours, adherent cells were recovered and reacted in a lysis solution for 30 minutes, followed by centrifugation. The protein concentration in the resultant supernatant was measured. Briefly, the supernatant was electrophoresed on 12% polyacrylamide gel and transferred onto a membrane. Then, Western blot analysis was performed with anti-adenovirus 5 E1A antibody (PharMingen International). The results are shown in FIG. 3B.

Figure 3:
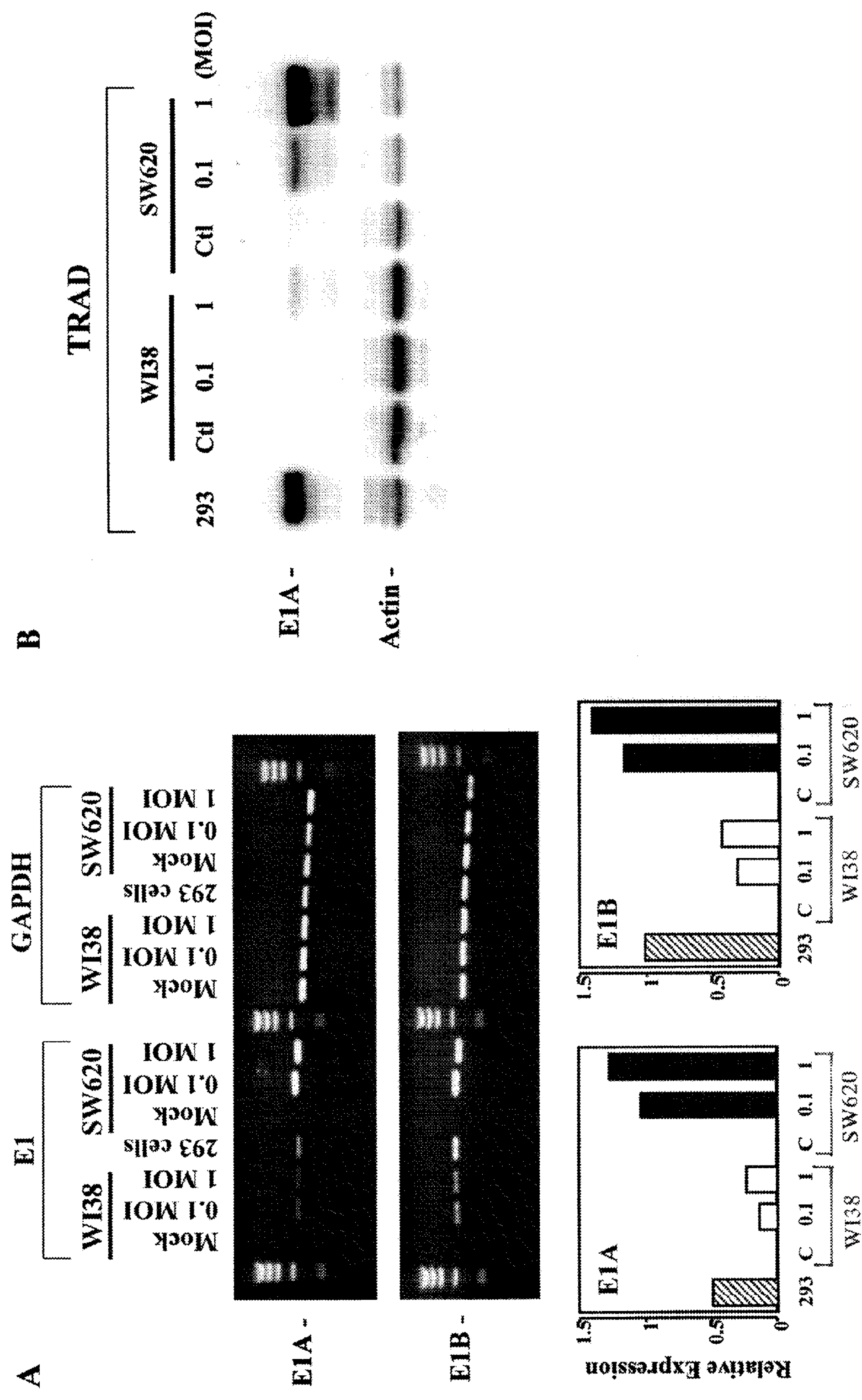
FIG. 3 shows the expression of E1A and E1B mRNAs and proteins after TRAD infection in human cancer cells and normal cells.

While strong expression of E1A gene (502 bp) and E1B gene (543 bp) was clearly observed as a result of TRAD infection in cancer cell SW620, only weak expression of these genes was observed in normal cell WI38 (FIG. 3A). In the positive control 293 cells, medium expression of these genes was observed.

The results of Western blot analysis revealed that expression of E1A protein increased in SW620 as the concentration of TRAD increased from MOI 0.1 to 1 (FIG. 3B). On the other hand, expression of E1A protein was detected little in WI38 even when TRAD was used at MOI 1.

Example 4

<Examination of Intracellular Viral Replication after TRAD Infection in Human Cancer Cells and Normal Cells>

Figure 4:
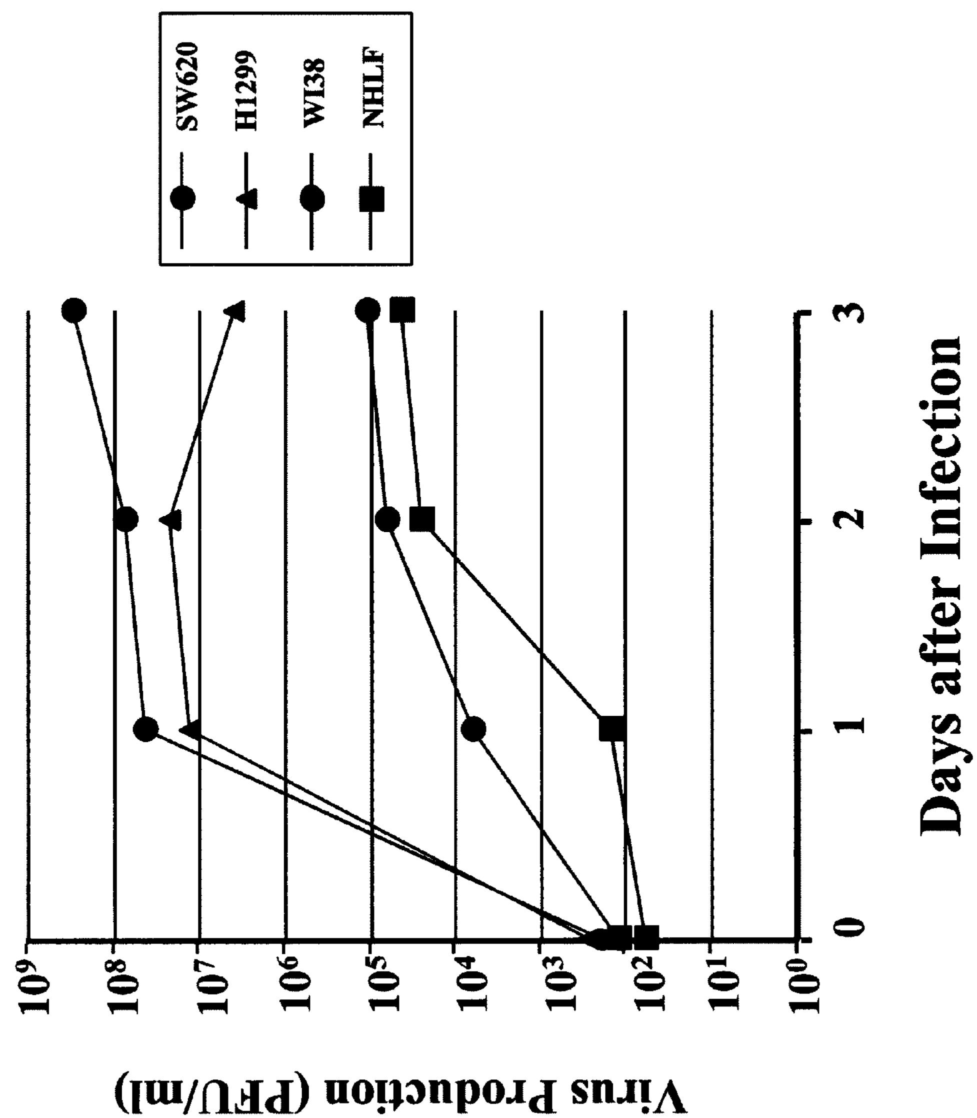
FIG. 4 shows the intracellular replication of the virus after TRAD infection in human cancer cells and normal cells.

Human cancer cells (SW620 and H1299) and human normal cells (WI38 and NHLF) were infected with TRAD at MOI 1 for 2 hours at 37° C. Then, the TRAD-containing culture broth was discarded. After cells were washed with a fresh culture broth once, a fresh culture broth was added further. Immediately thereafter (i.e., on day 0), cells were recovered with a scraper and subjected to repetition of freezing and thawing. Then, they were suspended in 1 ml of a culture broth. Further, virus was recovered on day 1, 2, 3, 5 and 7 in the same manner, followed by measurement of viral titer. The results are shown in FIG. 4.

In normal cells WI38 and NHLF, TRAD increased from $10^2$ PFU on day 1 to about $10^5$ PFU on day 3 showing 100- to 1000-fold growth. On the other hand, in cancer cells SW620 and H1299, TRAD increased to $10^7$-$10^8$ PFU showing $10^5$- to $10^6$-fold growth. Thus, viral growth specific to cancer cells was confirmed.

Example 5

<Cytotoxic Activity of TRAD in Human Cancer Cells and Normal Cells>

Five kinds of human cancer cells (SW620, H1299, A549, DLD-1 and H226Br) were plated on 24-well plates at 6-8×$10^4$ cells/well, and two kinds of human normal cells (WI38 and NHLF) were plated on 24-well plates at 2-4×$10^4$ cells/well. After 24 hours, they were infected with TRAD at MOI 0.01, 0.1, 1, 2 and 5. Ninety-six hours after the infection, morphological changes in SW620, DLD-1 and NHLF cells were observed under microscopy. Further, culture broth was discarded from all of the cells. Then, viable cells were stained with Coomassie brilliant blue, and macroscopic images were taken into with a scanner.

Figure 5:
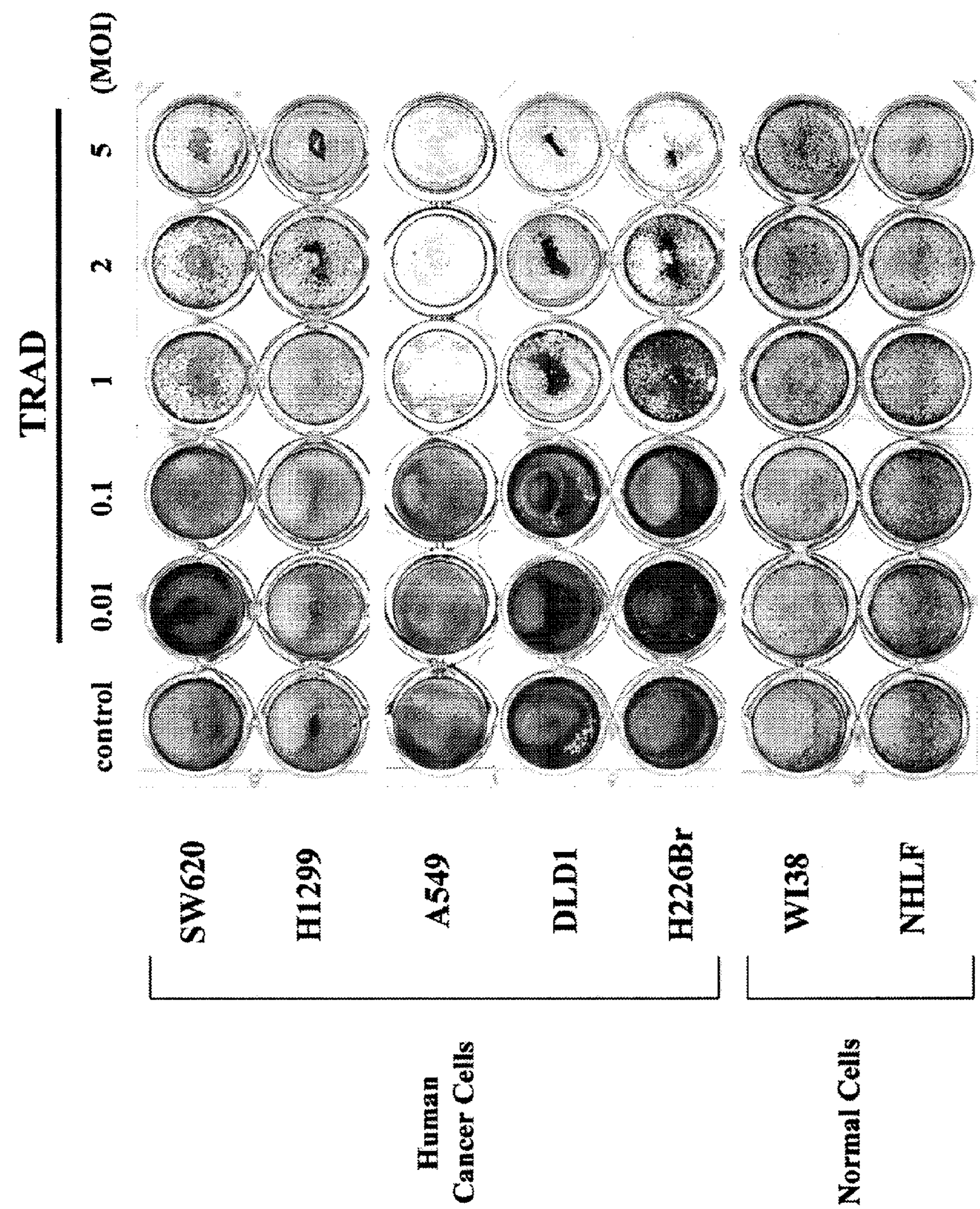
FIG. 5 presents photographs showing, by staining with Coomassie brilliant blue, the cytotoxicity caused by TRAD in human cancer cells and normal cells.
Figure 6:
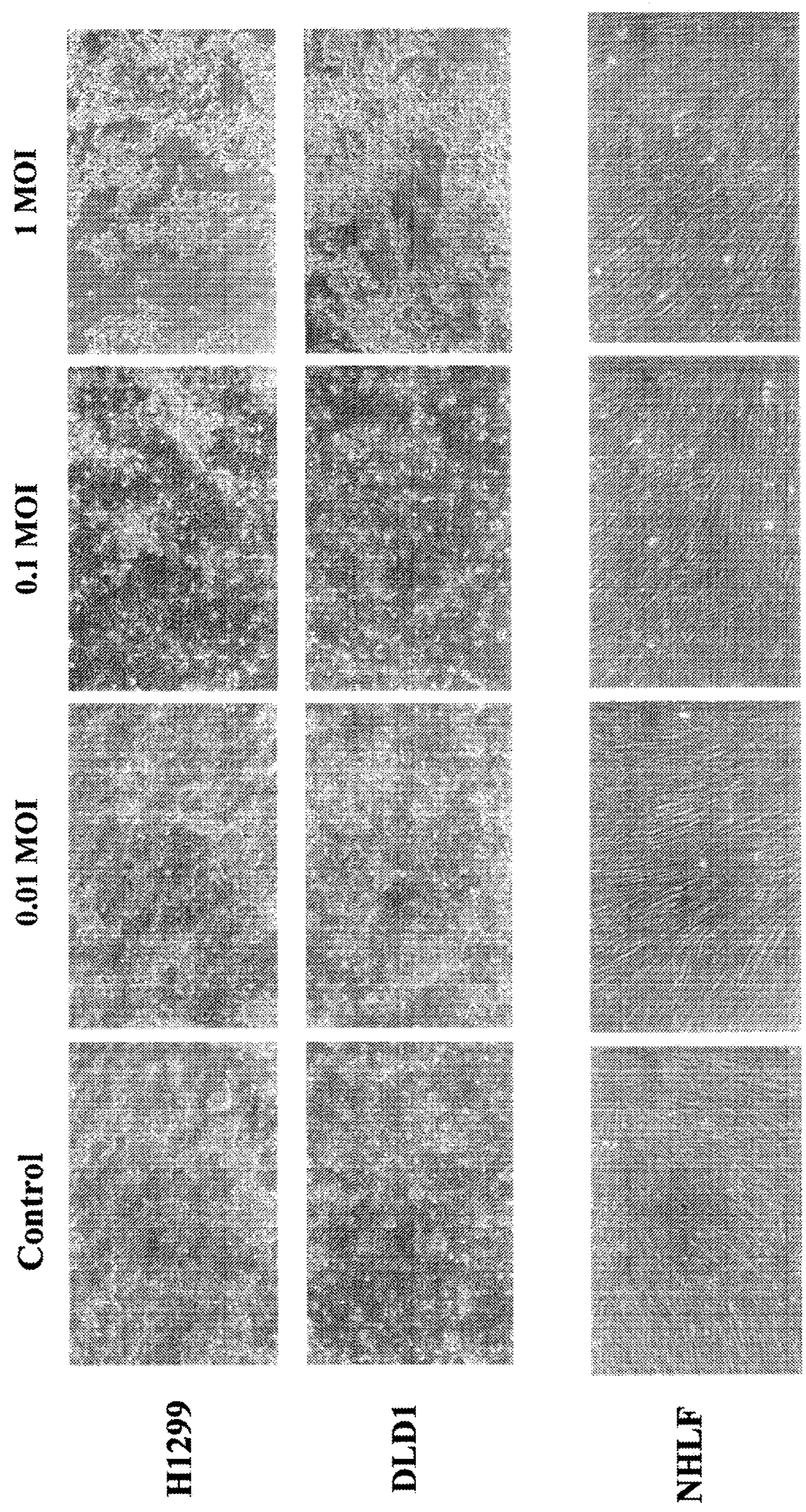
FIG. 6 presents microscopic photographs showing the cytotoxicity caused by TRAD in human cancer cells and normal cells.
Figure 7:
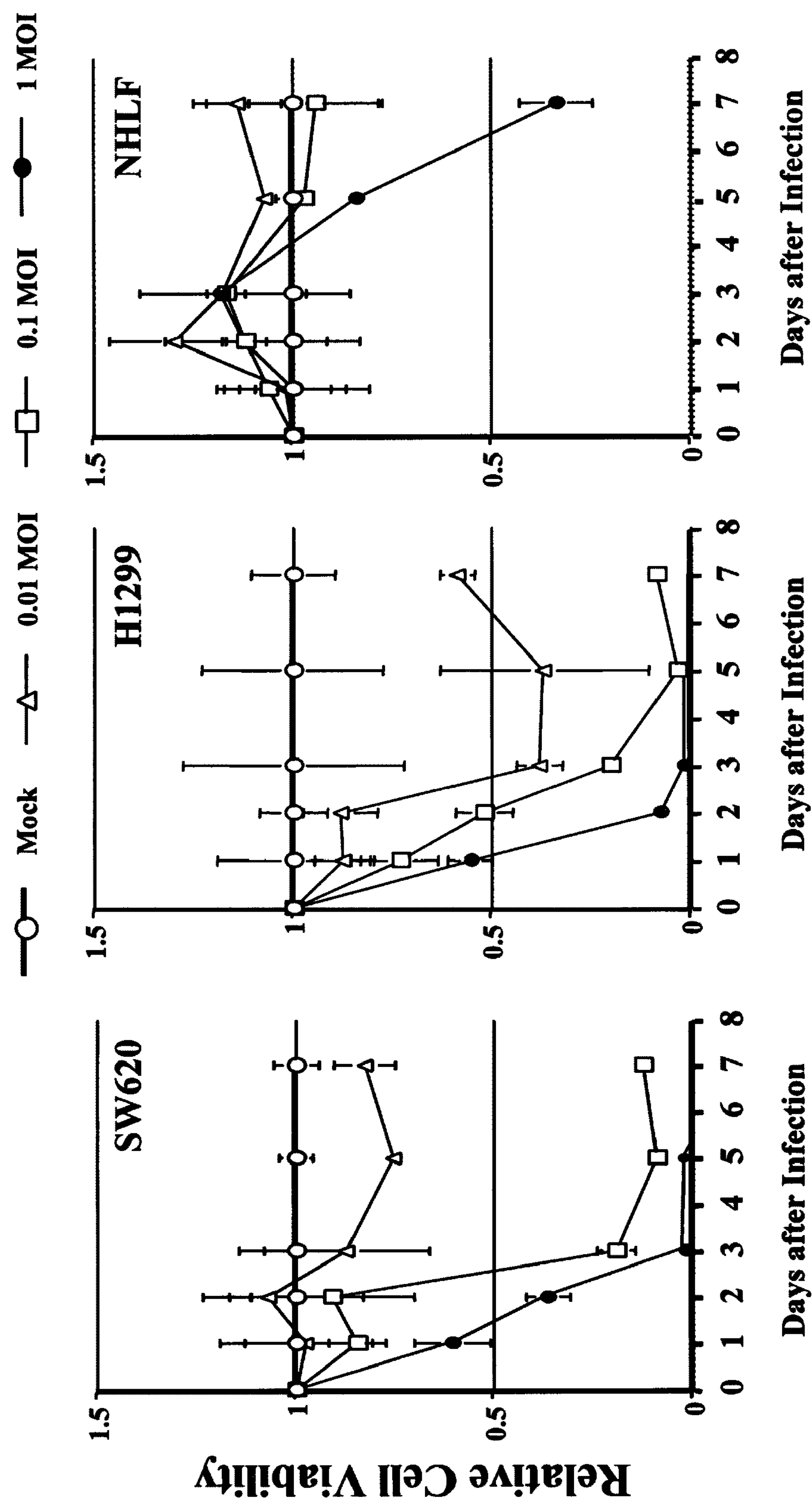
FIG. 7 presents graphs showing by means of XTT assay the cytotoxicity caused by TRAD in human cancer cells and normal cells.

SW620 and H1299 were plated at $10^4$ cells/well and NHLF was plated at 5×$10^3$ cells/well, respectively, on 96-well plates. Cells were infected with TRAD at MOI 0 (non-infected cells), 0.01, 0.1 and 1. Then, the numbers of viable cells were measured by XTT assay on day 1, 2, 3, 5 and 7. The viable cell count was determined for each four wells. Taking the count in the non-infected cells as 1.0, counts in other cells were represented in graphs in means+/−SDs. Respective results are shown in FIGS. 5, 6 and 7.

In cancer cells SW620, H1299, A549, DLD-1 and H226Br, cell counts decrease and areas stained with blue reduce in a TRAD concentration-dependant manner. On the other hand, in normal cells WI38 and NHLF, no remarkable decrease in the number of viable cells stained with blue was recognized (FIG. 5). In the microscopic observation, SW620 and DLD-1 cells were peeled off from the plate bottom, became round-shaped and showed decrease in cell density; on the other hand, NHLF cells showed little morphological change and no decrease in cell count (FIG. 6).

In SW620 and H1299 cells, almost 100% cell death was observed by day 3 as a result of TRAD infection at MOI 1. More than 80% decrease in cell count was recognized even at MOI 0.1. On the other hand, NHLF showed almost no decrease in cell count even on day 3. Although NHLF showed about 60% decrease in cell count on day 7 when TRAD was used at MOI 1, it indicated no viral influence at MOI 0.01 (FIG. 7).

Example 6

<Examination of the Antitumor Activity of TRAD in Animal Models>

Human lung cancer cell H358 was transplanted subcutaneously into the back of 5-6 week-old nude mice at 5×$10^6$ cells/mouse. When the tumor became approximately 5-6 min in diameter, a non-replication competent adenovirus vector (Ad-p53) was injected intratumorally and locally for consecutive two days at 1×$10^8$ PFU, 3×$10^8$ PFU and 1×$10^9$ PFU per day. Then, two axes of each tumor crossing at right angles were measured at regular intervals. The estimated tumor weight was calculated by the following formula: (major axis)×(minor axis)$^2$/2. As a control, a non-replication competent adenovirus vector dl312 containing no inserted gene was used.

Figure 8:
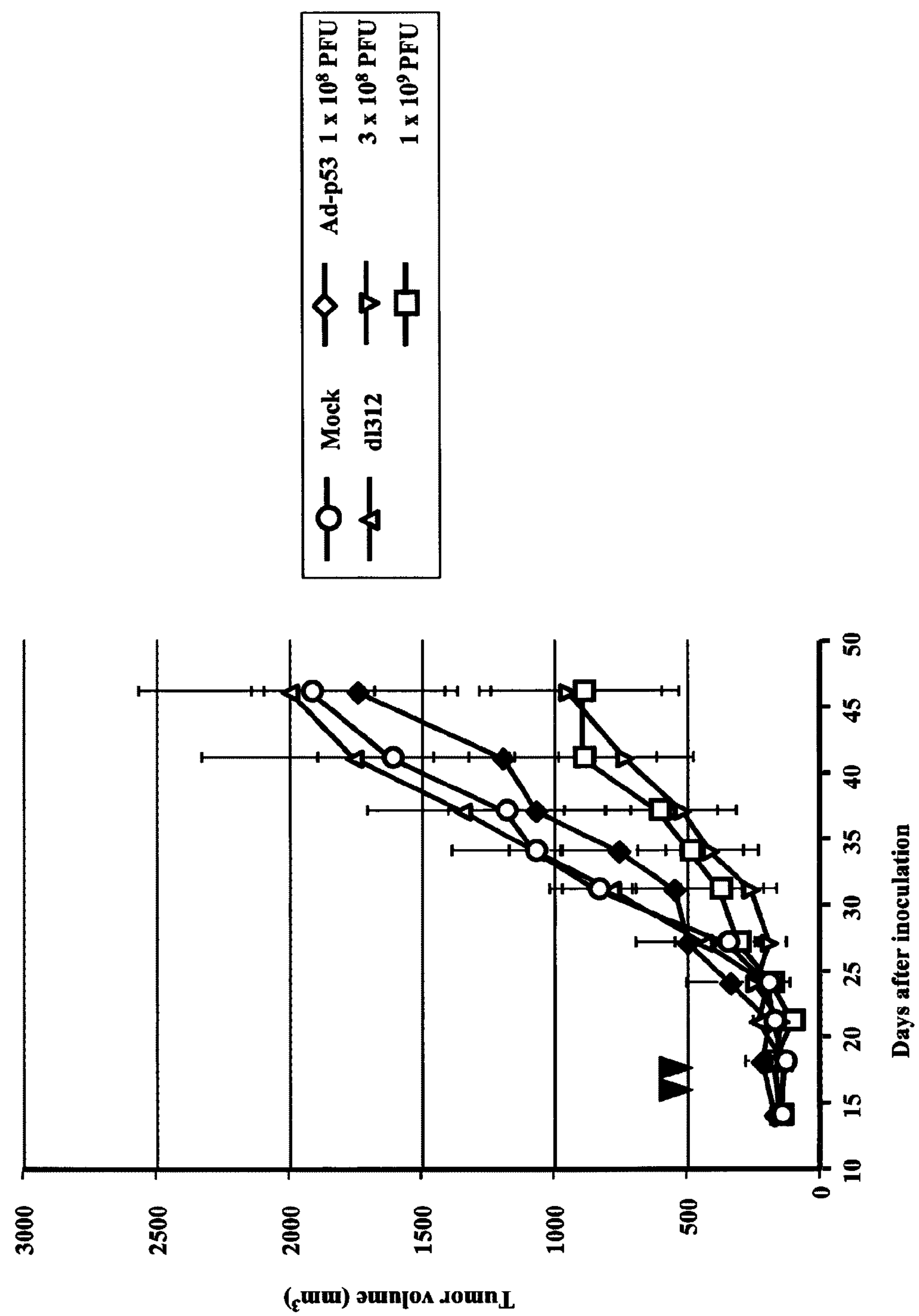
FIG. 8 is a graph showing the antitumor effect produced by intratumoral, local administration of a non-replication competent, p53 gene-expressing adenovirus vector in an experiment using nude mice and human lung cancer cell H358.
Figure 9:
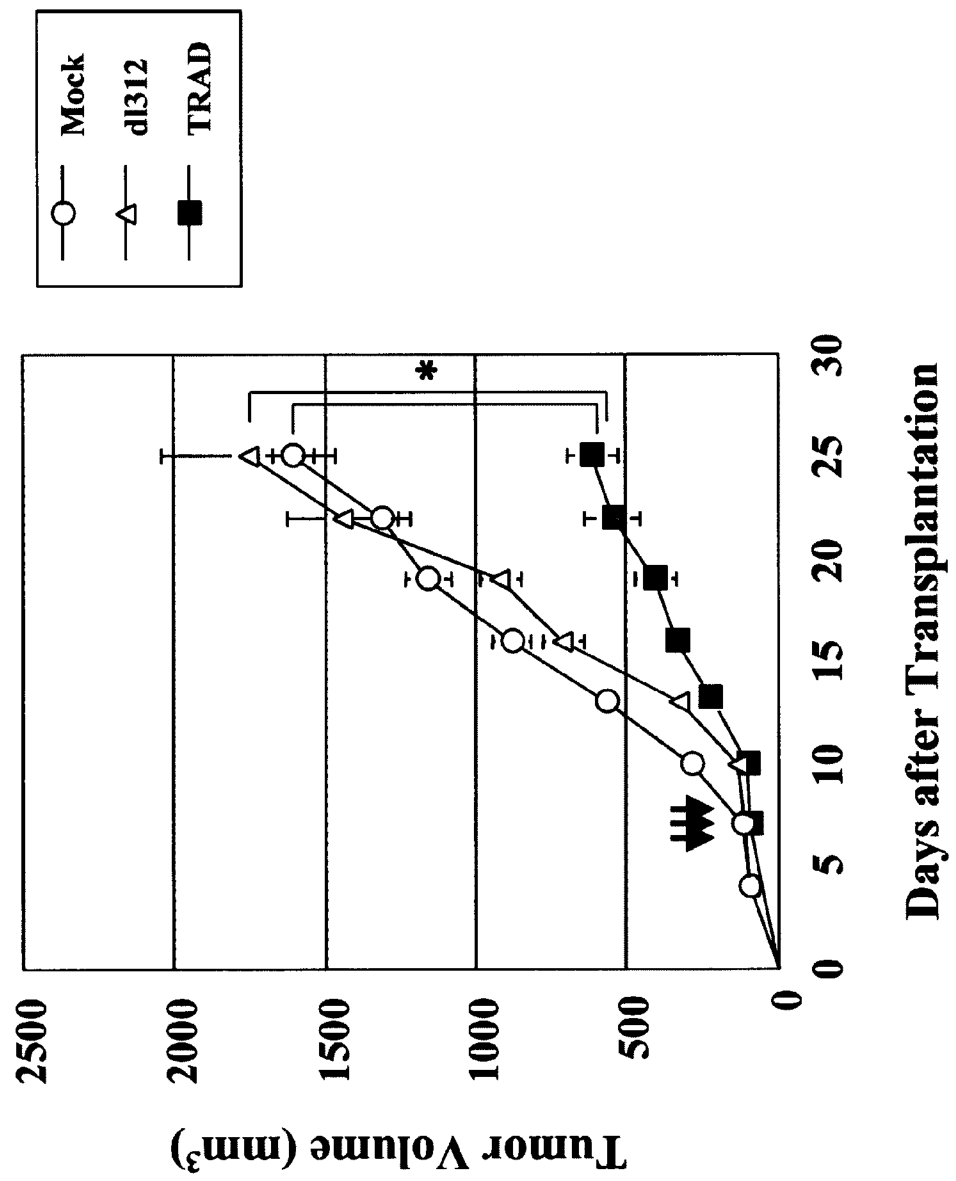
FIG. 9 is a graph showing the antitumor effect produced by intratumoral, local administration of TRAD in an experiment using nude mice and human large bowel cancer cell SW620.

Human large bowel cancer cell SW620 was transplanted subcutaneously into the back of 5-6 week-old nude mice at 5×$10^6$ cells/mouse. When the tumor became approximately 5-6 mm in diameter, 2×$10^7$ PFU of dl312/day and 4×$10^3$ PFU of TRAD/day were injected intratumorally and locally for consecutive three days. The axes of each tumor were measured in the same manner as described above, followed by calculation of the estimated tumor weight. The results are shown in FIGS. 8 and 9 (the term "Mock" appearing in these Figures represents control to which PBS (phosphate buffered saline) was administered).

Administration of Ad-p53 at $3\times10^8$ PFU and $1\times10^9$ PFU inhibited the growth of H358 tumor significantly ($p<0.05$). However, administration of Ad-p53 at $1\times10^8$ PFU revealed no significant growth inhibition (FIG. 8). Administration of dl312 (control) indicated no influence upon tumor growth.

Intratumoral administration of TRAD at $4\times10^3$ PFU, which is extremely lower than the concentration of Ad-p53 that showed antitumor effect, inhibited the growth of SW620 tumor significantly ($p<0.05$). Administration of dl312 (control) indicated no influence upon tumor growth.

From what have been described above, it is understood that the virus of the present invention grows efficiently in cancer cells and brings death to them. Further, since the virus of the invention has the ability to grow, it is capable of manifesting potent anti-cancer effect even at a low concentration. Thus, it is also possible to reduce side effect by administering the virus at a low concentration.

Example 7

<Full Sequencing of TRAD Genome>

In the present example, a full sequencing of TRAD genome was performed by constructing a shotgun library and sequencing the clones to provide 4-fold sequencing data that covers at least one of the two DNA strands.

I. Method (1) Test Samples

In this Example, $1.0\times10^{12}$ particles/ml of TRAD was used as a test sample. The test samples had been stored −80° C.

(2) Shotgun Library Construction and DNA Sequencing (2-1) Shotgun Library Construction Adenoviral DNA was prepared from the test article using a Qiagen viral DNA extraction method. The test article DNA was fragmented and cloned into the Sma I site of the pUC 19 vector to create a shotgun library.

(2-2) DNA Quality Control

Plasmid DNA was prepared from the shotgun library subclones and the presence of inserts was verified by agarose gel electrophoresis of a subset of subclones. The DNA concentrations for a subset of subclones were determined by OD260 reading using a spectrophotometer.

(2-3) Sequencing and Assembly

A total of 384 shotgun library clones were sequenced with pUC forward and reverse vector primers for a total of 768 reactions using the BigDye (registered trademark) Terminator vl. 1 Cycle Sequencing Kit (Applied Biosystems). The data were screened for host and vector DNA sequences and assembled to derive a consensus sequence using the phred/phrap/consed suite of programs on a Linux platform. Sequencing of gaps and terminal repeats was performed by direct sequencing of the adenoviral DNA and sequencing of shotgun subclones derived from the construct. Additional sequencing primers used for gap closure and sequence coverage are given in the following table. An additional 112 finishing reactions were performed. Quality values were determined for each base of the contig. The majority of bases for the consensus sequence had a quality score of 90. The quality score was determined using Phred scaled from 0 to 90 with 90 indicating the highest quality. A score value above 90 indicates a manual editing of that base.

Additional Sequencing Primers

| Primer Name | Sequence | |
|---|---|---|
| AP01 | GAGAGGTCGAATCGGCCTAG | SEQ ID NO: 15 |
| AP02 | CTTCGCAGGGCCAGCTGAAC | SEQ ID NO: 16 |
| AP05 | TAACGAGCCTGGGCAACCT | SEQ ID NO: 17 |
| AP06 | GTCGGTCAAGCCTTGCCTTG | SEQ ID NO: 18 |
| AP07 | CCTTATAAGCATAAGACGGAC | SEQ ID NO: 19 |
| AP08 | CAGCTCAATCAGTCACAGTG | SEQ ID NO: 20 |
| AP09 | GTCAAGAAGACAGGGCCAGG | SEQ ID NO: 21 |
| AP10 | GGCTGTGGAATGTATCGAGG | SEQ ID NO: 22 |
| AP11 | TAATGTTGTCTCTACGCCTG | SEQ ID NO: 23 |
| AP12 | AACCGCACGCGAACCTACG | SEQ ID NO: 24 |
| AP13 | GGCCGAACACTCGTGCTGG | SEQ ID NO: 25 |
| AP14 | TCTGCGAAACCGCCTCCTC | SEQ ID NO: 26 |

II. Result

The assembly resulted in a contig, consisting of 732 reads with a contig length of 37, 289 bp (SEQ ID NO: 14). This result demonstrated that TRAD comprises a nucleotide sequence of SEQ ID NO: 14.

TRAD comprising the nucleotide sequence of SEQ ID NO: 14 was used in the following Clinical Trial (Example 8).

Example 8

<Clinical Trial of TRAD>

Presented herein are results of a clinical trial using TRAD, an adenovirus containing: hTERT promoter+E1A-IRES-E1B construct. The methods utilized in the clinical trials also fall within the scope of the presently claimed methods for treating a cancer. The results of the clinical trails described herein further illustrate the ability of the claimed polynucleotide and vector constructs to replicate in cancer cells as well as to kill the cancer cells. This clinical trial was done under the inventor's supervision.

A phase I study was designed to determine the feasibility and to characterize the pharmacokinetics of TRAD in patients with advanced solid tumors.

I. Method

A phase I dose-escalation trial was conducted in patients with histologically-confirmed solid tumors (n=16) total; TRAD was injected directly into an index tumor $<25\ cm^2$ and $>1\ cm^2$ at single, ascending doses of $1\times10^{10}$, $1\times10^{11}$, and $1\times10^{12}$ viral particles/tumor. All patients had failed standard chemo and radiotherapy.

II. Result

Sixteen patients (3 patients in cohort 1 and cohort 2, 10 patients in cohort 3) were treated. The primary tumor types were head and neck (n=2), breast (n=1), soft tissue (n=1), and others (n=5). Mild to moderate fatigue (56%), chills (38%), pyrexia (38%), injection site pain (31%) were the most commonly reported adverse events. Dose-limiting toxicity and unexpected severe adverse events were not observed. Nine out of 11 patients evaluated for response had stable disease at the day 28 assessment, and 9 patients showed 6.7% to 45.5% tumor size reduction. These results are summarized in the following tables 1 and 2.

TABLE 1

| First Occurrence of All Adverse Events Reported by At Least 20% of Patients | | | | |
|---|---|---|---|---|
| System Organ Class Preferred Term | $1 \times 10^{10}$ VP (N = 3) N (%) | $1 \times 10^{11}$ VP (N = 3) N (%) | $1 \times 10^{12}$ VP (N = 10) N (%) | Total (N = 16) N (%) |
| General Disorders and Administration Site Conditions | | | | |
| Chills | 0 (0%) | 0 (0%) | 6 (60%) | 6 (38%) |
| Fatigue | 1 (33%) | 2 (67%) | 6 (60%) | 9 (56%) |
| Injection Site Erythema | 1 (33%) | 1 (33%) | 2 (20%) | 4 (25%) |
| Injection Site Pain | 1 (33%) | 2 (67%) | 2 (20%) | 5 (31%) |

TABLE 1-continued

| First Occurrence of All Adverse Events Reported by At Least 20% of Patients | | | | |
|---|---|---|---|---|
| System Organ Class Preferred Term | $1 \times 10^{10}$ VP (N = 3) N (%) | $1 \times 10^{11}$ VP (N = 3) N (%) | $1 \times 10^{12}$ VP (N = 10) N (%) | Total (N = 16) N (%) |
| Pain | 0 (0%) | 2 (67%) | 2 (20%) | 4 (25%) |
| Pyrexia | 0 (0%) | 0 (0%) | 6 (60%) | 6 (38%) |
| Nervous System Disorders | | | | |
| Headache | 1 (33%) | 2 (67%) | 1 (10%) | 4 (25%) |

TABLE 2

Tumor size assessment - treated target lesion

| No. | Dose | Primary | Injection Site | Tumor Size | Tumor Response |
|---|---|---|---|---|---|
| 1 | Cohort 1 | SCC Primary unknown | Right Axillary Lymph Node | Pre-Injection: 2.5 × 1.5 (cm)<br>Day 28: 2.5 × 1.6 (cm)<br>Day 56: N/A (Resected) | Pre-Injection: 100%<br>Day 28: +6.6%<br>Day 56: N/A (Resected) |
| 2 | Cohort 1 | Melanoma | Left Axillary Node | Pre-Injection: 4 × 2.8 (cm)<br>Day 28: 3.8 × 2.5 (cm)<br>Day 56: 4 × 2.5 (cm) | Pre-Injection: 100%<br>Day 28: −15.2%<br>Day 56: −10.8% |
| 3 | Cohort 1 | Melanoma | Right Breast | Pre-Injection: 4.2 × 3.3 (cm)<br>Day 28: 3.6 × 2.8 (cm)<br>Day 56: N/A (Next Trial) | Pre-Injection: 100%<br>Day 28: −27.3%<br>Day 56: N/A (Next Trial) |
| 4 | Cohort 2 | Salivary Grand | Left Head & Neck | Pre-Injection: 4.5 × 3.2 (cm)<br>Day 28: 4.3 × 3.2 (cm)<br>Day 56: 4.5 × 3.1 (cm) | Pre-Injection: 100%<br>Day 28: −4.5%<br>Day 56: −3.2% |
| 5 | Cohort 2 | SCCHN | Right Head & Neck | Pre-Injection: 2.5 × 1.7 (cm)<br>Day 28: 2.2 × 1.7 (cm)<br>Day 56: 2.6 × 1.7 (cm) | Pre-Injection: 100%<br>Day 28: −12%<br>Day 56: +4% |
| 6 | Cohort 2 | Leiomyo sarcoma | Right Abdomen | Pre-Injection: 2.5 × 2.0 (cm)<br>Day 28: 2.2 × 2.0 (cm)<br>Day 56: N/A (Next Trial) | Pre-Injection: 100%<br>Day 28: −12%<br>Day 56: N/A (Next Trial) |
| 7 | Cohort 3 | Lung Cancer | Right Pelvis | Pre-Injection: 1.7 × 1.5 (cm)<br>Day 28: 1.7 × 1.4 (cm)<br>Day 56: 1.7 × 1.4 (cm) | Pre-Injection: 100%<br>Day 28: −6.7%<br>Day 56: −6.7% |
| 8 | Cohort 3 | Melanoma | Left Musculoskeletal Soft Tissue | Pre-Injection: 3.3 × 1.4 (cm)<br>Day 28: 2.8 × 1.1 (cm)<br>Day 56: 2.5 × 0.8 (cm) | Pre-Injection: 100%<br>Day 28: −33.4%<br>Day 56: −56.8% |
| 9 | Cohort 3 | NSCLC | Right Axillary Node | Pre-Injection: 3.5 × 4.7 (cm)<br>Day 28: 4.8 × 3.5 (cm)<br>Day 56: 5.0 × 3.7 (cm) | Pre-Injection: 100%<br>Day 28: +2%<br>Day 56: +12.4% |
| 10 | Cohort 3 | SCCHN | Right Head & Neck | Pre-Injection: 2.8 × 1.8 (cm)<br>Day 28: N/A (Not evaluable)<br>Day 56: 3.1 × 2.1 (cm) | Pre-Injection: 100%<br>Day 28: N/A<br>Day 56: +29% |
| 11 | Cohort 3 | SCCHN | Right Head & Neck | Pre-Injection: 5.0 × 2.6 (cm)<br>Day 28: 7.2 × 3.2 (cm)<br>Day 56: N/A (PD) | Pre-Injection: 100%<br>Day 28: +77.2%<br>Day 56: N/A (PD) |
| 12 | Cohort 3 | Melanoma | Left Lower Leg | Pre-Injection: 1.5 × 1.5 (cm)<br>Day 28: N/A (Not evaluable)<br>Day 56: N/A (PD)-new lesion) | Pre-Injection: 100%<br>Day 28: N/A (Not evaluable)<br>Day 56: N/A (PD-new lesion) |
| 13 | Cohort 3 | Sarcoma | Left Head & Neck | Pre-Injection: 5.5 × 3.4 (cm)<br>Day 28: N/A (Withdraw)<br>Day 56: N/A (Withdraw) | Pre-Injection: 100%<br>Day 28: N/A (Withdraw)<br>Day 56: N/A (Withdraw) |
| 14 | Cohort 3 | Basal Cell Cancer | Right Head & Neck | Pre-Injection: 2.8 × 1 (cm)<br>Day 28: 1.7 × 0.9 (cm)<br>Day 56: N/A (Next Trial) | Pre-Injection: 100%<br>Day 28: −45.4%<br>Day 56: N/A (Next Trial) |
| 15 | Cohort 3 | Gall Bladder Cancer | Left Liver | Pre-Injection: 3.5 × 2.9 (cm)<br>Day 28: 2.9 × 2.8 (cm)<br>Day 56: 4.3 × 4.4 (cm) | Pre-Injection: 100%<br>Day 28: −20%<br>Day 56: +86% |
| 16 | Cohort 3 | Breast Cancer | Left Liver | Pre-Injection: 1.5 × 0.9 (cm)<br>Day 28: N/A (Withdraw)<br>Day 56: N/A (Withdraw) | Pre-Injection: 100%<br>Day 28: N/A<br>Day 56: N/A |

SCC = Squamous Cell Cartinoma

SCCHN = Squamous Cell Cartinoma Head & Neck

NSCLC = Non Small Cell Lung Cancer

As shown in the above tables, no dose-limiting toxicity, or maximally tolerated dose was identified. The virus TRAD was well-tolerated at doses producing infection in the cancer cells, demonstrated early antitumoral activity as reflected in the reduced tumor sizes, and is an excellent cancer treatment candidate.

In the clinical trial, the virus TRAD according to the presently claimed virus, was successfully and safely administered to 16 patients, and no serious side effects were observed. These results illustrate the targeting specificity of TRAD (i.e., the minimal, or few side effects indicate little or no replication in normal cells), and show the virus TRAD replicates in and kills cancer cells.

The following data provide additional details of data obtained from three patients out of the above-described sixteen patients in the clinical trial.

Patient #01103 (No. 3 in Table 2)

Diagnosis: Metastatic Melanoma

In March of 2004, a 35 year old female, was diagnosed as advanced melanoma with metastasis to the liver and spleen. The patient was treated with temozolomide from May 2005-August 2005 with stable disease. She was also treated with interferon in July 2004 with stable disease. Recently, she was treated with an experimental dendritic cell vaccine, with overall response of PD. The baseline expression of hTERT mRNA in the biopsy tissue to be injected was positive.

On Feb. 15, 2007, the patient received a single intratumoral injection of TRAD ($1\times10^{10}$ VP) into the right breast mass (4.2×3.3 cm [13.9 $cm^2$]).

On the next day after treatment, she experienced mild soreness at injection site, which was considered related to TRAD injection. And as the evidence of inflammation at the injected tumor, the peak of serum IFN-gamma and the peak of body temperature (37.1° C.) were observed on day 1 after the injection.

On 28 days after injection, 27.3% tumor shrinkage was observed at treated tumor lesion (3.6×2.8 cm [10.1 $cm^2$]).

After the evaluation at the visit on day 28, the patient was subsequently enrolled into another clinical trial.

Patient #01208 (No. 8 in Table 2)

Diagnosis: Metastatic Melanoma

On February of 2007, a 72 year old female with history of COPD, was diagnosed as melanoma at the left ankle. She received a knee amputation on Apr. 5 of 2007 and a biopsy of the left inguinal node on the same day to find recurrence in the inguinal node. The recurred tumor was found at a left medial thigh node on May 11, 2007. She received 2 doses of interferon from Jun. 11 to 18 of 2007. The baseline expression of hTERT mRNA in the biopsy tissue to be injected was positive.

On Jul. 30 of 2007, the patient received a single intratumoral injection of TRAD ($1\times10^{12}$ VP) into the tumor at medial left thigh (3.3×1.4 cm [4.6 $cm^2$]) of melanoma. She experienced mild bruising at the injection site and mild skin lesion from removing band-aid on day 7. As the evidence of inflammation at the injected tumor, the peak of IL-6 and IL-10 peak were observed on Day 1. On the day 22, mild panic attack prior to visit. The panic attach was thought to be due to information the patient heard about her brother. The patient contacted her physician's office and was instructed to take Xanax for her anxiety. The only adverse event thought to be probably related to study treatment was bruising at the injection site.

On day 28 after injection, 33.4% tumor shrinkage was observed at treated tumor lesion (2.8×1.1 cm [3.1 $cm^2$]), and pathological response were also observed at injected lesion. On day 56 after injection, 56.8% tumor shrinkage was observed at treated tumor lesion (2.5×0.8 cm [2.0 $cm^2$]) (FIG. 10).

Figure 10:
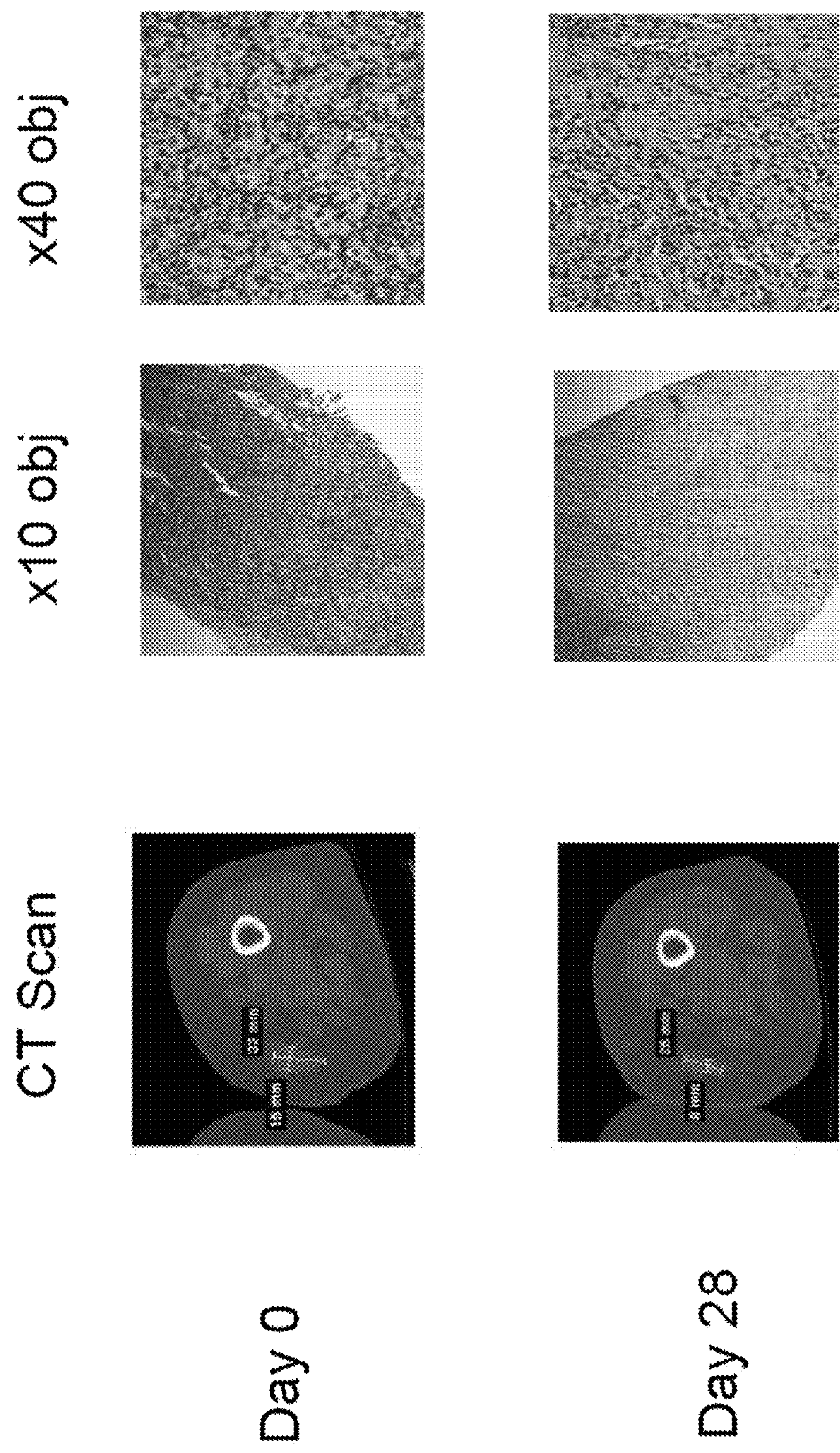
FIG. 10 presents photographs showing the results of CT scan on the human cancer patients or the results of staining of tumor lesion.

In addition, as shown in the FIG. 10, on Day 0, a large part of the tissue was basophilic ("x10 obj" of upper panel) and melanoma cells and lymphocytes infiltrated ("x40 obj" of upper panel), in contrast, on Day 28, tissues were rather eosinophilic ("x10 obj" of lower panel) and plasma cells infiltrated and there were no apparent tumor cells ("x40 obj" of lower panel).

Patient #01214 (No. 14 in Table 2)

Diagnosis: Basal Cell Carcinoma

In 2001, a 54 year old male, was diagnosed as basal cell carcinoma in back. He had it removed surgically, and was diagnosed with basal cell cancer. One year later his disease recurred at the scar on his scalp. He then received a second surgery. Lung metastasis was found and followed by 2 cycles of Cisplatin and 5-FU in February 2005. The recurrence at scalp was found on November 2007, and at the right neck and bilateral supraclavicular region, metastasis was found on Dec. 6 of 2007. The baseline expression of hTERT mRNA in the biopsy tissue to be injected was positive.

On Jan. 17 of 2008, he received a single intratumoral injection of TRAD ($1\times10^{12}$ VP) into the tumor at right suboccipital scalp (2.8×1.0 cm [2.8 $cm^2$]). He experienced mild fever, achiness and chills on the day of study treatment. These adverse events were thought to be probably related to TRAD injection.

On day 28 after injection, 6.7% tumor shrinkage was observed at treated tumor lesion (1.7×0.9 cm [1.5 $cm^2$]). On day 56 after injection, the tumor size of treated tumor lesion remained the size as on 28 days after injection.

In the clinical trial, the virus TRAD was successfully and safely administered to the patients, and no serious side effects were observed. In general, it is highly important for the human patient in the cancer treatment that no serious side effects were observed. Therefore, the above-described results (i.e., causing tumor shrinkage without serious side effect in human patient) show surprising and advantageous effects of the present invention which is unpredictable for the one of ordinary skill in the art.

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:

1. A polynucleotide cassette comprising an hTERT promoter operably linked with an E1A gene, an IRES sequence and an E1B gene, in that order, wherein the polynucleotide cassette comprises a nucleotide sequence having at least 99% identity to the nucleotide sequence consisting of SEQ ID NO:12, wherein said polynucleotide cassette enables an adenovirus to replicate selectively in tumor cells.

2. A recombinant adenovirus comprising the polynucleotide cassette of claim 1.

3. A polynucleotide cassette comprising an hTERT promoter operably linked with an E1A gene, an IRES sequence and an E1B gene, in that order, wherein the polynucleotide cassette comprises the nucleotide sequence of SEQ ID NO:12.

4. A recombinant adenovirus comprising the polynucleotide cassette of claim 3.

5. A recombinant adenovirus comprising the nucleotide sequence of SEQ ID NO:14.

* * * * *

SEQUENCE LISTING

<160> NUMBER OF SEQ ID NOS: 29

<210> SEQ ID NO 1
<211> LENGTH: 899
<212> TYPE: DNA
<213> ORGANISM: Adenovirus

<400> SEQUENCE: 1

```
acaccgggac tgaaaatgag acatattatc tgccacggag gtgttattac cgaagaaatg     60
gccgccagtc ttttggacca gctgatcgaa gaggtactgg ctgataatct tccacctcct    120
agccattttg aaccacctac ccttcacgaa ctgtatgatt tagacgtgac ggcccccgaa    180
gatcccaacg aggaggcggt ttcgcagatt tttcccgact ctgtaatgtt ggcggtgcag    240
gaagggattg acttactcac ttttccgccg gcgcccggtt ctccggagcc gcctcacctt    300
tcccggcagc ccgagcagcc ggagcagaga gccttgggtc cggtttctat gccaaacctt    360
gtaccggagg tgatcgatct tacctgccac gaggctggct ttccacccag tgacgacgag    420
gatgaagagg gtgaggagtt tgtgttagat tatgtggagc accccgggca cggttgcagg    480
tcttgtcatt atcaccggag gaatacgggg gacccagata ttatgtgttc gctttgctat    540
atgaggacct gtggcatgtt tgtctacagt cctgtgtctg aacctgagcc tgagcccgag    600
ccagaaccgg agcctgcaag acctacccgc cgtcctaaaa tggcgcctgc tatcctgaga    660
cgcccgacat cacctgtgtc tagagaatgc aatagtagta cggatagctg tgactccggt    720
ccttctaaca cacctcctga gatacacccg gtggtcccgc tgtgccccat taaaccagtt    780
gccgtgagag ttggtgggcg tcgccaggct gtggaatgta tcgaggactt gcttaacgag    840
cctgggcaac ctttggactt gagctgtaaa cgccccaggc cataaggtgt aaacctgtg     899
```

<210> SEQ ID NO 2
<211> LENGTH: 1823
<212> TYPE: DNA
<213> ORGANISM: Adenovirus

<400> SEQUENCE: 2

```
ctgacctcat ggaggcttgg gagtgtttgg aagatttttc tgctgtgcgt aacttgctgg     60
aacagagctc taacagtacc tcttggtttt ggaggtttct gtggggctca tcccaggcaa    120
agttagtctg cagaattaag gaggattaca agtgggaatt tgaagagctt ttgaaatcct    180
gtggtgagct gtttgattct ttgaatctgg gtcaccaggc gcttttccaa gagaaggtca    240
tcaagacttt ggatttttcc acaccggggc gcgctgcggc tgctgttgct tttttgagtt    300
ttataaagga taaatggagc gaagaaaccc atctgagcgg ggggtacctg ctggattttc    360
tggccatgca tctgtggaga gcggttgtga gacacaagaa tcgcctgcta ctgttgtctt    420
ccgtccgccc ggcgataata ccgacggagg agcagcagca gcagcaggag gaagccaggc    480
ggcggcggca ggagcagagc ccatggaacc cgagagccgg cctggaccct cgggaatgaa    540
tgttgtacag gtggctgaac tgtatccaga actgagacgc attttgacaa ttacagagga    600
tgggcagggg ctaaaggggg taaagaggga gcggggggct tgtgaggcta cagaggaggc    660
taggaatcta gcttttagct taatgaccag acaccgtcct gagtgtatta cttttcaaca    720
gatcaaggat aattgcgcta atgagcttga tctgctggcg cagaagtatt ccatagagca    780
gctgaccact tactggctgc agccagggga tgattttgag gaggctatta gggtatatgc    840
aaaggtggca cttaggccag attgcaagta caagatcagc aaacttgtaa atatcaggaa    900
```

```
ttgttgctac atttctggga acggggccga ggtggagata gatacggagg atagggtggc    960

ctttagatgt agcatgataa atatgtggcc gggggtgctt ggcatggacg ggtggttat   1020

tatgaatgta aggtttactg gccccaattt tagcggtacg gttttcctgg ccaataccaa   1080

ccttatccta cacggtgtaa gcttctatgg gtttaacaat acctgtgtgg aagcctggac   1140

cgatgtaagg gttcggggct gtgcctttta ctgctgctgg aagggggtgg tgtgtcgccc   1200

caaaagcagg gcttcaatta agaaatgcct ctttgaaagg tgtaccttgg gtatcctgtc   1260

tgagggtaac tccagggtgc gccacaatgt ggcctccgac tgtggttgct tcatgctagt   1320

gaaaagcgtg gctgtgatta agcataacat ggtatgtggc aactgcgagg acagggcctc   1380

tcagatgctg acctgctcgg acggcaactg tcacctgctg aagaccattc acgtagccag   1440

ccactctcgc aaggcctggc cagtgtttga gcataacata ctgacccgct gttccttgca   1500

tttgggtaac aggagggggg tgttcctacc ttaccaatgc aatttgagtc acactaagat   1560

attgcttgag cccgagagca tgtccaaggt gaacctgaac ggggtgtttg acatgaccat   1620

gaagatctgg aaggtgctga ggtacgatga gacccgcacc aggtgcagac cctgcgagtg   1680

tggcggtaaa catattagga accagcctgt gatgctggat gtgaccgagg agctgaggcc   1740

cgatcacttg gtgctggcct gcacccgcgc tgagtttggc tctagcgatg aagatacaga   1800

ttgaggtact gaaatgtgtg ggc                                           1823
```

<210> SEQ ID NO 3
<211> LENGTH: 605
<212> TYPE: DNA
<213> ORGANISM: Picornavirus

<400> SEQUENCE: 3

```
tgcatctagg gcggccaatt ccgcccctct ccctcccccc cccctaacgt tactggccga     60

agccgcttgg aataaggccg gtgtgcgttt gtctatatgt gattttccac catattgccg    120

tcttttggca atgtgagggc ccggaaacct ggccctgtct tcttgacgag cattcctagg    180

ggtctttccc ctctcgccaa aggaatgcaa ggtctgttga atgtcgtgaa ggaagcagtt    240

cctctggaag cttcttgaag acaaacaacg tctgtagcga ccctttgcag gcagcggaac    300

cccccacctg gcgacaggtg cctctgcggc caaaagccac gtgtataaga tacacctgca    360

aaggcggcac aaccccagtg ccacgttgtg agttggatag ttgtggaaag agtcaaatgg    420

ctctcctcaa gcgtattcaa caaggggctg aaggatgccc agaaggtacc ccattgtatg    480

ggatctgatc tggggcctcg gtgcacatgc tttacatgtg tttagtcgag gttaaaaaaa    540

cgtctaggcc ccccgaacca cggggacgtg gttttccttt gaaaaacacg atgataagct    600

tgcca                                                               605
```

<210> SEQ ID NO 4
<211> LENGTH: 455
<212> TYPE: DNA
<213> ORGANISM: Homo sapiens

<400> SEQUENCE: 4

```
tggcccctcc ctcgggttac cccacagcct aggccgattc gacctctctc cgctggggcc     60

ctcgctggcg tccctgcacc ctgggagcgc gagcggcgcg cgggcgggga agcgcggccc    120

agacccccgg gtccgcccgg agcagctgcg ctgtcggggc caggccgggc tcccagtgga    180

ttcgcgggca cagacgccca ggaccgcgct ccccacgtgg cggagggact ggggacccgg    240

gcacccgtcc tgccccttca ccttccagct ccgcctcctc cgcgcggacc ccgccccgtc    300
```

```
ccgacccctc ccgggtcccc ggcccagccc cctccgggcc ctcccagccc ctccccttcc    360

tttccgcggc cccgccctct cctcgcggcg cgagtttcag gcagcgctgc gtcctgctgc    420

gcacgtggga agccctggcc ccggccaccc ccgcg                                455


<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5

acaccgggac tgaaaatgag                                                  20


<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6

cacaggttta caccttatgg c                                                21


<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7

ctgacctcat ggaggcttgg                                                  20


<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8

gcccacacat ttcagtacct c                                                21


<210> SEQ ID NO 9
<211> LENGTH: 1823
<212> TYPE: DNA
<213> ORGANISM: Adenovirus

<400> SEQUENCE: 9

ctgacctcat ggaggcttgg gagtgtttgg aagatttttc tgctgtgcgt aacttgctgg     60

aacagagctc taacagtacc tcttggtttt ggaggtttct gtggggctca tcccaggcaa    120

agttagtctg cagaattaag gaggattaca agtgggaatt tgaagagctt ttgaaatcct    180

gtggtgagct gtttgattct ttgaatctgg gtcaccaggc gcttttccaa gagaaggtca    240

tcaagacttt ggatttttcc acaccggggc gcgctgcggc tgctgttgct tttttgagtt    300

ttataaagga taaatggagc gaagaaaccc atctgagcgg ggggtacctg ctggattttc    360

tggccatgca tctgtggaga gcggttgtga gacacaagaa tcgcctgcta ctgttgtctt    420

ccgtccgccc ggcgataata ccgacggagg agcagcagca gcagcaggag gaagccaggc    480

ggcggcggca ggagcagagc ccatggaacc cgagagccgg cctggaccct cgggaatgaa    540
```

```
tgttgtacag gtggctgaac tgtatccaga actgagacgc attttgacaa ttacagagga    600

tgggcagggg ctaaaggggg taaagaggga gcgggggct tgtgaggcta cagaggaggc     660

taggaatcta gcttttagct taatgaccag acaccgtcct gagtgtatta cttttcaaca    720

gatcaaggat aattgcgcta atgagcttga tctgctggcg cagaagtatt ccatagagca    780

gctgaccact tactggctgc agccagggga tgattttgag gaggctatta gggtatatgc    840

aaaggtggca cttaggccag attgcaagta caagatcagc aaacttgtaa atatcaggaa    900

ttgttgctac atctctggga acggggccga ggtggagata gatacggagg atagggtggc    960

ctttagatgt agcatgataa atatgtggcc gggggtgctt ggcatggacg gggtggttat   1020

tatgaatgta aggtttactg gccccaattt tagcggtacg gttttcctgg ccaataccaa   1080

ccttatccta cacggtgtaa gcttctatgg gtttaacaat acctgtgtgg aagcctggac   1140

cgatgtaagg gttcggggct gtgcctttta ctgctgctgg aagggggtgg tgtgtcgccc   1200

caaaagcagg gcttcaatta agaaatgcct ctttgaaagg tgtaccttgg gtatcctgtc   1260

tgagggtaac tccagggtgc gccacaatgt ggcctccgac tgtggttgct tcatgctagt   1320

gaaaagcgtg gctgtgatta agcataacat ggtatgtggc aactgcgagg acagggcctc   1380

tcagatgctg acctgctcgg acggcaactg tcacctgctg aagaccattc acgtagccag   1440

ccactctcgc aaggcctggc cagtgtttga gcataacata ctgacccgct gttccttgca   1500

tttgggtaac aggagggggg tgttcctacc ttaccaatgc aatttgagtc acactaagat   1560

attgcttgag cccgagagca tgtccaaggt gaacctgaac ggggtgtttg acatgaccat   1620

gaagatctgg aaggtgctga ggtacgatga gacccgcacc aggtgcagac cctgcgagtg   1680

tggcggtaaa catattagga accagcctgt gatgctggat gtgaccgagg agctgaggcc   1740

cgatcacttg gtgctggcct gcacccgcgc tgagtttggc tctagcgatg aagatacaga   1800

ttgaggtact gaaatatgtg ggc                                            1823
```

<210> SEQ ID NO 10
<211> LENGTH: 621
<212> TYPE: DNA
<213> ORGANISM: Picornavirus

<400> SEQUENCE: 10

```
tgcatctagg gcggccaatt ccgcccctct cccccccccc cctctccctc cccccccccc     60

taacgttact ggccgaagcc gcttggaata aggccggtgt gcgtttgtct atatgttatt    120

ttccaccata ttgccgtctt ttggcaatgt gagggcccgg aaacctggcc ctgtcttctt    180

gacgagcatt cctaggggtc tttcccctct cgccaaagga atgcaaggtc tgttgaatgt    240

cgtgaaggaa gcagttcctc tggaagcttc ttgaagacaa acaacgtctg tagcgaccct    300

ttgcaggcag cggaaccccc cacctggcga caggtgcctc tgcggccaaa agccacgtgt    360

ataagataca cctgcaaagg cggcacaacc ccagtgccac gttgtgagtt ggatagttgt    420

ggaaagagtc aaatggctct cctcaagcgt attcaacaag gggctgaagg atgcccagaa    480

ggtaccccat tgtatgggat ctgatctggg gcctcggtgc acatgcttta catgtgttta    540

gtcgaggtta aaaaaacgtc taggcccccc gaaccacggg gacgtggttt tcctttgaaa    600

aacacgatga taagcttgcc a                                              621
```

<210> SEQ ID NO 11
<211> LENGTH: 3869
<212> TYPE: DNA
<213> ORGANISM: Artificial
<220> FEATURE:

<223> OTHER INFORMATION: synthetic DNA

<400> SEQUENCE: 11

```
tggcccctcc ctcgggttac cccacagcct aggccgattc gacctctctc cgctggggcc     60
ctcgctggcg tccctgcacc ctgggagcgc gagcggcgcg cgggcgggga agcgcggccc    120
agacccccgg gtccgcccgg agcagctgcg ctgtcggggc caggccgggc tcccagtgga    180
ttcgcgggca cagacgccca ggaccgcgct ccccacgtgg cggagggact ggggacccgg    240
gcacccgtcc tgccccttca ccttccagct ccgcctcctc cgcgcggacc ccgccccgtc    300
ccgacccctc ccgggtcccc ggcccagccc cctccgggcc ctcccagccc ctccccttcc    360
tttccgcggc cccgccctct cctcgcggcg cgagtttcag gcagcgctgc gtcctgctgc    420
gcacgtggga agccctggcc ccggccaccc ccgcgataga tctcgagaat tcacgcgaat    480
tcggcttaca ccgggactga aaatgagaca tattatctgc cacggaggtg ttattaccga    540
agaaatggcc gccagtcttt tggaccagct gatcgaagag gtactggctg ataatcttcc    600
acctcctagc cattttgaac cacctaccct tcacgaactg tatgatttag acgtgacggc    660
ccccgaagat cccaacgagg aggcggtttc gcagattttt cccgactctg taatgttggc    720
ggtgcaggaa gggattgact tactcacttt tccgccggcg cccggttctc cggagccgcc    780
tcacctttcc cggcagcccg agcagccgga gcagagagcc ttgggtccgg tttctatgcc    840
aaaccttgta ccggaggtga tcgatcttac ctgccacgag gctggctttc cacccagtga    900
cgacgaggat gaagagggtg aggagtttgt gttagattat gtggagcacc ccgggcacgg    960
ttgcaggtct tgtcattatc accggaggaa tacgggggac ccagatatta tgtgttcgct   1020
ttgctatatg aggacctgtg gcatgtttgt ctacagtcct gtgtctgaac ctgagcctga   1080
gcccgagcca gaaccggagc ctgcaagacc tacccgccgt cctaaaatgg cgcctgctat   1140
cctgagacgc ccgacatcac ctgtgtctag agaatgcaat agtagtacgg atagctgtga   1200
ctccggtcct tctaacacac ctcctgagat acacccggtg gtcccgctgt gccccattaa   1260
accagttgcc gtgagagttg gtgggcgtcg ccaggctgtg gaatgtatcg aggacttgct   1320
taacgagcct gggcaacctt tggacttgag ctgtaaacgc cccaggccat aaggtgtaaa   1380
cctgtgaagc cgaattcgcg tcgagcatgc atctagggcg gccaattccg cccctctccc   1440
tcccccccc ctaacgttac tggccgaagc cgcttggaat aaggccggtg tgcgtttgtc   1500
tatatgtgat tttccaccat attgccgtct tttggcaatg tgagggcccg gaaacctggc   1560
cctgtcttct tgacgagcat tcctaggggt ctttcccctc tcgccaaagg aatgcaaggt   1620
ctgttgaatg tcgtgaagga agcagttcct ctggaagctt cttgaagaca aacaacgtct   1680
gtagcgaccc tttgcaggca gcggaacccc ccacctggcg acaggtgcct ctgcggccaa   1740
aagccacgtg tataagatac acctgcaaag gcggcacaac cccagtgcca cgttgtgagt   1800
tggatagttg tggaaagagt caaatggctc tcctcaagcg tattcaacaa ggggctgaag   1860
gatgcccaga aggtacccca ttgtatggga tctgatctgg ggcctcggtg cacatgcttt   1920
acatgtgttt agtcgaggtt aaaaaaacgt ctaggccccc cgaaccacgg ggacgtggtt   1980
ttcctttgaa aaacacgatg ataagcttgc cacaacccgg gatcctctag agtcgaaatt   2040
cggcttctga cctcatggag gcttgggagt gtttggaaga tttttctgct gtgcgtaact   2100
tgctggaaca gagctctaac agtacctctt ggttttggag gtttctgtgg ggctcatccc   2160
aggcaaagtt agtctgcaga attaaggagg attacaagtg ggaatttgaa gagcttttga   2220
aatcctgtgg tgagctgttt gattctttga atctgggtca ccaggcgctt ttccaagaga   2280
```

```
aggtcatcaa gactttggat ttttccacac cggggcgcgc tgcggctgct gttgcttttt   2340

tgagttttat aaaggataaa tggagcgaag aaacccatct gagcgggggg tacctgctgg   2400

atttctggc catgcatctg tggagagcgg ttgtgagaca caagaatcgc ctgctactgt   2460

tgtcttccgt ccgcccggcg ataataccga cggaggagca gcagcagcag caggaggaag   2520

ccaggcggcg gcggcaggag cagagcccat ggaacccgag agccggcctg gaccctcggg   2580

aatgaatgtt gtacaggtgg ctgaactgta tccagaactg agacgcattt tgacaattac   2640

agaggatggg caggggctaa agggggtaaa gagggagcgg ggggcttgtg aggctacaga   2700

ggaggctagg aatctagctt ttagcttaat gaccagacac cgtcctgagt gtattacttt   2760

tcaacagatc aaggataatt gcgctaatga gcttgatctg ctggcgcaga agtattccat   2820

agagcagctg accacttact ggctgcagcc aggggatgat tttgaggagg ctattagggt   2880

atatgcaaag gtggcactta ggccagattg caagtacaag atcagcaaac ttgtaaatat   2940

caggaattgt tgctacattt ctgggaacgg ggccgaggtg gagatagata cggaggatag   3000

ggtggccttt agatgtagca tgataaatat gtggccgggg gtgcttggca tggacggggt   3060

ggttattatg aatgtaaggt ttactggccc caattttagc ggtacggttt tcctggccaa   3120

taccaacctt atcctacacg gtgtaagctt ctatgggttt aacaatacct gtgtggaagc   3180

ctggaccgat gtaagggttc ggggctgtgc cttttactgc tgctggaagg gggtggtgtg   3240

tcgccccaaa agcagggctt caattaagaa atgcctcttt gaaaggtgta ccttgggtat   3300

cctgtctgag ggtaactcca gggtgcgcca caatgtggcc tccgactgtg gttgcttcat   3360

gctagtgaaa agcgtggctg tgattaagca taacatggta tgtggcaact gcgaggacag   3420

ggcctctcag atgctgacct gctcggacgg caactgtcac ctgctgaaga ccattcacgt   3480

agccagccac tctcgcaagg cctggccagt gtttgagcat aacatactga cccgctgttc   3540

cttgcatttg ggtaacagga ggggggtgtt cctaccttac caatgcaatt tgagtcacac   3600

taagatattg cttgagcccg agagcatgtc caaggtgaac ctgaacgggg tgtttgacat   3660

gaccatgaag atctggaagg tgctgaggta cgatgagacc cgcaccaggt gcagaccctg   3720

cgagtgtggc ggtaaacata ttaggaacca gcctgtgatg ctggatgtga ccgaggagct   3780

gaggcccgat cacttggtgc tggcctgcac ccgcgctgag tttggctcta gcgatgaaga   3840

tacagattga ggtactgaaa tgtgtgggc                                     3869
```

```
<210> SEQ ID NO 12
<211> LENGTH: 3885
<212> TYPE: DNA
<213> ORGANISM: Artificial
<220> FEATURE:
<223> OTHER INFORMATION: synthetic DNA

<400> SEQUENCE: 12

tggcccctcc ctcgggttac cccacagcct aggccgattc gacctctctc cgctggggcc     60

ctcgctggcg tccctgcacc ctgggagcgc gagcggcgcg cgggcgggga agcgcggccc    120

agacccccgg gtccgcccgg agcagctgcg ctgtcggggc caggccgggc tcccagtgga    180

ttcgcgggca cagacgccca ggaccgcgct ccccacgtgg cggagggact ggggacccgg    240

gcacccgtcc tgccccttca ccttccagct ccgcctcctc cgcgcggacc ccgccccgtc    300

ccgacccctc ccgggtcccc ggcccagccc cctccgggcc ctcccagccc ctccccttcc    360

tttccgcggc cccgccctct cctcgcggcg cgagtttcag gcagcgctgc gtcctgctgc    420

gcacgtggga agccctggcc ccggccaccc ccgcgataga tctcgagaat tcacgcgaat    480
```

```
tcggcttaca ccgggactga aaatgagaca tattatctgc cacggaggtg ttattaccga    540
agaaatggcc gccagtcttt tggaccagct gatcgaagag gtactggctg ataatcttcc    600
acctcctagc cattttgaac cacctaccct tcacgaactg tatgatttag acgtgacggc    660
ccccgaagat cccaacgagg aggcggtttc gcagattttt cccgactctg taatgttggc    720
ggtgcaggaa gggattgact tactcacttt tccgccggcg cccggttctc cggagccgcc    780
tcacctttcc cggcagcccg agcagccgga gcagagagcc ttgggtccgg tttctatgcc    840
aaaccttgta ccggaggtga tcgatcttac ctgccacgag gctggctttc cacccagtga    900
cgacgaggat gaagagggtg aggagtttgt gttagattat gtggagcacc ccgggcacgg    960
ttgcaggtct tgtcattatc accggaggaa tacgggggac ccagatatta tgtgttcgct   1020
ttgctatatg aggacctgtg gcatgtttgt ctacagtcct gtgtctgaac ctgagcctga   1080
gcccgagcca gaaccggagc ctgcaagacc tacccgccgt cctaaaatgg cgcctgctat   1140
cctgagacgc ccgacatcac ctgtgtctag agaatgcaat agtagtacgg atagctgtga   1200
ctccggtcct tctaacacac ctcctgagat acacccggtg gtcccgctgt gccccattaa   1260
accagttgcc gtgagagttg gtgggcgtcg ccaggctgtg gaatgtatcg aggacttgct   1320
taacgagcct gggcaacctt tggacttgag ctgtaaacgc cccaggccat aaggtgtaaa   1380
cctgtgaagc cgaattcgcg tcgagcatgc atctagggcg gccaattccg cccctctccc   1440
cccccccct ctccctcccc cccccctaa cgttactggc cgaagccgct tggaataagg   1500
ccggtgtgcg tttgtctata tgttattttc caccatattg ccgtcttttg gcaatgtgag   1560
ggcccggaaa cctggccctg tcttcttgac gagcattcct aggggtcttt cccctctcgc   1620
caaaggaatg caaggtctgt tgaatgtcgt gaaggaagca gttcctctgg aagcttcttg   1680
aagacaaaca acgtctgtag cgaccctttg caggcagcgg aaccccccac ctggcgacag   1740
gtgcctctgc ggccaaaagc cacgtgtata agatacacct gcaaaggcgg cacaacccca   1800
gtgccacgtt gtgagttgga tagttgtgga aagagtcaaa tggctctcct caagcgtatt   1860
caacaagggg ctgaaggatg cccagaaggt accccattgt atgggatctg atctggggcc   1920
tcggtgcaca tgctttacat gtgtttagtc gaggttaaaa aacgtctag gcccccgaa    1980
ccacggggac gtggttttcc tttgaaaaac acgatgataa gcttgccaca acccgggatc   2040
ctctagagtc gaaattcggc ttctgacctc atggaggctt gggagtgttt ggaagatttt   2100
tctgctgtgc gtaacttgct ggaacagagc tctaacagta cctcttggtt ttggaggttt   2160
ctgtggggct catcccaggc aaagttagtc tgcagaatta aggaggatta caagtgggaa   2220
tttgaagagc ttttgaaatc ctgtggtgag ctgtttgatt ctttgaatct gggtcaccag   2280
gcgcttttcc aagagaaggt catcaagact ttggattttt ccacaccggg gcgcgctgcg   2340
gctgctgttg cttttttgag ttttataaag gataaatgga gcgaagaaac ccatctgagc   2400
gggggggtacc tgctggattt tctggccatg catctgtgga gagcggttgt gagacacaag   2460
aatcgcctgc tactgttgtc ttccgtccgc ccggcgataa taccgacgga ggagcagcag   2520
cagcagcagg aggaagccag gcggcggcgg caggagcaga gcccatggaa cccgagagcc   2580
ggcctggacc ctcgggaatg aatgttgtac aggtggctga actgtatcca gaactgagac   2640
gcattttgac aattacagag gatgggcagg ggctaaaggg ggtaaagagg gagcgggggg   2700
cttgtgaggc tacagaggag gctaggaatc tagcttttag cttaatgacc agacaccgtc   2760
ctgagtgtat tacttttcaa cagatcaagg ataattgcgc taatgagctt gatctgctgg   2820
cgcagaagta ttccatagag cagctgacca cttactggct gcagccaggg gatgattttg   2880
```

```
aggaggctat tagggtatat gcaaaggtgg cacttaggcc agattgcaag tacaagatca   2940
gcaaacttgt aaatatcagg aattgttgct acatctctgg gaacggggcc gaggtggaga   3000
tagatacgga ggatagggtg gcctttagat gtagcatgat aaatatgtgg ccgggggtgc   3060
ttggcatgga cggggtggtt attatgaatg taaggtttac tggccccaat tttagcggta   3120
cggttttcct ggccaatacc aaccttatcc tacacggtgt aagcttctat gggtttaaca   3180
atacctgtgt ggaagcctgg accgatgtaa gggttcgggg ctgtgccttt tactgctgct   3240
ggaagggggt ggtgtgtcgc cccaaaagca gggcttcaat taagaaatgc ctctttgaaa   3300
ggtgtacctt gggtatcctg tctgagggta actccagggt gcgccacaat gtggcctccg   3360
actgtggttg cttcatgcta gtgaaaagcg tggctgtgat taagcataac atggtatgtg   3420
gcaactgcga ggacagggcc tctcagatgc tgacctgctc ggacggcaac tgtcacctgc   3480
tgaagaccat tcacgtagcc agccactctc gcaaggcctg gccagtgttt gagcataaca   3540
tactgacccg ctgttccttg catttgggta acaggagggg ggtgttccta ccttaccaat   3600
gcaatttgag tcacactaag atattgcttg agcccgagag catgtccaag gtgaacctga   3660
acggggtgtt tgacatgacc atgaagatct ggaaggtgct gaggtacgat gagacccgca   3720
ccaggtgcag accctgcgag tgtggcggta aacatattag gaaccagcct gtgatgctgg   3780
atgtgaccga ggagctgagg cccgatcact tggtgctggc ctgcacccgc gctgagtttg   3840
gctctagcga tgaagataca gattgaggta ctgaaatatg tgggc                    3885
```

<210> SEQ ID NO 13
<211> LENGTH: 29208
<212> TYPE: DNA
<213> ORGANISM: Artificial
<220> FEATURE:
<223> OTHER INFORMATION: synthetic DNA

<400> SEQUENCE: 13

```
catcatcaat aatatacctt attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgtttttg    180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tctctagcat cgtaactata    360
acggtcctaa ggtagcgaaa gctcagatct cccgatcccc tatggtgcac tctcagtaca    420
atctgctctg atgccgcata gttaagccag tatctgctcc ctgcttgtgt gttggaggtc    480
gctgagtagt gcgcgagcaa aatttaagct acaacaaggc aaggcttgac cgacaattct    540
agcctcgacg cgttggcccc tccctcgggt taccccacag cctaggccga ttcgacctct    600
ctccgctggg gccctcgctg gcgtccctgc accctgggag cgcgagcggc gcgcgggcgg    660
ggaagcgcgg cccagacccc cgggtccgcc cggagcagct gcgctgtcgg ggccaggccg    720
ggctcccagt ggattcgcgg gcacagacgc ccaggaccgc gctccccacg tggcggaggg    780
actggggacc cgggcacccg tcctgcccct tcaccttcca gctccgcctc ctccgcgcgg    840
accccgcccc gtcccgaccc ctcccgggtc cccggcccag ccccctccgg gccctcccag    900
cccctcccct tcctttccgc ggccccgccc tctcctcgcg gcgcgagttt caggcagcgc    960
tgcgtcctgc tgcgcacgtg ggaagccctg gccccggcca cccccgcgat agatctcgag   1020
aattcacgcg aattcggctt acaccgggac tgaaaatgag acatattatc tgccacggag   1080
```

-continued

```
gtgttattac cgaagaaatg gccgccagtc ttttggacca gctgatcgaa gaggtactgg   1140
ctgataatct tccacctcct agccattttg aaccacctac ccttcacgaa ctgtatgatt   1200
tagacgtgac ggcccccgaa gatcccaacg aggaggcggt ttcgcagatt tttcccgact   1260
ctgtaatgtt ggcggtgcag gaagggattg acttactcac ttttccgccg gcgcccggtt   1320
ctccggagcc gcctcacctt tcccggcagc ccgagcagcc ggagcagaga gccttgggtc   1380
cggtttctat gccaaacctt gtaccggagg tgatcgatct tacctgccac gaggctggct   1440
ttccacccag tgacgacgag gatgaagagg gtgaggagtt tgtgttagat tatgtggagc   1500
accccgggca cggttgcagg tcttgtcatt atcaccggag gaatacgggg gacccagata   1560
ttatgtgttc gctttgctat atgaggacct gtggcatgtt tgtctacagt cctgtgtctg   1620
aacctgagcc tgagcccgag ccagaaccgg agcctgcaag acctacccgc cgtcctaaaa   1680
tggcgcctgc tatcctgaga cgcccgacat cacctgtgtc tagagaatgc aatagtagta   1740
cggatagctg tgactccggt ccttctaaca cacctcctga gatacacccg gtggtcccgc   1800
tgtgccccat taaaccagtt gccgtgagag ttggtgggcg tcgccaggct gtggaatgta   1860
tcgaggactt gcttaacgag cctgggcaac ctttggactt gagctgtaaa cgccccaggc   1920
cataaggtgt aaacctgtga agccgaattc gcgtcgagca tgcatctagg gcggccaatt   1980
ccgcccctct cccccccccc cctctccctc cccccccccc taacgttact ggccgaagcc   2040
gcttggaata aggccggtgt gcgtttgtct atatgttatt ttccaccata ttgccgtctt   2100
ttggcaatgt gagggcccgg aaacctggcc ctgtcttctt gacgagcatt cctaggggtc   2160
tttcccctct cgccaaagga atgcaaggtc tgttgaatgt cgtgaaggaa gcagttcctc   2220
tggaagcttc ttgaagacaa acaacgtctg tagcgaccct ttgcaggcag cggaaccccc   2280
cacctggcga caggtgcctc tgcggccaaa agccacgtgt ataagataca cctgcaaagg   2340
cggcacaacc ccagtgccac gttgtgagtt ggatagttgt ggaaagagtc aaatggctct   2400
cctcaagcgt attcaacaag gggctgaagg atgcccagaa ggtaccccat tgtatgggat   2460
ctgatctggg gcctcggtgc acatgcttta catgtgttta gtcgaggtta aaaaaacgtc   2520
taggcccccc gaaccacggg gacgtggttt tcctttgaaa aacacgatga taagcttgcc   2580
acaacccggg atcctctaga gtcgaaattc ggcttctgac ctcatggagg cttgggagtg   2640
tttggaagat ttttctgctg tgcgtaactt gctggaacag agctctaaca gtacctcttg   2700
gttttggagg tttctgtggg gctcatccca ggcaaagtta gtctgcagaa ttaaggagga   2760
ttacaagtgg gaatttgaag agcttttgaa atcctgtggt gagctgtttg attctttgaa   2820
tctgggtcac caggcgcttt tccaagagaa ggtcatcaag actttggatt tttccacacc   2880
ggggcgcgct gcggctgctg ttgctttttt gagttttata aaggataaat ggagcgaaga   2940
aacccatctg agcggggggt acctgctgga ttttctggcc atgcatctgt ggagagcggt   3000
tgtgagacac aagaatcgcc tgctactgtt gtcttccgtc cgcccggcga taataccgac   3060
ggaggagcag cagcagcagc aggaggaagc caggcggcgg cggcaggagc agagcccatg   3120
gaacccgaga gccggcctgg accctcggga atgaatgttg tacaggtggc tgaactgtat   3180
ccagaactga gacgcatttt gacaattaca gaggatgggc aggggctaaa gggggtaaag   3240
agggagcggg gggcttgtga ggctacagag gaggctagga atctagcttt tagcttaatg   3300
accagacacc gtcctgagtg tattactttt caacagatca aggataattg cgctaatgag   3360
cttgatctgc tggcgcagaa gtattccata gagcagctga ccacttactg gctgcagcca   3420
ggggatgatt ttgaggaggc tattagggta tatgcaaagg tggcacttag gccagattgc   3480
```

```
aagtacaaga tcagcaaact tgtaaatatc aggaattgtt gctacatctc tgggaacggg   3540
gccgaggtgg agatagatac ggaggatagg gtggccttta gatgtagcat gataaatatg   3600
tggccggggg tgcttggcat ggacggggtg gttattatga atgtaaggtt tactggcccc   3660
aattttagcg gtacggtttt cctggccaat accaacctta tcctacacgg tgtaagcttc   3720
tatgggttta acaatacctg tgtggaagcc tggaccgatg taagggttcg gggctgtgcc   3780
ttttactgct gctggaaggg ggtggtgtgt cgccccaaaa gcagggcttc aattaagaaa   3840
tgcctctttg aaaggtgtac cttgggtatc ctgtctgagg gtaactccag ggtgcgccac   3900
aatgtggcct ccgactgtgg ttgcttcatg ctagtgaaaa gcgtggctgt gattaagcat   3960
aacatggtat gtggcaactg cgaggacagg gcctctcaga tgctgacctg ctcggacggc   4020
aactgtcacc tgctgaagac cattcacgta gccagccact ctcgcaaggc ctggccagtg   4080
tttgagcata acatactgac ccgctgttcc ttgcatttgg gtaacaggag gggggtgttc   4140
ctaccttacc aatgcaattt gagtcacact aagatattgc ttgagcccga gagcatgtcc   4200
aaggtgaacc tgaacggggt gtttgacatg accatgaaga tctggaaggt gctgaggtac   4260
gatgagaccc gcaccaggtg cagaccctgc gagtgtggcg gtaaacatat taggaaccag   4320
cctgtgatgc tggatgtgac cgaggagctg aggcccgatc acttggtgct ggcctgcacc   4380
cgcgctgagt ttggctctag cgatgaagat acagattgag gtactgaaat atgtgggcaa   4440
gccgaatttc gacccgggcg gcctagcgtt taaacgggcc ctctagactc gagcggccgc   4500
cactgtgctg gatgatccga gctcggtacc aagcttaagt ttaaaccgct gatcagcctc   4560
gactgtgcct tctagttgcc agccatctgt tgtttgcccc tcccccgtgc cttccttgac   4620
cctggaaggt gccactccca ctgtcctttc ctaataaaat gaggaaattg catcgcattg   4680
tctgagtagg tgtcattcta ttctgggggg tggggtgggg caggacagca agggggagga   4740
ttgggaagac aatagcaggc atgctgggga tgcggtgggc tctatggctt ctgaggcgga   4800
aagaaccagc agatctgcag atctgaattc atctatgtcg ggtgcggaga aagaggtaat   4860
gaaatggcat cgactcgaag atctgggcgt ggttaagggt gggaaagaat atataaggtg   4920
ggggtcttat gtagttttgt atctgttttg cagcagccgc cgccgccatg agcaccaact   4980
cgtttgatgg aagcattgtg agctcatatt tgacaacgcg catgccccca tgggccgggg   5040
tgcgtcagaa tgtgatgggc tccagcattg atggtcgccc cgtcctgccc gcaaactcta   5100
ctaccttgac ctacgagacc gtgtctggaa cgccgttgga gactgcagcc tccgccgccg   5160
cttcagccgc tgcagccacc gcccgcggga ttgtgactga ctttgctttc ctgagcccgc   5220
ttgcaagcag tgcagcttcc cgttcatccg cccgcgatga caagttgacg gctcttttgg   5280
cacaattgga ttctttgacc cgggaactta atgtcgtttc tcagcagctg ttggatctgc   5340
gccagcaggt ttctgccctg aaggcttcct cccctcccaa tgcggtttaa aacataaata   5400
aaaaaccaga ctctgtttgg atttggatca agcaagtgtc ttgctgtctt tatttagggg   5460
ttttgcgcgc gcggtaggcc cgggaccagc ggtctcggtc gttgagggtc ctgtgtattt   5520
tttccaggac gtggtaaagg tgactctgga tgttcagata catgggcata agcccgtctc   5580
tggggtggag gtagcaccac tgcagagctt catgctgcgg ggtggtgttg tagatgatcc   5640
agtcgtagca ggagcgctgg gcgtggtgcc taaaaatgtc tttcagtagc aagctgattg   5700
ccaggggcag gcccttggtg taagtgttta caaagcggtt aagctgggat gggtgcatac   5760
gtggggatat gagatgcatc ttggactgta tttttaggtt ggctatgttc ccagccatat   5820
ccctccgggg attcatgttg tgcagaacca ccagcacagt gtatccggtg cacttgggaa   5880
```

-continued

```
atttgtcatg tagcttagaa ggaaatgcgt ggaagaactt ggagacgccc ttgtgacctc   5940
caagattttc catgcattcg tccataatga tggcaatggg cccacgggcg gcggcctggg   6000
cgaagatatt tctgggatca ctaacgtcat agttgtgttc caggatgaga tcgtcatagg   6060
ccatttttac aaagcgcggg cggagggtgc cagactgcgg tataatggtt ccatccggcc   6120
caggggcgta gttaccctca cagatttgca tttcccacgc tttgagttca gatgggggga   6180
tcatgtctac ctgcggggcg atgaagaaaa cggtttccgg ggtaggggag atcagctggg   6240
aagaaagcag gttcctgagc agctgcgact taccgcagcc ggtgggcccg taaatcacac   6300
ctattaccgg ctgcaactgg tagttaagag agctgcagct gccgtcatcc ctgagcaggg   6360
gggccacttc gttaagcatg tccctgactc gcatgttttc cctgaccaaa tccgccagaa   6420
ggcgctcgcc gcccagcgat agcagttctt gcaaggaagc aaagtttttc aacggtttga   6480
gaccgtccgc cgtaggcatg cttttgagcg tttgaccaag cagttccagg cggtcccaca   6540
gctcggtcac ctgctctacg gcatctcgat ccagcatatc tcctcgtttc gcgggttggg   6600
gcggctttcg ctgtacggca gtagtcggtg ctcgtccaga cgggccaggg tcatgtcttt   6660
ccacgggcgc agggtcctcg tcagcgtagt ctgggtcacg gtgaaggggt gcgctccggg   6720
ctgcgcgctg gccagggtgc gcttgaggct ggtcctgctg gtgctgaagc gctgccggtc   6780
ttcgccctgc gcgtcggcca ggtagcattt gaccatggtg tcatagtcca gcccctccgc   6840
ggcgtggccc ttggcgcgca gcttgccctt ggaggaggcg ccgcacgagg ggcagtgcag   6900
acttttgagg gcgtagagct tgggcgcgag aaataccgat tccggggagt aggcatccgc   6960
gccgcaggcc ccgcagacgg tctcgcattc cacgagccag gtgagctctg gccgttcggg   7020
gtcaaaaacc aggtttcccc catgcttttt gatgcgtttc ttacctctgg tttccatgag   7080
ccggtgtcca cgctcggtga cgaaaaggct gtccgtgtcc ccgtatacag acttgagagg   7140
cctgtcctcg agcggtgttc cgcggtcctc ctcgtataga aactcggacc actctgagac   7200
aaaggctcgc gtccaggcca gcacgaagga ggctaagtgg gaggggtagc ggtcgttgtc   7260
cactaggggg tccactcgct ccagggtgtg aagacacatg tcgccctctt cggcatcaag   7320
gaaggtgatt ggtttgtagg tgtaggccac gtgaccgggt gttcctgaag gggggctata   7380
aaagggggtg ggggcgcgtt cgtcctcact ctcttccgca tcgctgtctg cgagggccag   7440
ctgttggggt gagtactccc tctgaaaagc gggcatgact tctgcgctaa gattgtcagt   7500
ttccaaaaac gaggaggatt tgatattcac ctggcccgcg gtgatgcctt tgagggtggc   7560
cgcatccatc tggtcagaaa agacaatctt tttgttgtca agcttggtgg caaacgaccc   7620
gtagagggcg ttggacagca acttggcgat ggagcgcagg gtttggtttt tgtcgcgatc   7680
ggcgcgctcc ttggccgcga tgtttagctg cacgtattcg cgcgcaacgc accgccattc   7740
gggaaagacg gtggtgcgct cgtcgggcac caggtgcacg cgccaaccgc ggttgtgcag   7800
ggtgacaagg tcaacgctgg tggctacctc tccgcgtagg cgctcgttgg tccagcagag   7860
gcggccgccc ttgcgcgagc agaatggcgg tagggggtct agctgcgtct cgtccggggg   7920
gtctgcgtcc acggtaaaga ccccgggcag caggcgcgcg tcgaagtagt ctatcttgca   7980
tccttgcaag tctagcgcct gctgccatgc gcgggcggca agcgcgcgct cgtatgggtt   8040
gagtggggga ccccatggca tggggtgggt gagcgcggag gcgtacatgc cgcaaatgtc   8100
gtaaacgtag aggggctctc tgagtattcc aagatatgta gggtagcatc ttccaccgcg   8160
gatgctggcg cgcacgtaat cgtatagttc gtgcgaggga gcgaggaggt cgggaccgag   8220
gttgctacgg gcgggctgct ctgctcggaa gactatctgc ctgaagatgg catgtgagtt   8280
```

-continued

```
ggatgatatg gttggacgct ggaagacgtt gaagctggcg tctgtgagac ctaccgcgtc   8340
acgcacgaag gaggcgtagg agtcgcgcag cttgttgacc agctcggcgg tgacctgcac   8400
gtctagggcg cagtagtcca gggtttcctt gatgatgtca tacttatcct gtcccttttt   8460
tttccacagc tcgcggttga ggacaaactc ttcgcggtct ttccagtact cttggatcgg   8520
aaacccgtcg gcctccgaac ggtaagagcc tagcatgtag aactggttga cggcctggta   8580
ggcgcagcat cccttttcta cgggtagcgc gtatgcctgc gcggccttcc ggagcgaggt   8640
gtgggtgagc gcaaaggtgt ccctgaccat gactttgagg tactggtatt tgaagtcagt   8700
gtcgtcgcat ccgccctgct cccagagcaa aaagtccgtg cgctttttgg aacgcggatt   8760
tggcagggcg aaggtgacat cgttgaagag tatctttccc gcgcgaggca taaagttgcg   8820
tgtgatgcgg aagggtcccg gcacctcgga acggttgtta attacctggg cggcgagcac   8880
gatctcgtca aagccgttga tgttgtggcc cacaatgtaa agttccaaga agcgcgggat   8940
gcccttgatg gaaggcaatt ttttaagttc ctcgtaggtg agctcttcag gggagctgag   9000
cccgtgctct gaaagggccc agtctgcaag atgagggttg gaagcgacga atgagctcca   9060
caggtcacgg gccattagca tttgcaggtg gtcgcgaaag gtcctaaact ggcgacctat   9120
ggccattttt tctggggtga tgcagtagaa ggtaagcggg tcttgttccc agcggtccca   9180
tccaaggttc gcggctaggt ctcgcgcggc agtcactaga ggctcatctc cgccgaactt   9240
catgaccagc atgaagggca cgagctgctt cccaaaggcc cccatccaag tataggtctc   9300
tacatcgtag gtgacaaaga gacgctcggt gcgaggatgc gagccgatcg ggaagaactg   9360
gatctcccgc caccaattgg aggagtggct attgatgtgg tgaaagtaga agtccctgcg   9420
acgggccgaa cactcgtgct ggcttttgta aaaacgtgcg cagtactggc agcggtgcac   9480
gggctgtaca tcctgcacga ggttgacctg acgaccgcgc acaaggaagc agagtgggaa   9540
tttgagcccc tcgcctggcg ggtttggctg gtggtcttct acttcggctg cttgtccttg   9600
accgtctggc tgctcgaggg gagttacggt ggatcggacc accacgccgc gcgagcccaa   9660
agtccagatg tccgcgcgcg gcggtcggag cttgatgaca acatcgcgca gatgggagct   9720
gtccatggtc tggagctccc gcggcgtcag gtcaggcggg agctcctgca ggtttacctc   9780
gcatagacgg gtcagggcgc gggctagatc caggtgatac ctaatttcca ggggctggtt   9840
ggtggcggcg tcgatggctt gcaagaggcc gcatccccgc ggcgcgacta cggtaccgcg   9900
cggcgggcgg tgggccgcgg gggtgtcctt ggatgatgca tctaaaagcg gtgacgcggg   9960
cgagcccccg gaggtagggg gggctccgga cccgccggga gagggggcag gggcacgtcg  10020
gcgccgcgcg cgggcaggag ctggtgctgc gcgcgtaggt tgctggcgaa cgcgacgacg  10080
cggcggttga tctcctgaat ctggcgcctc tgcgtgaaga cgacgggccc ggtgagcttg  10140
aacctgaaag agagttcgac agaatcaatt tcggtgtcgt tgacggcggc ctggcgcaaa  10200
atctcctgca cgtctcctga gttgtcttga taggcgatct cggccatgaa ctgctcgatc  10260
tcttcctcct ggagatctcc gcgtccggct cgctccacgg tggcggcgag gtcgttggaa  10320
atgcgggcca tgagctgcga gaaggcgttg aggcctccct cgttccagac gcggctgtag  10380
accacgcccc cttcggcatc gcgggcgcgc atgaccacct gcgcgagatt gagctccacg  10440
tgccgggcga agacggcgta gtttcgcagg cgctgaaaga ggtagttgag ggtggtggcg  10500
gtgtgttctg ccacgaagaa gtacataacc cagcgtcgca acgtggattc gttgatatcc  10560
cccaaggcct caaggcgctc catggcctcg tagaagtcca cggcgaagtt gaaaaactgg  10620
gagttgcgcg ccgacacggt taactcctcc tccagaagac ggatgagctc ggcgacagtg  10680
```

-continued

```
tcgcgcacct cgcgctcaaa ggctacaggg gcctcttctt cttcttcaat ctcctcttcc  10740
ataagggcct ccccttcttc ttcttctggc ggcggtgggg gaggggggac acggcggcga  10800
cgacggcgca ccgggaggcg gtcgacaaag cgctcgatca tctccccgcg gcgacggcgc  10860
atggtctcgg tgacggcgcg gccgttctcg cgggggcgca gttggaagac gccgcccgtc  10920
atgtcccggt tatgggttgg cgggggctg ccatgcggca gggatacggc gctaacgatg  10980
catctcaaca attgttgtgt aggtactccg ccgccgaggg acctgagcga gtccgcatcg  11040
accggatcgg aaaacctctc gagaaaggcg tctaaccagt cacagtcgca aggtaggctg  11100
agcaccgtgg cgggcggcag cgggcggcgg tcggggttgt ttctggcgga ggtgctgctg  11160
atgatgtaat taaagtaggc ggtcttgaga cggcggatgg tcgacagaag caccatgtcc  11220
ttgggtccgg cctgctgaat gcgcaggcgg tcggccatgc cccaggcttc gttttgacat  11280
cggcgcaggt ctttgtagta gtcttgcatg agcctttcta ccggcacttc ttcttctcct  11340
tcctcttgtc ctgcatctct tgcatctatc gctgcggcgg cggcggagtt tggccgtagg  11400
tggcgccctc ttcctcccat gcgtgtgacc ccgaagcccc tcatcggctg aagcagggct  11460
aggtcggcga caacgcgctc ggctaatatg gcctgctgca cctgcgtgag ggtagactgg  11520
aagtcatcca tgtccacaaa gcggtggtat gcgcccgtgt tgatggtgta agtgcagttg  11580
gccataacgg accagttaac ggtctggtga cccggctgcg agagctcggt gtacctgaga  11640
cgcgagtaag ccctcgagtc aaatacgtag tcgttgcaag tccgcaccag gtactggtat  11700
cccaccaaaa agtgcggcgg cggctggcgg tagaggggcc agcgtagggt ggccggggct  11760
ccgggggcga gatcttccaa cataaggcga tgatatccgt agatgtacct ggacatccag  11820
gtgatgccgg cggcggtggt ggaggcgcgc ggaaagtcgc ggacgcggtt ccagatgttg  11880
cgcagcggca aaaagtgctc catggtcggg acgctctggc cggtcaggcg cgcgcaatcg  11940
ttgacgctct agcgtgcaaa aggagagcct gtaagcgggc actcttccgt ggtctggtgg  12000
ataaattcgc aagggtatca tggcggacga ccggggttcg agccccgtat ccggccgtcc  12060
gccgtgatcc atgcggttac cgcccgcgtg tcgaacccag gtgtgcgacg tcagacaacg  12120
ggggagtgct ccttttggct tccttccagg cgcggcggct gctgcgctag ctttttggc  12180
cactggccgc gcgcagcgta agcggttagg ctggaaagcg aaagcattaa gtggctcgct  12240
ccctgtagcc ggagggttat ttccaaggg ttgagtcgcg ggacccccgg ttcgagtctc  12300
ggaccggccg gactgcggcg aacgggggtt tgcctccccg tcatgcaaga ccccgcttgc  12360
aaattcctcc ggaaacaggg acgagcccct tttttgcttt tcccagatgc atccggtgct  12420
gcggcagatg cgccccctc ctcagcagcg gcaagagcaa gagcagcggc agacatgcag  12480
ggcaccctcc cctcctccta ccgcgtcagg aggggcgaca tccgcggttg acgcggcagc  12540
agatggtgat tacgaacccc cgcggcgccg ggcccggcac tacctggact tggaggaggg  12600
cgagggcctg gcgcggctag gagcgccctc tcctgagcgg cacccaaggg tgcagctgaa  12660
gcgtgatacg cgtgaggcgt acgtgccgcg gcagaacctg tttcgcgacc gcgagggaga  12720
ggagcccgag gagatgcggg atcgaaagtt ccacgcaggg cgcgagctgc ggcatggcct  12780
gaatcgcgag cggttgctgc gcgaggagga ctttgagccc gacgcgcgaa ccgggattag  12840
tcccgcgcgc gcacacgtgg cggccgccga cctggtaacc gcatacgagc agacggtgaa  12900
ccaggagatt aactttcaaa aaagctttaa caaccacgtg cgtacgcttg tggcgcgcga  12960
ggaggtggct ataggactga tgcatctgtg ggactttgta agcgcgctgg agcaaaaccc  13020
aaatagcaag ccgctcatgg cgcagctgtt ccttatagtg cagcacagca gggacaacga  13080
```

```
ggcattcagg gatgcgctgc taaacatagt agagcccgag ggccgctggc tgctcgattt  13140
gataaacatc ctgcagagca tagtggtgca ggagcgcagc ttgagcctgg ctgacaaggt  13200
ggccgccatc aactattcca tgcttagcct gggcaagttt tacgcccgca agatatacca  13260
taccccttac gttcccatag acaaggaggt aaagatcgag gggttctaca tgcgcatggc  13320
gctgaaggtg cttaccttga gcgacgacct gggcgtttat cgcaacgagc gcatccacaa  13380
ggccgtgagc gtgagccggc ggcgcgagct cagcgaccgc gagctgatgc acagcctgca  13440
aagggccctg gctggcacgg gcagcggcga tagagaggcc gagtcctact ttgacgcggg  13500
cgctgacctg cgctgggccc caagccgacg cgccctggag gcagctgggg ccggacctgg  13560
gctggcggtg gcacccgcgc gcgctggcaa cgtcggcggc gtggaggaat atgacgagga  13620
cgatgagtac gagccagagg acggcgagta ctaagcggtg atgtttctga tcagatgatg  13680
caagacgcaa cggacccggc ggtgcgggcg gcgctgcaga gccagccgtc cggccttaac  13740
tccacggacg actggcgcca ggtcatggac cgcatcatgt cgctgactgc gcgcaatcct  13800
gacgcgttcc ggcagcagcc gcaggccaac cggctctccg caattctgga agcggtggtc  13860
ccggcgcgcg caaaccccac gcacgagaag gtgctggcga tcgtaaacgc gctggccgaa  13920
aacagggcca tccggcccga cgaggccggc ctggtctacg acgcgctgct tcagcgcgtg  13980
gctcgttaca acagcggcaa cgtgcagacc aacctggacc ggctggtggg ggatgtgcgc  14040
gaggccgtgg cgcagcgtga gcgcgcgcag cagcagggca acctgggctc catggttgca  14100
ctaaacgcct tcctgagtac acagcccgcc aacgtgccgc ggggacagga ggactacacc  14160
aactttgtga gcgcactgcg gctaatggtg actgagacac cgcaaagtga ggtgtaccag  14220
tctgggccag actatttttt ccagaccagt agacaaggcc tgcagaccgt aaacctgagc  14280
caggctttca aaaacttgca ggggctgtgg ggggtgcggg ctcccacagg cgaccgcgcg  14340
accgtgtcta gcttgctgac gcccaactcg cgcctgttgc tgctgctaat agcgcccttc  14400
acggacagtg gcagcgtgtc ccgggacaca tacctaggtc acttgctgac actgtaccgc  14460
gaggccatag gtcaggcgca tgtggacgag catactttcc aggagattac aagtgtcagc  14520
cgcgcgctgg ggcaggagga cacgggcagc ctggaggcaa ccctaaacta cctgctgacc  14580
aaccggcggc agaagatccc ctcgttgcac agtttaaaca gcgaggagga gcgcattttg  14640
cgctacgtgc agcagagcgt gagccttaac ctgatgcgcg acggggtaac gcccagcgtg  14700
gcgctggaca tgaccgcgcg caacatggaa ccgggcatgt atgcctcaaa ccggccgttt  14760
atcaaccgcc taatggacta cttgcatcgc gcggccgccg tgaaccccga gtatttcacc  14820
aatgccatct tgaacccgca ctggctaccg ccccctggtt tctacaccgg gggattcgag  14880
gtgcccgagg gtaacgatgg attcctctgg gacgacatag acgacagcgt gttttccccg  14940
caaccgcaga ccctgctaga gttgcaacag cgcgagcagg cagaggcggc gctgcgaaag  15000
gaaagcttcc gcaggccaag cagcttgtcc gatctaggcg ctgcggcccc gcggtcagat  15060
gctagtagcc catttccaag cttgataggg tctcttacca gcactcgcac cacccgcccg  15120
cgcctgctgg gcgaggagga gtacctaaac aactcgctgc tgcagccgca gcgcgaaaaa  15180
aacctgcctc cggcatttcc caacaacggg atagagagcc tagtggacaa gatgagtaga  15240
tggaagacgt acgcgcagga gcacagggac gtgccaggcc cgcgcccgcc cacccgtcgt  15300
caaaggcacg accgtcagcg gggtctggtg tgggaggacg atgactcggc agacgacagc  15360
agcgtcctgg atttgggagg gagtggcaac ccgtttgcgc accttcgccc caggctgggg  15420
agaatgtttt aaaaaaaaaa aaagcatgat gcaaaataaa aaactcacca aggccatggc  15480
```

```
accgagcgtt ggttttcttg tattcccctt agtatgcggc gcgcggcgat gtatgaggaa  15540
ggtcctcctc cctcctacga gagtgtggtg agcgcggcgc cagtggcggc ggcgctgggt  15600
tctcccttcg atgctcccct ggacccgccg tttgtgcctc cgcggtacct gcggcctacc  15660
ggggggagaa acagcatccg ttactctgag ttggcacccc tattcgacac cacccgtgtg  15720
tacctggtgg acaacaagtc aacggatgtg gcatccctga actaccagaa cgaccacagc  15780
aactttctga ccacggtcat tcaaaacaat gactacagcc cgggggaggc aagcacacag  15840
accatcaatc ttgacgaccg gtcgcactgg ggcggcgacc tgaaaaccat cctgcatacc  15900
aacatgccaa atgtgaacga gttcatgttt accaataagt ttaaggcgcg ggtgatggtg  15960
tcgcgcttgc ctactaagga caatcaggtg gagctgaaat acgagtgggt ggagttcacg  16020
ctgcccgagg gcaactactc cgagaccatg accatagacc ttatgaacaa cgcgatcgtg  16080
gagcactact tgaaagtggg cagacagaac ggggttctgg aaagcgacat cggggtaaag  16140
tttgacaccc gcaacttcag actggggttt gaccccgtca ctggtcttgt catgcctggg  16200
gtatatacaa acgaagcctt ccatccagac atcattttgc tgccaggatg cggggtggac  16260
ttcacccaca gccgcctgag caacttgttg ggcatccgca agcggcaacc cttccaggag  16320
ggctttagga tcacctacga tgatctggag ggtggtaaca ttcccgcact gttggatgtg  16380
gacgcctacc aggcgagctt gaaagatgac accgaacagg gcgggggtgg cgcaggcggc  16440
agcaacagca gtggcagcgg cgcggaagag aactccaacg cggcagccgc ggcaatgcag  16500
ccggtggagg acatgaacga tcatgccatt cgcggcgaca cctttgccac acgggctgag  16560
gagaagcgcg ctgaggccga agcagcggcc gaagctgccg cccccgctgc gcaacccgag  16620
gtcgagaagc ctcagaagaa accggtgatc aaacccctga cagaggacag caagaaacgc  16680
agttacaacc taataagcaa tgacagcacc ttcacccagt accgcagctg gtaccttgca  16740
tacaactacg gcgaccctca gaccggaatc cgctcatgga ccctgctttg cactcctgac  16800
gtaacctgcg gctcggagca ggtctactgg tcgttgccag acatgatgca agaccccgtg  16860
accttccgct ccacgcgcca gatcagcaac tttccggtgg tgggcgccga gctgttgccc  16920
gtgcactcca agagcttcta caacgaccag gccgtctact cccaactcat ccgccagttt  16980
acctctctga cccacgtgtt caatcgcttt cccgagaacc agattttggc gcgcccgcca  17040
gcccccacca tcaccaccgt cagtgaaaac gttcctgctc tcacagatca cgggacgcta  17100
ccgctgcgca acagcatcgg aggagtccag cgagtgacca ttactgacgc cagacgccgc  17160
acctgcccct acgtttacaa ggccctgggc atagtctcgc cgcgcgtcct atcgagccgc  17220
actttttgag caagcatgtc catccttata tcgcccagca ataacacagg ctggggcctg  17280
cgcttcccaa gcaagatgtt tggcggggcc aagaagcgct ccgaccaaca cccagtgcgc  17340
gtgcgcgggc actaccgcgc gccctggggc gcgcacaaac gcggccgcac tgggcgcacc  17400
accgtcgatg acgccatcga cgcggtggtg gaggaggcgc gcaactacac gcccacgccg  17460
ccaccagtgt ccacagtgga cgcggccatt cagaccgtgg tgcgcggagc ccggcgctat  17520
gctaaaatga agagacggcg gaggcgcgta gcacgtcgcc accgccgccg acccggcact  17580
gccgcccaac gcgcggcggc ggccctgctt aaccgcgcac gtcgcaccgg ccgacgggcg  17640
gccatgcggg ccgctcgaag gctggccgcg ggtattgtca ctgtgccccc caggtccagg  17700
cgacgagcgg ccgccgcagc agccgcggcc attagtgcta tgactcaggg tcgcaggggc  17760
aacgtgtatt gggtgcgcga ctcggttagc ggcctgcgcg tgcccgtgcg cacccgcccc  17820
ccgcgcaact agattgcaag aaaaaactac ttagactcgt actgttgtat gtatccagcg  17880
```

```
gcggcggcgc gcaacgaagc tatgtccaag cgcaaaatca aagaagagat gctccaggtc  17940
atcgcgccgg agatctatgg ccccccgaag aaggaagagc aggattacaa gccccgaaag  18000
ctaaagcggg tcaaaaagaa aaagaaagat gatgatgatg aacttgacga cgaggtggaa  18060
ctgctgcacg ctaccgcgcc caggcgacgg gtacagtgga aaggtcgacg cgtaaaacgt  18120
gttttgcgac ccggcaccac cgtagtcttt acgcccggtg agcgctccac ccgcacctac  18180
aagcgcgtgt atgatgaggt gtacggcgac gaggacctgc ttgagcaggc caacgagcgc  18240
ctcggggagt ttgcctacgg aaagcggcat aaggacatgc tggcgttgcc gctggacgag  18300
ggcaacccaa cacctagcct aaagcccgta acactgcagc aggtgctgcc cgcgcttgca  18360
ccgtccgaag aaaagcgcgg cctaaagcgc gagtctggtg acttggcacc caccgtgcag  18420
ctgatggtac ccaagcgcca gcgactggaa gatgtcttgg aaaaaatgac cgtggaacct  18480
gggctggagc ccgaggtccg cgtgcggcca atcaagcagg tggcgccggg actgggcgtg  18540
cagaccgtgg acgttcagat acccactacc agtagcacca gtattgccac cgccacagag  18600
ggcatggaga cacaaacgtc cccggttgcc tcagcggtgg cggatgccgc ggtgcaggcg  18660
gtcgctgcgg ccgcgtccaa gacctctacg gaggtgcaaa cggacccgtg gatgtttcgc  18720
gtttcagccc cccggcgccc gcgccgttcg aggaagtacg gcgccgccag cgcgctactg  18780
cccgaatatg ccctacatcc ttccattgcg cctacccccg gctatcgtgg ctacacctac  18840
cgccccagaa gacgagcaac tacccgacgc cgaaccacca ctggaacccg ccgccgccgt  18900
cgccgtcgcc agcccgtgct ggccccgatt tccgtgcgca gggtggctcg cgaaggaggc  18960
aggaccctgg tgctgccaac agcgcgctac caccccagca tcgtttaaaa gccggtcttt  19020
gtggttcttg cagatatggc cctcacctgc cgcctccgtt tcccggtgcc gggattccga  19080
ggaagaatgc accgtaggag gggcatggcc ggccacggcc tgacgggcgg catgcgtcgt  19140
gcgcaccacc ggcggcggcg cgcgtcgcac cgtcgcatgc gcggcggtat cctgcccctc  19200
cttattccac tgatcgccgc ggcgattggc gccgtgcccg gaattgcatc cgtggccttg  19260
caggcgcaga gacactgatt aaaaacaagt tgcatgtgga aaaatcaaaa taaaaagtct  19320
ggactctcac gctcgcttgg tcctgtaact attttgtaga atggaagaca tcaactttgc  19380
gtctctggcc ccgcgacacg gctcgcgccc gttcatggga aactggcaag atatcggcac  19440
cagcaatatg agcggtggcg ccttcagctg gggctcgctg tggagcggca ttaaaaattt  19500
cggttccacc gttaagaact atggcagcaa ggcctggaac agcagcacag gccagatgct  19560
gagggataag ttgaaagagc aaaatttcca acaaaaggtg gtagatggcc tggcctctgg  19620
cattagcggg gtggtggacc tggccaacca ggcagtgcaa aataagatta acagtaagct  19680
tgatccccgc cctcccgtag aggagcctcc accggccgtg gagacagtgt ctccagaggg  19740
gcgtggcgaa aagcgtccgc gccccgacag ggaagaaact ctggtgacgc aaatagacga  19800
gcctccctcg tacgaggagg cactaaagca aggcctgccc accacccgtc ccatcgcgcc  19860
catggctacc ggagtgctgg gccagcacac acccgtaacg ctggacctgc ctcccccgc   19920
cgacacccag cagaaacctg tgctgccagg cccgaccgcc gttgttgtaa cccgtcctag  19980
ccgcgcgtcc ctgcgccgcg ccgccagcgg tccgcgatcg ttgcggcccg tagccagtgg  20040
caactggcaa agcacactga acagcatcgt gggtctgggg gtgcaatccc tgaagcgccg  20100
acgatgcttc tgatagctaa cgtgtcgtat gtgtgtcatg tatgcgtcca tgtcgccgcc  20160
agaggagctg ctgagccgcc gcgcgcccgc tttccaagat ggctacccct tcgatgatgc  20220
cgcagtggtc ttacatgcac atctcgggcc aggacgcctc ggagtacctg agccccgggc  20280
```

```
tggtgcagtt tgcccgcgcc accgagacgt acttcagcct gaataacaag tttagaaacc  20340
ccacggtggc gcctacgcac gacgtgacca cagaccggtc ccagcgtttg acgctgcggt  20400
tcatccctgt ggaccgtgag gatactgcgt actcgtacaa ggcgcggttc accctagctg  20460
tgggtgataa ccgtgtgctg gacatggctt ccacgtactt tgacatccgc ggcgtgctgg  20520
acaggggccc tacttttaag ccctactctg gcactgccta caacgccctg gctcccaagg  20580
gtgccccaaa tccttgcgaa tgggatgaag ctgctactgc tcttgaaata aacctagaag  20640
aagaggacga tgacaacgaa gacgaagtag acgagcaagc tgagcagcaa aaaactcacg  20700
tatttgggca ggcgccttat tctggtataa atattacaaa ggagggtatt caaataggtg  20760
tcgaaggtca aacacctaaa tatgccgata aaacatttca acctgaacct caaataggag  20820
aatctcagtg gtacgaaaca gaaattaatc atgcagctgg gagagtccta aaaaagacta  20880
ccccaatgaa accatgttac ggttcatatg caaaacccac aaatgaaaat ggagggcaag  20940
gcattcttgt aaagcaacaa aatggaaagc tagaaagtca agtggaaatg caatttttct  21000
caactactga ggcagccgca ggcaatggtg ataacttgac tcctaaagtg gtattgtaca  21060
gtgaagatgt agatatagaa accccagaca ctcatatttc ttacatgccc actattaagg  21120
aaggtaactc acgagaacta atgggccaac aatctatgcc caacaggcct aattacattg  21180
cttttaggga caattttatt ggtctaatgt attacaacag cacgggtaat atgggtgttc  21240
tggcgggcca agcatcgcag ttgaatgctg ttgtagattt gcaagacaga aacacagagc  21300
tttcatacca gcttttgctt gattccattg gtgatagaac caggtacttt tctatgtgga  21360
atcaggctgt tgacagctat gatccagatg ttagaattat tgaaaatcat ggaactgaag  21420
atgaacttcc aaattactgc tttccactgg gaggtgtgat taatacagag actcttacca  21480
aggtaaaacc taaaacaggt caggaaaatg gatgggaaaa agatgctaca gaattttcag  21540
ataaaaatga aataagagtt ggaaataatt ttgccatgga aatcaatcta aatgccaacc  21600
tgtggagaaa tttcctgtac tccaacatag cgctgtattt gcccgacaag ctaaagtaca  21660
gtccttccaa cgtaaaaatt tctgataacc caaacaccta cgactacatg aacaagcgag  21720
tggtggctcc cgggctagtg gactgctaca ttaaccttgg agcacgctgg tcccttgact  21780
atatggacaa cgtcaaccca tttaaccacc accgcaatgc tggcctgcgc taccgctcaa  21840
tgttgctggg caatggtcgc tatgtgccct tccacatcca ggtgcctcag aagttctttg  21900
ccattaaaaa cctccttctc ctgccgggct catacaccta cgagtggaac ttcaggaagg  21960
atgttaacat ggttctgcag agctccctag gaaatgacct aagggttgac ggagccagca  22020
ttaagtttga tagcatttgc ctttacgcca ccttcttccc catggcccac aacaccgcct  22080
ccacgcttga ggccatgctt agaaacgaca ccaacgacca gtcctttaac gactatctct  22140
ccgccgccaa catgctctac cctatacccg ccaacgctac caacgtgccc atatccatcc  22200
cctcccgcaa ctgggcggct ttccgcggct gggccttcac gcgccttaag actaaggaaa  22260
ccccatcact gggctcgggc tacgaccctt attacaccta ctctggctct ataccctacc  22320
tagatggaac cttttacctc aaccacacct ttaagaaggt ggccattacc tttgactctt  22380
ctgtcagctg gcctggcaat gaccgcctgc ttaccccaa cgagtttgaa attaagcgct  22440
cagttgacgg ggagggttac aacgttgccc agtgtaacat gaccaaagac tggttcctgg  22500
tacaaatgct agctaactat aacattggct accagggctt ctatatccca gagagctaca  22560
aggaccgcat gtactccttc tttagaaact tccagcccat gagccgtcag gtggtggatg  22620
atactaaata caaggactac caacaggtgg gcatcctaca ccaacacaac aactctggat  22680
```

```
ttgttggcta ccttgccccc accatgcgcg aaggacaggc ctaccctgct aacttcccct  22740
atccgcttat aggcaagacc gcagttgaca gcattaccca gaaaaagttt ctttgcgatc  22800
gcaccctttg gcgcatccca ttctccagta actttatgtc catgggcgca ctcacagacc  22860
tgggccaaaa ccttctctac gccaactccg cccacgcgct agacatgact tttgaggtgg  22920
atcccatgga cgagcccacc cttctttatg ttttgtttga agtctttgac gtggtccgtg  22980
tgcaccagcc gcaccgcggc gtcatcgaaa ccgtgtacct gcgcacgccc ttctcggccg  23040
gcaacgccac aacataaaga agcaagcaac atcaacaaca gctgccgcca tgggctccag  23100
tgagcaggaa ctgaaagcca ttgtcaaaga tcttggttgt gggccatatt ttttgggcac  23160
ctatgacaag cgctttccag gctttgtttc tccacacaag ctcgcctgcg ccatagtcaa  23220
tacggccggt cgcgagactg gggcgtaca ctggatggcc tttgcctgga acccgcactc  23280
aaaaacatgc tacctctttg agccctttgg cttttctgac cagcgactca agcaggttta  23340
ccagtttgag tacgagtcac tcctgcgccg tagcgccatt gcttcttccc ccgaccgctg  23400
tataacgctg gaaaagtcca cccaaagcgt acaggggccc aactcggccg cctgtggact  23460
attctgctgc atgtttctcc acgcctttgc caactggccc caaactccca tggatcacaa  23520
ccccaccatg aaccttatta ccggggtacc caactccatg ctcaacagtc cccaggtaca  23580
gcccaccctg cgtcgcaacc aggaacagct ctacagcttc ctggagcgcc actcgcccta  23640
cttccgcagc cacagtgcgc agattaggag cgccacttct tttgtcact tgaaaaacat  23700
gtaaaaataa tgtactagag acactttcaa taaaggcaaa tgcttttatt tgtacactct  23760
cgggtgatta tttacccca cccttgccgt ctgcgccgtt taaaaatcaa aggggttctg  23820
ccgcgcatcg ctatgcgcca ctggcaggga cacgttgcga tactggtgtt tagtgctcca  23880
cttaaactca ggcacaacca tccgcggcag ctcggtgaag ttttcactcc acaggctgcg  23940
caccatcacc aacgcgttta gcaggtcggg cgccgatatc ttgaagtcgc agttggggcc  24000
tccgccctgc gcgcgcgagt tgcgatacac agggttgcag cactggaaca ctatcagcgc  24060
cgggtggtgc acgctggcca gcacgctctt gtcggagatc agatccgcgt ccaggtcctc  24120
cgcgttgctc agggcgaacg gagtcaactt tggtagctgc cttcccaaaa agggcgcgtg  24180
cccaggcttt gagttgcact cgcaccgtag tggcatcaaa aggtgaccgt gcccggtctg  24240
ggcgttagga tacagcgcct gcataaaagc cttgatctgc ttaaaagcca cctgagcctt  24300
tgcgccttca gagaagaaca tgccgcaaga cttgccggaa aactgattgg ccggacaggc  24360
cgcgtcgtgc acgcagcacc ttgcgtcggt gttggagatc tgcaccacat ttcggcccca  24420
ccggttcttc acgatcttgg ccttgctaga ctgctccttc agcgcgcgct gcccgttttc  24480
gctcgtcaca tccatttcaa tcacgtgctc cttatttatc ataatgcttc cgtgtagaca  24540
cttaagctcg ccttcgatct cagcgcagcg gtgcagccac aacgcgcagc ccgtgggctc  24600
gtgatgcttg taggtcacct ctgcaaacga ctgcaggtac gcctgcagga atcgccccat  24660
catcgtcaca aaggtcttgt tgctggtgaa ggtcagctgc aacccgcggt gctcctcgtt  24720
cagccaggtc ttgcatacgg ccgccagagc ttccacttgg tcaggcagta gtttgaagtt  24780
cgcctttaga tcgttatcca cgtggtactt gtccatcagc gcgcgcgcag cctccatgcc  24840
cttctcccac gcagacacga tcggcacact cagcgggttc atcaccgtaa tttcactttc  24900
cgcttcgctg ggctcttcct cttcctcttg cgtccgcata ccacgcgcca ctgggtcgtc  24960
ttcattcagc cgccgcactg tgcgcttacc tcctttgcca tgcttgatta gcaccggtgg  25020
gttgctgaaa cccaccattt gtagcgccac atcttctctt tcttcctcgc tgtccacgat  25080
```

```
tacctctggt gatggcgggc gctcgggctt gggagaaggg cgcttctttt tcttcttggg  25140
cgcaatggcc aaatccgccg ccgaggtcga tggccgcggg ctgggtgtgc gcggcaccag  25200
cgcgtcttgt gatgagtctt cctcgtcctc ggactcgata cgccgcctca tccgcttttt  25260
tgggggcgcc cggggaggcg gcggcgacgg ggacggggac gacacgtcct ccatggttgg  25320
gggacgtcgc gccgcaccgc gtccgcgctc gggggtggtt tcgcgctgct cctcttcccg  25380
actggccatt tccttctcct ataggcagaa aaagatcatg gagtcagtcg agaagaagga  25440
cagcctaacc gccccctctg agttcgccac caccgcctcc accgatgccg ccaacgcgcc  25500
taccaccttc cccgtcgagg cacccccgct tgaggaggag gaagtgatta tcgagcagga  25560
cccaggtttt gtaagcgaag acgacgagga ccgctcagta ccaacagagg ataaaaagca  25620
agaccaggac aacgcagagg caaacgagga acaagtcggg cggggggacg aaaggcatgg  25680
cgactaccta gatgtgggag acgacgtgct gttgaagcat ctgcagcgcc agtgcgccat  25740
tatctgcgac gcgttgcaag agcgcagcga tgtgcccctc gccatagcgg atgtcagcct  25800
tgcctacgaa cgccacctat tctcaccgcg cgtacccccc aaacgccaag aaaacggcac  25860
atgcgagccc aacccgcgcc tcaacttcta ccccgtattt gccgtgccag aggtgcttgc  25920
cacctatcac atctttttcc aaaactgcaa gataccccta tcctgccgtg ccaaccgcag  25980
ccgagcggac aagcagctgg ccttgcggca gggcgctgtc atacctgata tcgcctcgct  26040
caacgaagtg ccaaaaatct ttgagggtct tggacgcgac gagaagcgcg cggcaaacgc  26100
tctgcaacag gaaaacagcg aaaatgaaag tcactctgga gtgttggtgg aactcgaggg  26160
tgacaacgcg cgcctagccg tactaaaacg cagcatcgag gtcacccact ttgcctaccc  26220
ggcacttaac ctacccccca aggtcatgag cacagtcatg agtgagctga tcgtgcgccg  26280
tgcgcagccc ctggagaggg atgcaaattt gcaagaacaa acagaggagg gcctacccgc  26340
agttggcgac gagcagctag cgcgctggct tcaaacgcgc gagcctgccg acttggagga  26400
gcgacgcaaa ctaatgatgg ccgcagtgct cgttaccgtg gagcttgagt gcatgcagcg  26460
gttctttgct gacccggaga tgcagcgcaa gctagaggaa acattgcact acacctttcg  26520
acagggctac gtacgccagg cctgcaagat ctccaacgtg gagctctgca acctggtctc  26580
ctaccttgga attttgcacg aaaaccgcct tgggcaaaac gtgcttcatt ccacgctcaa  26640
gggcgaggcg cgccgcgact acgtccgcga ctgcgtttac ttatttctat gctacacctg  26700
gcagacggcc atgggcgttt ggcagcagtg cttggaggag tgcaacctca aggagctgca  26760
gaaactgcta aagcaaaact tgaaggacct atggacggcc ttcaacgagc gctccgtggc  26820
cgcgcacctg gcggacatca ttttccccga acgcctgctt aaaaccctgc aacagggtct  26880
gccagacttc accagtcaaa gcatgttgca gaactttagg aactttatcc tagagcgctc  26940
aggaatcttg cccgccacct gctgtgcact tcctagcgac tttgtgccca ttaagtaccg  27000
cgaatgccct ccgccgcttt ggggccactg ctaccttctg cagctagcca actaccttgc  27060
ctaccactct gacataatgg aagacgtgag cggtgacggt ctactggagt gtcactgtcg  27120
ctgcaaccta tgcaccccgc accgctccct ggtttgcaat tcgcagctgc ttaacgaaag  27180
tcaaattatc ggtacctttg agctgcaggg tccctcgcct gacgaaaagt ccgcggctcc  27240
ggggttgaaa ctcactccgg ggctgtggac gtcggcttac cttcgcaaat ttgtacctga  27300
ggactaccac gcccacgaga ttaggttcta cgaagaccaa tcccgcccgc ctaatgcgga  27360
gcttaccgcc tgcgtcatta cccagggcca cattcttggc caattgcaag ccatcaacaa  27420
agcccgccaa gagtttctgc tacgaaaggg acgggggggtt tacttggacc cccagtccgg  27480
```

```
cgaggagctc aacccaatcc ccccgccgcc gcagccctat cagcagcagc cgcgggccct  27540

tgcttcccag gatggcaccc aaaaagaagc tgcagctgcc gccgccaccc acggacgagg  27600

aggaatactg ggacagtcag gcagaggagg ttttggacga ggaggaggag gacatgatgg  27660

aagactggga gagcctagac gaggaagctt ccgaggtcga agaggtgtca gacgaaacac  27720

cgtcaccctc ggtcgcattc ccctcgccgg cgccccagaa atcggcaacc ggttccagca  27780

tggctacaac ctccgctcct caggcgccgc cggcactgcc cgttcgccga cccaaccgta  27840

gatgggacac cactggaacc agggccggta agtccaagca gccgccgccg ttagcccaag  27900

agcaacaaca gcgccaaggc taccgctcat ggcgcgggca caagaacgcc atagttgctt  27960

gcttgcaaga ctgtgggggc aacatctcct tcgcccgccg ctttcttctc taccatcacg  28020

gcgtggcctt cccccgtaac atcctgcatt actaccgtca tctctacagc ccatactgca  28080

ccggcggcag cggcagcaac agcagcggcc acacagaagc aaaggcgacc ggatagcaag  28140

actctgacaa agcccaagaa atccacagcg gcggcagcag caggaggagg agcgctgcgt  28200

ctggcgccca acgaacccgt atcgacccgc gagcttagaa acaggatttt tcccactctg  28260

tatgctatat ttcaacagag caggggccaa gaacaagagc tgaaaataaa aaacaggtct  28320

ctgcgatccc tcacccgcag ctgcctgtat cacaaaagcg aagatcagct tcggcgcacg  28380

ctggaagacg cggaggctct cttcagtaaa tactgcgcgc tgactcttaa ggactagttt  28440

cgcgcccttt ctcaaattta agcgcgaaaa ctacgtcatc tccagcggcc acacccggcg  28500

ccagcacctg ttgtcagcgc cattatgagc aaggaaattc ccacgcccta catgtggagt  28560

taccagccac aaatgggact tgcggctgga gctgcccaag actactcaac ccgaataaac  28620

tacatgagcg cgggacccca catgatatcc cgggtcaacg gaatacgcgc ccaccgaaac  28680

cgaattctcc tggaacaggc ggctattacc accacacctc gtaataacct taatccccgt  28740

agttggcccg ctgccctggt gtaccaggaa agtcccgctc ccaccactgt ggtacttccc  28800

agagacgccc aggccgaagt tcagatgact aactcagggg cgcagcttgc gggcggcttt  28860

cgtcacaggg tgcggtcgcc cgggcagggt ataactcacc tgacaatcag agggcgaggt  28920

attcagctca acgacgagtc ggtgagctcc tcgcttggtc tccgtccgga cgggacattt  28980

cagatcggcg gcgccggccg ctcttcattc acgcctcgtc aggcaatcct aactctgcag  29040

acctcgtcct ctgagccgcg ctctggaggc attggaactc tgcaatttat tgaggagttt  29100

gtgccatcgg tctactttaa ccccttctcg ggacctcccg gccactatcc ggatcaattt  29160

attcctaact ttgacgcggt aaaggactcg gcggacggct acgactga              29208
```

```
<210> SEQ ID NO 14
<211> LENGTH: 37289
<212> TYPE: DNA
<213> ORGANISM: Artificial
<220> FEATURE:
<223> OTHER INFORMATION: synthetic DNA

<400> SEQUENCE: 14

catcatcaat aatatacctt attttggatt gaagccaata tgataatgag ggggtggagt     60

ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180

gtgtgcgccg gtgtacacag gaagtgacaa ttttcgcgcg gttttaggcg gatgttgtag    240

taaatttggg cgtaaccgag taagatttgg ccattttcgc gggaaaactg aataagagga    300

agtgaaatct gaataatttt gtgttactca tagcgcgtaa tctctagcat cgtaactata    360
```

```
acggtcctaa ggtagcgaaa gctcagatct cccgatcccc tatggtgcac tctcagtaca    420

atctgctctg atgccgcata gttaagccag tatctgctcc ctgcttgtgt gttggaggtc    480

gctgagtagt gcgcgagcaa aatttaagct acaacaaggc aaggcttgac cgacaattct    540

agcctcgacg cgttggcccc tccctcgggt taccccacag cctaggccga ttcgacctct    600

ctccgctggg gccctcgctg gcgtccctgc accctgggag cgcgagcggc gcgcgggcgg    660

ggaagcgcgg cccagacccc cgggtccgcc cggagcagct gcgctgtcgg ggccaggccg    720

ggctcccagt ggattcgcgg gcacagacgc ccaggaccgc gctccccacg tggcggaggg    780

actggggacc cgggcacccg tcctgcccct tcaccttcca gctccgcctc ctccgcgcgg    840

accccgcccc gtcccgaccc ctcccgggtc cccggcccag ccccctccgg gccctcccag    900

cccctcccct tcctttccgc ggccccgccc tctcctcgcg gcgcgagttt caggcagcgc    960

tgcgtcctgc tgcgcacgtg ggaagccctg gccccggcca cccccgcgat agatctcgag   1020

aattcacgcg aattcggctt acaccgggac tgaaaatgag acatattatc tgccacggag   1080

gtgttattac cgaagaaatg gccgccagtc ttttggacca gctgatcgaa gaggtactgg   1140

ctgataatct tccacctcct agccattttg aaccacctac ccttcacgaa ctgtatgatt   1200

tagacgtgac ggcccccgaa gatcccaacg aggaggcggt ttcgcagatt tttcccgact   1260

ctgtaatgtt ggcggtgcag gaagggattg acttactcac ttttccgccg gcgcccggtt   1320

ctccggagcc gcctcacctt tcccggcagc ccgagcagcc ggagcagaga gccttgggtc   1380

cggtttctat gccaaacctt gtaccggagg tgatcgatct tacctgccac gaggctggct   1440

ttccacccag tgacgacgag gatgaagagg gtgaggagtt tgtgttagat tatgtggagc   1500

accccgggca cggttgcagg tcttgtcatt atcaccggag gaatacgggg gacccagata   1560

ttatgtgttc gctttgctat atgaggacct gtggcatgtt tgtctacagt cctgtgtctg   1620

aacctgagcc tgagcccgag ccagaaccgg agcctgcaag acctacccgc cgtcctaaaa   1680

tggcgcctgc tatcctgaga cgcccgacat cacctgtgtc tagagaatgc aatagtagta   1740

cggatagctg tgactccggt ccttctaaca cacctcctga gatacacccg gtggtcccgc   1800

tgtgccccat taaaccagtt gccgtgagag ttggtgggcg tcgccaggct gtggaatgta   1860

tcgaggactt gcttaacgag cctgggcaac ctttggactt gagctgtaaa cgccccaggc   1920

cataaggtgt aaacctgtga agccgaattc gcgtcgagca tgcatctagg gcggccaatt   1980

ccgcccctct cccccccccc cctctccctc cccccccccc taacgttact ggccgaagcc   2040

gcttggaata aggccggtgt gcgtttgtct atatgttatt ttccaccata ttgccgtctt   2100

ttggcaatgt gagggcccgg aaacctggcc ctgtcttctt gacgagcatt cctaggggtc   2160

tttcccctct cgccaaagga atgcaaggtc tgttgaatgt cgtgaaggaa gcagttcctc   2220

tggaagcttc ttgaagacaa acaacgtctg tagcgaccct ttgcaggcag cggaaccccc   2280

cacctggcga caggtgcctc tgcggccaaa agccacgtgt ataagataca cctgcaaagg   2340

cggcacaacc ccagtgccac gttgtgagtt ggatagttgt ggaaagagtc aaatggctct   2400

cctcaagcgt attcaacaag gggctgaagg atgcccagaa ggtaccccat tgtatgggat   2460

ctgatctggg gcctcggtgc acatgcttta catgtgttta gtcgaggtta aaaaaacgtc   2520

taggcccccc gaaccacggg gacgtggttt tcctttgaaa aacacgatga taagcttgcc   2580

acaacccggg atcctctaga gtcgaaattc ggcttctgac ctcatggagg cttgggagtg   2640

tttggaagat tttctgctg tgcgtaactt gctggaacag agctctaaca gtacctcttg   2700

gttttggagg tttctgtggg gctcatccca ggcaaagtta gtctgcagaa ttaaggagga   2760
```

-continued

```
ttacaagtgg gaatttgaag agcttttgaa atcctgtggt gagctgtttg attctttgaa   2820
tctgggtcac caggcgcttt tccaagagaa ggtcatcaag actttggatt tttccacacc   2880
ggggcgcgct gcggctgctg ttgctttttt gagttttata aaggataaat ggagcgaaga   2940
aacccatctg agcggggggt acctgctgga ttttctggcc atgcatctgt ggagagcggt   3000
tgtgagacac aagaatcgcc tgctactgtt gtcttccgtc cgcccggcga taataccgac   3060
ggaggagcag cagcagcagc aggaggaagc caggcggcgg cggcaggagc agagcccatg   3120
gaacccgaga gccggcctgg accctcggga atgaatgttg tacaggtggc tgaactgtat   3180
ccagaactga gacgcatttt gacaattaca gaggatgggc aggggctaaa gggggtaaag   3240
agggagcggg gggcttgtga ggctacagag gaggctagga atctagcttt tagcttaatg   3300
accagacacc gtcctgagtg tattactttt caacagatca aggataattg cgctaatgag   3360
cttgatctgc tggcgcagaa gtattccata gagcagctga ccacttactg gctgcagcca   3420
ggggatgatt ttgaggaggc tattagggta tatgcaaagg tggcacttag gccagattgc   3480
aagtacaaga tcagcaaact tgtaaatatc aggaattgtt gctacatctc tgggaacggg   3540
gccgaggtgg agatagatac ggaggatagg gtggccttta gatgtagcat gataaatatg   3600
tggccggggg tgcttggcat ggacggggtg gttattatga atgtaaggtt tactggcccc   3660
aattttagcg gtacggtttt cctggccaat accaacctta tcctacacgg tgtaagcttc   3720
tatgggttta acaatacctg tgtggaagcc tggaccgatg taagggttcg gggctgtgcc   3780
ttttactgct gctggaaggg ggtggtgtgt cgccccaaaa gcagggcttc aattaagaaa   3840
tgcctctttg aaaggtgtac cttgggtatc ctgtctgagg gtaactccag ggtgcgccac   3900
aatgtggcct ccgactgtgg ttgcttcatg ctagtgaaaa gcgtggctgt gattaagcat   3960
aacatggtat gtggcaactg cgaggacagg gcctctcaga tgctgacctg ctcggacggc   4020
aactgtcacc tgctgaagac cattcacgta gccagccact ctcgcaaggc ctggccagtg   4080
tttgagcata acatactgac ccgctgttcc ttgcatttgg gtaacaggag gggggtgttc   4140
ctaccttacc aatgcaattt gagtcacact aagatattgc ttgagcccga gagcatgtcc   4200
aaggtgaacc tgaacggggt gtttgacatg accatgaaga tctggaaggt gctgaggtac   4260
gatgagaccc gcaccaggtg cagaccctgc gagtgtggcg gtaaacatat taggaaccag   4320
cctgtgatgc tggatgtgac cgaggagctg aggcccgatc acttggtgct ggcctgcacc   4380
cgcgctgagt ttggctctag cgatgaagat acagattgag gtactgaaat atgtgggcaa   4440
gccgaatttc gacccgggcg gcctagcgtt taaacgggcc ctctagactc gagcggccgc   4500
cactgtgctg gatgatccga gctcggtacc aagcttaagt ttaaaccgct gatcagcctc   4560
gactgtgcct tctagttgcc agccatctgt tgtttgcccc tcccccgtgc cttccttgac   4620
cctggaaggt gccactccca ctgtcctttc ctaataaaat gaggaaattg catcgcattg   4680
tctgagtagg tgtcattcta ttctgggggg tggggtgggg caggacagca agggggagga   4740
ttgggaagac aatagcaggc atgctgggga tgcggtgggc tctatggctt ctgaggcgga   4800
aagaaccagc agatctgcag atctgaattc atctatgtcg ggtgcggaga aagaggtaat   4860
gaaatggcat cgactcgaag atctgggcgt ggttaagggt gggaaagaat atataaggtg   4920
ggggtcttat gtagttttgt atctgttttg cagcagccgc cgccgccatg agcaccaact   4980
cgtttgatgg aagcattgtg agctcatatt tgacaacgcg catgccccca tgggccgggg   5040
tgcgtcagaa tgtgatgggc tccagcattg atggtcgccc cgtcctgccc gcaaactcta   5100
ctaccttgac ctacgagacc gtgtctggaa cgccgttgga gactgcagcc tccgccgccg   5160
```

-continued

```
cttcagccgc tgcagccacc gcccgcggga ttgtgactga ctttgctttc ctgagcccgc   5220
ttgcaagcag tgcagcttcc cgttcatccg cccgcgatga caagttgacg gctcttttgg   5280
cacaattgga ttctttgacc cgggaactta atgtcgtttc tcagcagctg ttggatctgc   5340
gccagcaggt ttctgccctg aaggcttcct cccctcccaa tgcggtttaa aacataaata   5400
aaaaaccaga ctctgtttgg atttggatca agcaagtgtc ttgctgtctt tatttagggg   5460
ttttgcgcgc gcggtaggcc cgggaccagc ggtctcggtc gttgagggtc ctgtgtattt   5520
tttccaggac gtggtaaagg tgactctgga tgttcagata catgggcata agcccgtctc   5580
tggggtggag gtagcaccac tgcagagctt catgctgcgg ggtggtgttg tagatgatcc   5640
agtcgtagca ggagcgctgg gcgtggtgcc taaaaatgtc tttcagtagc aagctgattg   5700
ccaggggcag gcccttggtg taagtgttta caaagcggtt aagctgggat gggtgcatac   5760
gtggggatat gagatgcatc ttggactgta tttttaggtt ggctatgttc ccagccatat   5820
ccctccgggg attcatgttg tgcagaacca ccagcacagt gtatccggtg cacttgggaa   5880
atttgtcatg tagcttagaa ggaaatgcgt ggaagaactt ggagacgccc ttgtgacctc   5940
caagattttc catgcattcg tccataatga tggcaatggg cccacgggcg gcggcctggg   6000
cgaagatatt tctgggatca ctaacgtcat agttgtgttc caggatgaga tcgtcatagg   6060
ccatttttac aaagcgcggg cggagggtgc cagactgcgg tataatggtt ccatccggcc   6120
caggggcgta gttaccctca cagatttgca tttcccacgc tttgagttca gatgggggga   6180
tcatgtctac ctgcggggcg atgaagaaaa cggtttccgg ggtaggggag atcagctggg   6240
aagaaagcag gttcctgagc agctgcgact taccgcagcc ggtgggcccg taaatcacac   6300
ctattaccgg ctgcaactgg tagttaagag agctgcagct gccgtcatcc ctgagcaggg   6360
gggccacttc gttaagcatg tccctgactc gcatgttttc cctgaccaaa tccgccagaa   6420
ggcgctcgcc gcccagcgat agcagttctt gcaaggaagc aaagtttttc aacggtttga   6480
gaccgtccgc cgtaggcatg cttttgagcg tttgaccaag cagttccagg cggtcccaca   6540
gctcggtcac ctgctctacg gcatctcgat ccagcatatc tcctcgtttc gcgggttggg   6600
gcggctttcg ctgtacggca gtagtcggtg ctcgtccaga cgggccaggg tcatgtcttt   6660
ccacgggcgc agggtcctcg tcagcgtagt ctgggtcacg gtgaaggggt gcgctccggg   6720
ctgcgcgctg gccagggtgc gcttgaggct ggtcctgctg gtgctgaagc gctgccggtc   6780
ttcgccctgc gcgtcggcca ggtagcattt gaccatggtg tcatagtcca gcccctccgc   6840
ggcgtggccc ttggcgcgca gcttgccctt ggaggaggcg ccgcacgagg ggcagtgcag   6900
acttttgagg gcgtagagct tgggcgcgag aaataccgat tccggggagt aggcatccgc   6960
gccgcaggcc ccgcagacgg tctcgcattc cacgagccag gtgagctctg gccgttcggg   7020
gtcaaaaacc aggtttcccc catgcttttt gatgcgtttc ttacctctgg tttccatgag   7080
ccggtgtcca cgctcggtga cgaaaaggct gtccgtgtcc ccgtatacag acttgagagg   7140
cctgtcctcg agcggtgttc cgcggtcctc ctcgtataga aactcggacc actctgagac   7200
aaaggctcgc gtccaggcca gcacgaagga ggctaagtgg gaggggtagc ggtcgttgtc   7260
cactaggggg tccactcgct ccagggtgtg aagacacatg tcgccctctt cggcatcaag   7320
gaaggtgatt ggtttgtagg tgtaggccac gtgaccgggt gttcctgaag gggggctata   7380
aaagggggtg ggggcgcgtt cgtcctcact ctcttccgca tcgctgtctg cgagggccag   7440
ctgttggggt gagtactccc tctgaaaagc gggcatgact tctgcgctaa gattgtcagt   7500
ttccaaaaac gaggaggatt tgatattcac ctggcccgcg gtgatgcctt tgagggtggc   7560
```

```
cgcatccatc tggtcagaaa agacaatctt tttgttgtca agcttggtgg caaacgaccc   7620
gtagagggcg ttggacagca acttggcgat ggagcgcagg gtttggtttt tgtcgcgatc   7680
ggcgcgctcc ttggccgcga tgtttagctg cacgtattcg cgcgcaacgc accgccattc   7740
gggaaagacg gtggtgcgct cgtcgggcac caggtgcacg cgccaaccgc ggttgtgcag   7800
ggtgacaagg tcaacgctgg tggctacctc tccgcgtagg cgctcgttgg tccagcagag   7860
gcggccgccc ttgcgcgagc agaatggcgg taggggtct agctgcgtct cgtccggggg   7920
gtctgcgtcc acggtaaaga ccccgggcag caggcgcgcg tcgaagtagt ctatcttgca   7980
tccttgcaag tctagcgcct gctgccatgc gcgggcggca agcgcgcgct cgtatgggtt   8040
gagtgggga ccccatggca tggggtgggt gagcgcggag gcgtacatgc cgcaaatgtc   8100
gtaaacgtag aggggctctc tgagtattcc aagatatgta gggtagcatc ttccaccgcg   8160
gatgctggcg cgcacgtaat cgtatagttc gtgcgaggga gcgaggaggt cgggaccgag   8220
gttgctacgg gcgggctgct ctgctcggaa gactatctgc ctgaagatgg catgtgagtt   8280
ggatgatatg gttggacgct ggaagacgtt gaagctggcg tctgtgagac ctaccgcgtc   8340
acgcacgaag gaggcgtagg agtcgcgcag cttgttgacc agctcggcgg tgacctgcac   8400
gtctagggcg cagtagtcca gggtttcctt gatgatgtca tacttatcct gtcccttttt   8460
tttccacagc tcgcggttga ggacaaactc ttcgcggtct ttccagtact cttggatcgg   8520
aaacccgtcg gcctccgaac ggtaagagcc tagcatgtag aactggttga cggcctggta   8580
ggcgcagcat ccctttcta cgggtagcgc gtatgcctgc gcggccttcc ggagcgaggt   8640
gtgggtgagc gcaaaggtgt ccctgaccat gactttgagg tactggtatt tgaagtcagt   8700
gtcgtcgcat ccgccctgct cccagagcaa aaagtccgtg cgctttttgg aacgcggatt   8760
tggcagggcg aaggtgacat cgttgaagag tatctttccc gcgcgaggca taaagttgcg   8820
tgtgatgcgg aagggtcccg gcacctcgga acggttgtta attacctggg cggcgagcac   8880
gatctcgtca aagccgttga tgttgtggcc cacaatgtaa agttccaaga agcgcgggat   8940
gcccttgatg gaaggcaatt ttttaagttc ctcgtaggtg agctcttcag gggagctgag   9000
cccgtgctct gaaagggccc agtctgcaag atgagggttg gaagcgacga atgagctcca   9060
caggtcacgg gccattagca tttgcaggtg gtcgcgaaag gtcctaaact ggcgacctat   9120
ggccattttt tctggggtga tgcagtagaa ggtaagcggg tcttgttccc agcggtccca   9180
tccaaggttc gcggctaggt ctcgcgcggc agtcactaga ggctcatctc cgccgaactt   9240
catgaccagc atgaagggca cgagctgctt cccaaaggcc cccatccaag tataggtctc   9300
tacatcgtag gtgacaaaga gacgctcggt gcgaggatgc gagccgatcg ggaagaactg   9360
gatctcccgc caccaattgg aggagtggct attgatgtgg tgaaagtaga agtccctgcg   9420
acgggccgaa cactcgtgct ggcttttgta aaaacgtgcg cagtactggc agcggtgcac   9480
gggctgtaca tcctgcacga ggttgacctg acgaccgcgc acaaggaagc agagtgggaa   9540
tttgagcccc tcgcctggcg ggtttggctg gtggtcttct acttcggctg cttgtccttg   9600
accgtctggc tgctcgaggg gagttacggt ggatcggacc accacgccgc gcgagcccaa   9660
agtccagatg tccgcgcgcg gcggtcggag cttgatgaca acatcgcgca gatgggagct   9720
gtccatggtc tggagctccc gcggcgtcag gtcaggcggg agctcctgca ggtttacctc   9780
gcatagacgg gtcagggcgc gggctagatc caggtgatac ctaatttcca ggggctggtt   9840
ggtggcggcg tcgatggctt gcaagaggcc gcatccccgc ggcgcgacta cggtaccgcg   9900
cggcgggcgg tgggccgcgg gggtgtcctt ggatgatgca tctaaaagcg gtgacgcggg   9960
```

```
cgagcccccg gaggtagggg gggctccgga cccgccggga gagggggcag gggcacgtcg  10020
gcgccgcgcg cgggcaggag ctggtgctgc gcgcgtaggt tgctggcgaa cgcgacgacg  10080
cggcggttga tctcctgaat ctggcgcctc tgcgtgaaga cgacgggccc ggtgagcttg  10140
aacctgaaag agagttcgac agaatcaatt tcggtgtcgt tgacggcggc ctggcgcaaa  10200
atctcctgca cgtctcctga gttgtcttga taggcgatct cggccatgaa ctgctcgatc  10260
tcttcctcct ggagatctcc gcgtccggct cgctccacgg tggcggcgag gtcgttggaa  10320
atgcgggcca tgagctgcga gaaggcgttg aggcctccct cgttccagac gcggctgtag  10380
accacgcccc cttcggcatc gcgggcgcgc atgaccacct gcgcgagatt gagctccacg  10440
tgccgggcga agacggcgta gtttcgcagg cgctgaaaga ggtagttgag ggtggtggcg  10500
gtgtgttctg ccacgaagaa gtacataacc cagcgtcgca acgtggattc gttgatatcc  10560
cccaaggcct caaggcgctc catggcctcg tagaagtcca cggcgaagtt gaaaaactgg  10620
gagttgcgcg ccgacacggt taactcctcc tccagaagac ggatgagctc ggcgacagtg  10680
tcgcgcacct cgcgctcaaa ggctacaggg gcctcttctt cttcttcaat ctcctcttcc  10740
ataagggcct ccccttcttc ttcttctggc ggcggtgggg gaggggggac acggcggcga  10800
cgacggcgca ccgggaggcg gtcgacaaag cgctcgatca tctccccgcg gcgacggcgc  10860
atggtctcgg tgacggcgcg gccgttctcg cgggggcgca gttggaagac gccgcccgtc  10920
atgtcccggt tatgggttgg cggggggctg ccatgcggca gggatacggc gctaacgatg  10980
catctcaaca attgttgtgt aggtactccg ccgccgaggg acctgagcga gtccgcatcg  11040
accggatcgg aaaacctctc gagaaaggcg tctaaccagt cacagtcgca aggtaggctg  11100
agcaccgtgg cgggcggcag cgggcggcgg tcggggttgt ttctggcgga ggtgctgctg  11160
atgatgtaat taaagtaggc ggtcttgaga cggcggatgg tcgacagaag caccatgtcc  11220
ttgggtccgg cctgctgaat gcgcaggcgg tcggccatgc cccaggcttc gttttgacat  11280
cggcgcaggt ctttgtagta gtcttgcatg agcctttcta ccggcacttc ttcttctcct  11340
tcctcttgtc ctgcatctct tgcatctatc gctgcggcgg cggcggagtt tggccgtagg  11400
tggcgccctc ttcctcccat gcgtgtgacc ccgaagcccc tcatcggctg aagcagggct  11460
aggtcggcga caacgcgctc ggctaatatg gcctgctgca cctgcgtgag ggtagactgg  11520
aagtcatcca tgtccacaaa gcggtggtat gcgcccgtgt tgatggtgta agtgcagttg  11580
gccataacgg accagttaac ggtctggtga cccggctgcg agagctcggt gtacctgaga  11640
cgcgagtaag ccctcgagtc aaatacgtag tcgttgcaag tccgcaccag gtactggtat  11700
cccaccaaaa agtgcggcgg cggctggcgg tagaggggcc agcgtagggt ggccggggct  11760
ccgggggcga gatcttccaa cataaggcga tgatatccgt agatgtacct ggacatccag  11820
gtgatgccgg cggcggtggt ggaggcgcgc ggaaagtcgc ggacgcggtt ccagatgttg  11880
cgcagcggca aaaagtgctc catggtcggg acgctctggc cggtcaggcg cgcgcaatcg  11940
ttgacgctct agcgtgcaaa aggagagcct gtaagcgggc actcttccgt ggtctggtgg  12000
ataaattcgc aagggtatca tggcggacga ccggggttcg agccccgtat ccggccgtcc  12060
gccgtgatcc atgcggttac cgcccgcgtg tcgaacccag gtgtgcgacg tcagacaacg  12120
ggggagtgct ccttttggct tccttccagg cgcggcggct gctgcgctag cttttttggc  12180
cactggccgc gcgcagcgta agcggttagg ctggaaagcg aaagcattaa gtggctcgct  12240
ccctgtagcc ggagggttat ttccaaggg ttgagtcgcg ggacccccgg ttcgagtctc  12300
ggaccggccg gactgcggcg aacgggggtt tgcctccccg tcatgcaaga ccccgcttgc  12360
```

```
aaattcctcc ggaaacaggg acgagcccct tttttgcttt tcccagatgc atccggtgct  12420
gcggcagatg cgcccccctc ctcagcagcg gcaagagcaa gagcagcggc agacatgcag  12480
ggcaccctcc cctcctccta ccgcgtcagg aggggcgaca tccgcggttg acgcggcagc  12540
agatggtgat tacgaacccc cgcggcgccg ggcccggcac tacctggact tggaggaggg  12600
cgagggcctg gcgcggctag gagcgccctc tcctgagcgg cacccaaggg tgcagctgaa  12660
gcgtgatacg cgtgaggcgt acgtgccgcg gcagaacctg tttcgcgacc gcgagggaga  12720
ggagcccgag gagatgcggg atcgaaagtt ccacgcaggg cgcgagctgc ggcatggcct  12780
gaatcgcgag cggttgctgc gcgaggagga ctttgagccc gacgcgcgaa ccgggattag  12840
tcccgcgcgc gcacacgtgg cggccgccga cctggtaacc gcatacgagc agacggtgaa  12900
ccaggagatt aactttcaaa aaagctttaa caaccacgtg cgtacgcttg tggcgcgcga  12960
ggaggtggct ataggactga tgcatctgtg ggactttgta agcgcgctgg agcaaaaccc  13020
aaatagcaag ccgctcatgg cgcagctgtt ccttatagtg cagcacagca gggacaacga  13080
ggcattcagg gatgcgctgc taaacatagt agagcccgag ggccgctggc tgctcgattt  13140
gataaacatc ctgcagagca tagtggtgca ggagcgcagc ttgagcctgg ctgacaaggt  13200
ggccgccatc aactattcca tgcttagcct gggcaagttt tacgcccgca agatatacca  13260
taccccttac gttcccatag acaaggaggt aaagatcgag gggttctaca tgcgcatggc  13320
gctgaaggtg cttaccttga gcgacgacct gggcgtttat cgcaacgagc gcatccacaa  13380
ggccgtgagc gtgagccggc ggcgcgagct cagcgaccgc gagctgatgc acagcctgca  13440
aagggccctg gctggcacgg gcagcggcga tagagaggcc gagtcctact ttgacgcggg  13500
cgctgacctg cgctgggccc caagccgacg cgccctggag gcagctgggg ccggacctgg  13560
gctggcggtg gcacccgcgc gcgctggcaa cgtcggcggc gtggaggaat atgacgagga  13620
cgatgagtac gagccagagg acggcgagta ctaagcggtg atgtttctga tcagatgatg  13680
caagacgcaa cggacccggc ggtgcgggcg gcgctgcaga gccagccgtc cggccttaac  13740
tccacggacg actggcgcca ggtcatggac cgcatcatgt cgctgactgc gcgcaatcct  13800
gacgcgttcc ggcagcagcc gcaggccaac cggctctccg caattctgga agcggtggtc  13860
ccggcgcgcg caaaccccac gcacgagaag gtgctggcga tcgtaaacgc gctggccgaa  13920
aacagggcca tccggcccga cgaggccggc ctggtctacg acgcgctgct tcagcgcgtg  13980
gctcgttaca acagcggcaa cgtgcagacc aacctggacc ggctggtggg ggatgtgcgc  14040
gaggccgtgg cgcagcgtga gcgcgcgcag cagcagggca acctgggctc catggttgca  14100
ctaaacgcct tcctgagtac acagcccgcc aacgtgccgc ggggacagga ggactacacc  14160
aactttgtga gcgcactgcg gctaatggtg actgagacac cgcaaagtga ggtgtaccag  14220
tctgggccag actatttttt ccagaccagt agacaaggcc tgcagaccgt aaacctgagc  14280
caggctttca aaaacttgca ggggctgtgg ggggtgcggg ctcccacagg cgaccgcgcg  14340
accgtgtcta gcttgctgac gcccaactcg cgcctgttgc tgctgctaat agcgcccttc  14400
acggacagtg gcagcgtgtc ccgggacaca tacctaggtc acttgctgac actgtaccgc  14460
gaggccatag gtcaggcgca tgtggacgag catactttcc aggagattac aagtgtcagc  14520
cgcgcgctgg ggcaggagga cacgggcagc ctggaggcaa ccctaaacta cctgctgacc  14580
aaccggcggc agaagatccc ctcgttgcac agtttaaaca gcgaggagga gcgcattttg  14640
cgctacgtgc agcagagcgt gagccttaac ctgatgcgcg acggggtaac gcccagcgtg  14700
gcgctggaca tgaccgcgcg caacatggaa ccgggcatgt atgcctcaaa ccggccgttt  14760
```

-continued

```
atcaaccgcc taatggacta cttgcatcgc gcggccgccg tgaaccccga gtatttcacc  14820
aatgccatct tgaacccgca ctggctaccg ccccctggtt tctacaccgg gggattcgag  14880
gtgcccgagg gtaacgatgg attcctctgg gacgacatag acgacagcgt gttttccccg  14940
caaccgcaga ccctgctaga gttgcaacag cgcgagcagg cagaggcggc gctgcgaaag  15000
gaaagcttcc gcaggccaag cagcttgtcc gatctaggcg ctgcggcccc gcggtcagat  15060
gctagtagcc catttccaag cttgataggg tctcttacca gcactcgcac cacccgcccg  15120
cgcctgctgg gcgaggagga gtacctaaac aactcgctgc tgcagccgca gcgcgaaaaa  15180
aacctgcctc cggcatttcc caacaacggg atagagagcc tagtggacaa gatgagtaga  15240
tggaagacgt acgcgcagga gcacagggac gtgccaggcc cgcgcccgcc cacccgtcgt  15300
caaaggcacg accgtcagcg gggtctggtg tgggaggacg atgactcggc agacgacagc  15360
agcgtcctgg atttgggagg gagtggcaac ccgtttgcgc accttcgccc caggctgggg  15420
agaatgtttt aaaaaaaaaa aaagcatgat gcaaaataaa aaactcacca aggccatggc  15480
accgagcgtt ggttttcttg tattcccctt agtatgcggc gcgcggcgat gtatgaggaa  15540
ggtcctcctc cctcctacga gagtgtggtg agcgcggcgc cagtggcggc ggcgctgggt  15600
tctcccttcg atgctcccct ggacccgccg tttgtgcctc cgcggtacct gcggcctacc  15660
gggggggagaa acagcatccg ttactctgag ttggcacccc tattcgacac cacccgtgtg  15720
tacctggtgg acaacaagtc aacggatgtg gcatccctga actaccagaa cgaccacagc  15780
aactttctga ccacggtcat tcaaaacaat gactacagcc cgggggaggc aagcacacag  15840
accatcaatc ttgacgaccg gtcgcactgg ggcggcgacc tgaaaaccat cctgcatacc  15900
aacatgccaa atgtgaacga gttcatgttt accaataagt ttaaggcgcg ggtgatggtg  15960
tcgcgcttgc ctactaagga caatcaggtg gagctgaaat acgagtgggt ggagttcacg  16020
ctgcccgagg gcaactactc cgagaccatg accatagacc ttatgaacaa cgcgatcgtg  16080
gagcactact tgaaagtggg cagacagaac ggggttctgg aaagcgacat cggggtaaag  16140
tttgacaccc gcaacttcag actggggttt gaccccgtca ctggtcttgt catgcctggg  16200
gtatatacaa acgaagcctt ccatccagac atcattttgc tgccaggatg cggggtggac  16260
ttcacccaca gccgcctgag caacttgttg ggcatccgca agcggcaacc cttccaggag  16320
ggctttagga tcacctacga tgatctggag ggtggtaaca ttcccgcact gttggatgtg  16380
gacgcctacc aggcgagctt gaaagatgac accgaacagg gcgggggtgg cgcaggcggc  16440
agcaacagca gtggcagcgg cgcggaagag aactccaacg cggcagccgc ggcaatgcag  16500
ccggtggagg acatgaacga tcatgccatt cgcggcgaca cctttgccac acgggctgag  16560
gagaagcgcg ctgaggccga agcagcggcc gaagctgccg cccccgctgc gcaacccgag  16620
gtcgagaagc ctcagaagaa accggtgatc aaacccctga cagaggacag caagaaacgc  16680
agttacaacc taataagcaa tgacagcacc ttcacccagt accgcagctg gtaccttgca  16740
tacaactacg gcgaccctca gaccggaatc cgctcatgga ccctgctttg cactcctgac  16800
gtaacctgcg gctcggagca ggtctactgg tcgttgccag acatgatgca agaccccgtg  16860
accttccgct ccacgcgcca gatcagcaac tttccggtgg tgggcgccga gctgttgccc  16920
gtgcactcca agagcttcta caacgaccag gccgtctact cccaactcat ccgccagttt  16980
acctctctga cccacgtgtt caatcgcttt cccgagaacc agattttggc gcgcccgcca  17040
gcccccacca tcaccaccgt cagtgaaaac gttcctgctc tcacagatca cgggacgcta  17100
ccgctgcgca acagcatcgg aggagtccag cgagtgacca ttactgacgc cagacgccgc  17160
```

-continued

```
acctgcccct acgtttacaa ggccctgggc atagtctcgc cgcgcgtcct atcgagccgc  17220
actttttgag caagcatgtc catccttata tcgcccagca ataacacagg ctggggcctg  17280
cgcttcccaa gcaagatgtt tggcggggcc aagaagcgct ccgaccaaca cccagtgcgc  17340
gtgcgcgggc actaccgcgc gccctggggc gcgcacaaac gcggccgcac tgggcgcacc  17400
accgtcgatg acgccatcga cgcggtggtg gaggaggcgc gcaactacac gcccacgccg  17460
ccaccagtgt ccacagtgga cgcggccatt cagaccgtgg tgcgcggagc ccggcgctat  17520
gctaaaatga agagacggcg gaggcgcgta gcacgtcgcc accgccgccg acccggcact  17580
gccgcccaac gcgcggcggc ggccctgctt aaccgcgcac gtcgcaccgg ccgacgggcg  17640
gccatgcggg ccgctcgaag gctggccgcg ggtattgtca ctgtgccccc caggtccagg  17700
cgacgagcgg ccgccgcagc agccgcggcc attagtgcta tgactcaggg tcgcaggggc  17760
aacgtgtatt gggtgcgcga ctcggttagc ggcctgcgcg tgcccgtgcg cacccgcccc  17820
ccgcgcaact agattgcaag aaaaaactac ttagactcgt actgttgtat gtatccagcg  17880
gcggcggcgc gcaacgaagc tatgtccaag cgcaaaatca aagaagagat gctccaggtc  17940
atcgcgccgg agatctatgg ccccccgaag aaggaagagc aggattacaa gccccgaaag  18000
ctaaagcggg tcaaaaagaa aaagaaagat gatgatgatg aacttgacga cgaggtggaa  18060
ctgctgcacg ctaccgcgcc caggcgacgg gtacagtgga aaggtcgacg cgtaaaacgt  18120
gttttgcgac ccggcaccac cgtagtcttt acgcccggtg agcgctccac ccgcacctac  18180
aagcgcgtgt atgatgaggt gtacggcgac gaggacctgc ttgagcaggc caacgagcgc  18240
ctcggggagt ttgcctacgg aaagcggcat aaggacatgc tggcgttgcc gctggacgag  18300
ggcaacccaa cacctagcct aaagcccgta acactgcagc aggtgctgcc cgcgcttgca  18360
ccgtccgaag aaaagcgcgg cctaaagcgc gagtctggtg acttggcacc caccgtgcag  18420
ctgatggtac ccaagcgcca gcgactggaa gatgtcttgg aaaaaatgac cgtggaacct  18480
gggctggagc ccgaggtccg cgtgcggcca atcaagcagg tggcgccggg actgggcgtg  18540
cagaccgtgg acgttcagat acccactacc agtagcacca gtattgccac cgccacagag  18600
ggcatggaga cacaaacgtc cccggttgcc tcagcggtgg cggatgccgc ggtgcaggcg  18660
gtcgctgcgg ccgcgtccaa gacctctacg gaggtgcaaa cggacccgtg gatgtttcgc  18720
gtttcagccc cccggcgccc gcgccgttcg aggaagtacg gcgccgccag cgcgctactg  18780
cccgaatatg ccctacatcc ttccattgcg cctacccccg gctatcgtgg ctacacctac  18840
cgccccagaa gacgagcaac tacccgacgc cgaaccacca ctggaacccg ccgccgccgt  18900
cgccgtcgcc agcccgtgct ggccccgatt tccgtgcgca gggtggctcg cgaaggaggc  18960
aggaccctgg tgctgccaac agcgcgctac caccccagca tcgtttaaaa gccggtcttt  19020
gtggttcttg cagatatggc cctcacctgc cgcctccgtt tcccggtgcc gggattccga  19080
ggaagaatgc accgtaggag gggcatggcc ggccacggcc tgacgggcgg catgcgtcgt  19140
gcgcaccacc ggcggcggcg cgcgtcgcac cgtcgcatgc gcggcggtat cctgcccctc  19200
cttattccac tgatcgccgc ggcgattggc gccgtgcccg gaattgcatc cgtggccttg  19260
caggcgcaga gacactgatt aaaaacaagt tgcatgtgga aaatcaaaa taaaaagtct  19320
ggactctcac gctcgcttgg tcctgtaact attttgtaga atggaagaca tcaactttgc  19380
gtctctggcc ccgcgacacg gctcgcgccc gttcatggga aactggcaag atatcggcac  19440
cagcaatatg agcggtggcg ccttcagctg gggctcgctg tggagcggca ttaaaaattt  19500
cggttccacc gttaagaact atggcagcaa ggcctggaac agcagcacag gccagatgct  19560
```

```
gagggataag ttgaaagagc aaaatttcca acaaaaggtg gtagatggcc tggcctctgg  19620
cattagcggg gtggtggacc tggccaacca ggcagtgcaa aataagatta acagtaagct  19680
tgatccccgc cctcccgtag aggagcctcc accggccgtg gagacagtgt ctccagaggg  19740
gcgtggcgaa aagcgtccgc gccccgacag ggaagaaact ctggtgacgc aaatagacga  19800
gcctccctcg tacgaggagg cactaaagca aggcctgccc accacccgtc ccatcgcgcc  19860
catggctacc ggagtgctgg gccagcacac acccgtaacg ctggacctgc ctcccccgc   19920
cgacacccag cagaaacctg tgctgccagg cccgaccgcc gttgttgtaa cccgtcctag  19980
ccgcgcgtcc ctgcgccgcg ccgccagcgg tccgcgatcg ttgcggcccg tagccagtgg  20040
caactggcaa agcacactga acagcatcgt gggtctgggg gtgcaatccc tgaagcgccg  20100
acgatgcttc tgatagctaa cgtgtcgtat gtgtgtcatg tatgcgtcca tgtcgccgcc  20160
agaggagctg ctgagccgcc gcgcgcccgc tttccaagat ggctacccct tcgatgatgc  20220
cgcagtggtc ttacatgcac atctcgggcc aggacgcctc ggagtacctg agccccgggc  20280
tggtgcagtt tgcccgcgcc accgagacgt acttcagcct gaataacaag tttagaaacc  20340
ccacggtggc gcctacgcac gacgtgacca cagaccggtc ccagcgtttg acgctgcggt  20400
tcatccctgt ggaccgtgag gatactgcgt actcgtacaa ggcgcggttc accctagctg  20460
tgggtgataa ccgtgtgctg gacatggctt ccacgtactt tgacatccgc ggcgtgctgg  20520
acaggggccc tacttttaag ccctactctg gcactgccta caacgccctg gctcccaagg  20580
gtgccccaaa tccttgcgaa tgggatgaag ctgctactgc tcttgaaata aacctagaag  20640
aagaggacga tgacaacgaa gacgaagtag acgagcaagc tgagcagcaa aaaactcacg  20700
tatttgggca ggcgccttat tctggtataa atattacaaa ggagggtatt caaataggtg  20760
tcgaaggtca aacacctaaa tatgccgata aaacatttca acctgaacct caaataggag  20820
aatctcagtg gtacgaaaca gaaattaatc atgcagctgg gagagtccta aaaaagacta  20880
ccccaatgaa accatgttac ggttcatatg caaaacccac aaatgaaaat ggagggcaag  20940
gcattcttgt aaagcaacaa aatggaaagc tagaaagtca agtggaaatg caatttttct  21000
caactactga ggcagccgca ggcaatggtg ataacttgac tcctaaagtg gtattgtaca  21060
gtgaagatgt agatatagaa accccagaca ctcatatttc ttacatgccc actattaagg  21120
aaggtaactc acgagaacta atgggccaac aatctatgcc caacaggcct aattacattg  21180
cttttaggga caattttatt ggtctaatgt attacaacag cacgggtaat atgggtgttc  21240
tggcgggcca agcatcgcag ttgaatgctg ttgtagattt gcaagacaga aacacagagc  21300
tttcatacca gcttttgctt gattccattg gtgatagaac caggtacttt tctatgtgga  21360
atcaggctgt tgacagctat gatccagatg ttagaattat tgaaaatcat ggaactgaag  21420
atgaacttcc aaattactgc tttccactgg gaggtgtgat taatacagag actcttacca  21480
aggtaaaacc taaaacaggt caggaaaatg gatgggaaaa agatgctaca gaattttcag  21540
ataaaaatga aataagagtt ggaaataatt ttgccatgga aatcaatcta aatgccaacc  21600
tgtggagaaa tttcctgtac tccaacatag cgctgtattt gcccgacaag ctaaagtaca  21660
gtccttccaa cgtaaaaatt tctgataacc caaacaccta cgactacatg aacaagcgag  21720
tggtggctcc cgggctagtg gactgctaca ttaaccttgg agcacgctgg tcccttgact  21780
atatggacaa cgtcaaccca tttaaccacc accgcaatgc tggcctgcgc taccgctcaa  21840
tgttgctggg caatggtcgc tatgtgccct tccacatcca ggtgcctcag aagttctttg  21900
ccattaaaaa cctccttctc ctgccgggct catacaccta cgagtggaac ttcaggaagg  21960
```

-continued

```
atgttaacat ggttctgcag agctccctag gaaatgacct aagggttgac ggagccagca  22020
ttaagtttga tagcatttgc ctttacgcca ccttcttccc catggcccac aacaccgcct  22080
ccacgcttga ggccatgctt agaaacgaca ccaacgacca gtcctttaac gactatctct  22140
ccgccgccaa catgctctac cctatacccg ccaacgctac caacgtgccc atatccatcc  22200
cctcccgcaa ctgggcggct ttccgcggct gggccttcac gcgccttaag actaaggaaa  22260
ccccatcact gggctcgggc tacgaccctt attacaccta ctctggctct ataccctacc  22320
tagatggaac cttttacctc aaccacacct ttaagaaggt ggccattacc tttgactctt  22380
ctgtcagctg gcctggcaat gaccgcctgc ttacccccaa cgagtttgaa attaagcgct  22440
cagttgacgg ggagggttac aacgttgccc agtgtaacat gaccaaagac tggttcctgg  22500
tacaaatgct agctaactat aacattggct accagggctt ctatatccca gagagctaca  22560
aggaccgcat gtactccttc tttagaaact tccagcccat gagccgtcag gtggtggatg  22620
atactaaata caaggactac caacaggtgg gcatcctaca ccaacacaac aactctggat  22680
ttgttggcta ccttgccccc accatgcgcg aaggacaggc ctaccctgct aacttcccct  22740
atccgcttat aggcaagacc gcagttgaca gcattaccca gaaaaagttt ctttgcgatc  22800
gcaccctttg gcgcatccca ttctccagta actttatgtc catgggcgca ctcacagacc  22860
tgggccaaaa ccttctctac gccaactccg cccacgcgct agacatgact tttgaggtgg  22920
atcccatgga cgagcccacc cttctttatg ttttgtttga agtctttgac gtggtccgtg  22980
tgcaccagcc gcaccgcggc gtcatcgaaa ccgtgtacct gcgcacgccc ttctcggccg  23040
gcaacgccac aacataaaga agcaagcaac atcaacaaca gctgccgcca tgggctccag  23100
tgagcaggaa ctgaaagcca ttgtcaaaga tcttggttgt gggccatatt ttttgggcac  23160
ctatgacaag cgctttccag gctttgtttc tccacacaag ctcgcctgcg ccatagtcaa  23220
tacggccggt cgcgagactg gggggcgtaca ctggatggcc tttgcctgga acccgcactc  23280
aaaaacatgc tacctctttg agccctttgg cttttctgac cagcgactca agcaggttta  23340
ccagtttgag tacgagtcac tcctgcgccg tagcgccatt gcttcttccc ccgaccgctg  23400
tataacgctg gaaaagtcca cccaaagcgt acaggggccc aactcggccg cctgtggact  23460
attctgctgc atgtttctcc acgcctttgc caactggccc caaactccca tggatcacaa  23520
ccccaccatg aaccttatta ccggggtacc caactccatg ctcaacagtc cccaggtaca  23580
gcccaccctg cgtcgcaacc aggaacagct ctacagcttc ctggagcgcc actcgcccta  23640
cttccgcagc cacagtgcgc agattaggag cgccacttct ttttgtcact tgaaaaacat  23700
gtaaaaataa tgtactagag acactttcaa taaaggcaaa tgcttttatt tgtacactct  23760
cgggtgatta tttaccccca cccttgccgt ctgcgccgtt taaaaatcaa aggggttctg  23820
ccgcgcatcg ctatgcgcca ctggcaggga cacgttgcga tactggtgtt tagtgctcca  23880
cttaaactca ggcacaacca tccgcggcag ctcggtgaag ttttcactcc acaggctgcg  23940
caccatcacc aacgcgttta gcaggtcggg cgccgatatc ttgaagtcgc agttggggcc  24000
tccgccctgc gcgcgcgagt tgcgatacac agggttgcag cactggaaca ctatcagcgc  24060
cgggtggtgc acgctggcca gcacgctctt gtcggagatc agatccgcgt ccaggtcctc  24120
cgcgttgctc agggcgaacg gagtcaactt tggtagctgc cttcccaaaa agggcgcgtg  24180
cccaggcttt gagttgcact cgcaccgtag tggcatcaaa aggtgaccgt gcccggtctg  24240
ggcgttagga tacagcgcct gcataaaagc cttgatctgc ttaaaagcca cctgagcctt  24300
tgcgccttca gagaagaaca tgccgcaaga cttgccggaa aactgattgg ccggacaggc  24360
```

-continued

```
cgcgtcgtgc acgcagcacc ttgcgtcggt gttggagatc tgcaccacat ttcggcccca  24420
ccggttcttc acgatcttgg ccttgctaga ctgctccttc agcgcgcgct gcccgttttc  24480
gctcgtcaca tccatttcaa tcacgtgctc cttatttatc ataatgcttc cgtgtagaca  24540
cttaagctcg ccttcgatct cagcgcagcg gtgcagccac aacgcgcagc ccgtgggctc  24600
gtgatgcttg taggtcacct ctgcaaacga ctgcaggtac gcctgcagga atcgccccat  24660
catcgtcaca aaggtcttgt tgctggtgaa ggtcagctgc aacccgcggt gctcctcgtt  24720
cagccaggtc ttgcatacgg ccgccagagc ttccacttgg tcaggcagta gtttgaagtt  24780
cgcctttaga tcgttatcca cgtggtactt gtccatcagc gcgcgcgcag cctccatgcc  24840
cttctcccac gcagacacga tcggcacact cagcgggttc atcaccgtaa tttcactttc  24900
cgcttcgctg ggctcttcct cttcctcttg cgtccgcata ccacgcgcca ctgggtcgtc  24960
ttcattcagc cgccgcactg tgcgcttacc tcctttgcca tgcttgatta gcaccggtgg  25020
gttgctgaaa cccaccattt gtagcgccac atcttctctt tcttcctcgc tgtccacgat  25080
tacctctggt gatggcgggc gctcgggctt gggagaaggg cgcttctttt tcttcttggg  25140
cgcaatggcc aaatccgccg ccgaggtcga tggccgcggg ctgggtgtgc gcggcaccag  25200
cgcgtcttgt gatgagtctt cctcgtcctc ggactcgata cgccgcctca tccgcttttt  25260
tgggggcgcc cggggaggcg gcggcgacgg ggacggggac gacacgtcct ccatggttgg  25320
gggacgtcgc gccgcaccgc gtccgcgctc gggggtggtt tcgcgctgct cctcttcccg  25380
actggccatt tccttctcct ataggcagaa aaagatcatg gagtcagtcg agaagaagga  25440
cagcctaacc gccccctctg agttcgccac caccgcctcc accgatgccg ccaacgcgcc  25500
taccaccttc cccgtcgagg cacccccgct tgaggaggag gaagtgatta tcgagcagga  25560
cccaggtttt gtaagcgaag acgacgagga ccgctcagta ccaacagagg ataaaaagca  25620
agaccaggac aacgcagagg caaacgagga acaagtcggg cggggggacg aaaggcatgg  25680
cgactaccta gatgtgggag acgacgtgct gttgaagcat ctgcagcgcc agtgcgccat  25740
tatctgcgac gcgttgcaag agcgcagcga tgtgcccctc gccatagcgg atgtcagcct  25800
tgcctacgaa cgccacctat tctcaccgcg cgtacccccc aaacgccaag aaaacggcac  25860
atgcgagccc aacccgcgcc tcaacttcta ccccgtattt gccgtgccag aggtgcttgc  25920
cacctatcac atctttttcc aaaactgcaa gataccccta tcctgccgtg ccaaccgcag  25980
ccgagcggac aagcagctgg ccttgcggca gggcgctgtc atacctgata tcgcctcgct  26040
caacgaagtg ccaaaaatct ttgagggtct tggacgcgac gagaagcgcg cggcaaacgc  26100
tctgcaacag gaaaacagcg aaaatgaaag tcactctgga gtgttggtgg aactcgaggg  26160
tgacaacgcg cgcctagccg tactaaaacg cagcatcgag gtcacccact ttgcctaccc  26220
ggcacttaac ctacccccca aggtcatgag cacagtcatg agtgagctga tcgtgcgccg  26280
tgcgcagccc ctggagaggg atgcaaattt gcaagaacaa acagaggagg gcctacccgc  26340
agttggcgac gagcagctag cgcgctggct tcaaacgcgc gagcctgccg acttggagga  26400
gcgacgcaaa ctaatgatgg ccgcagtgct cgttaccgtg gagcttgagt gcatgcagcg  26460
gttctttgct gacccggaga tgcagcgcaa gctagaggaa acattgcact acacctttcg  26520
acagggctac gtacgccagg cctgcaagat ctccaacgtg gagctctgca acctggtctc  26580
ctaccttgga attttgcacg aaaaccgcct tgggcaaaac gtgcttcatt ccacgctcaa  26640
gggcgaggcg cgccgcgact acgtccgcga ctgcgtttac ttatttctat gctacacctg  26700
gcagacggcc atgggcgttt ggcagcagtg cttggaggag tgcaacctca aggagctgca  26760
```

-continued

```
gaaactgcta aagcaaaact tgaaggacct atggacggcc ttcaacgagc gctccgtggc 26820
cgcgcacctg gcggacatca ttttccccga acgcctgctt aaaaccctgc aacagggtct 26880
gccagacttc accagtcaaa gcatgttgca gaactttagg aactttatcc tagagcgctc 26940
aggaatcttg cccgccacct gctgtgcact tcctagcgac tttgtgccca ttaagtaccg 27000
cgaatgccct ccgccgcttt ggggccactg ctaccttctg cagctagcca actaccttgc 27060
ctaccactct gacataatgg aagacgtgag cggtgacggt ctactggagt gtcactgtcg 27120
ctgcaaccta tgcaccccgc accgctccct ggtttgcaat tcgcagctgc ttaacgaaag 27180
tcaaattatc ggtacctttg agctgcaggg tccctcgcct gacgaaaagt ccgcggctcc 27240
ggggttgaaa ctcactccgg ggctgtggac gtcggcttac cttcgcaaat ttgtacctga 27300
ggactaccac gcccacgaga ttaggttcta cgaagaccaa tcccgcccgc ctaatgcgga 27360
gcttaccgcc tgcgtcatta cccagggcca cattcttggc caattgcaag ccatcaacaa 27420
agcccgccaa gagtttctgc tacgaaaggg acggggggtt tacttggacc cccagtccgg 27480
cgaggagctc aacccaatcc ccccgccgcc gcagccctat cagcagcagc cgcgggccct 27540
tgcttcccag gatggcaccc aaaaagaagc tgcagctgcc gccgccaccc acggacgagg 27600
aggaatactg ggacagtcag gcagaggagg ttttggacga ggaggaggag gacatgatgg 27660
aagactggga gagcctagac gaggaagctt ccgaggtcga agaggtgtca gacgaaacac 27720
cgtcaccctc ggtcgcattc ccctcgccgg cgccccagaa atcggcaacc ggttccagca 27780
tggctacaac ctccgctcct caggcgccgc cggcactgcc cgttcgccga cccaaccgta 27840
gatgggacac cactggaacc agggccggta agtccaagca gccgccgccg ttagcccaag 27900
agcaacaaca gcgccaaggc taccgctcat ggcgcgggca caagaacgcc atagttgctt 27960
gcttgcaaga ctgtgggggc aacatctcct tcgcccgccg ctttcttctc taccatcacg 28020
gcgtggcctt cccccgtaac atcctgcatt actaccgtca tctctacagc ccatactgca 28080
ccggcggcag cggcagcaac agcagcggcc acacagaagc aaaggcgacc ggatagcaag 28140
actctgacaa agcccaagaa atccacagcg gcggcagcag caggaggagg agcgctgcgt 28200
ctggcgccca acgaacccgt atcgacccgc gagcttagaa acaggatttt tcccactctg 28260
tatgctatat ttcaacagag caggggccaa gaacaagagc tgaaaataaa aaacaggtct 28320
ctgcgatccc tcacccgcag ctgcctgtat cacaaaagcg aagatcagct tcggcgcacg 28380
ctggaagacg cggaggctct cttcagtaaa tactgcgcgc tgactcttaa ggactagttt 28440
cgcgcccttt ctcaaattta agcgcgaaaa ctacgtcatc tccagcggcc acacccggcg 28500
ccagcacctg ttgtcagcgc cattatgagc aaggaaattc ccacgcccta catgtggagt 28560
taccagccac aaatgggact tgcggctgga gctgcccaag actactcaac ccgaataaac 28620
tacatgagcg cgggacccca catgatatcc cgggtcaacg gaatacgcgc ccaccgaaac 28680
cgaattctcc tggaacaggc ggctattacc accacacctc gtaataacct taatccccgt 28740
agttggcccg ctgccctggt gtaccaggaa agtcccgctc ccaccactgt ggtacttccc 28800
agagacgccc aggccgaagt tcagatgact aactcagggg cgcagcttgc gggcggcttt 28860
cgtcacaggg tgcggtcgcc cgggcagggt ataactcacc tgacaatcag agggcgaggt 28920
attcagctca acgacgagtc ggtgagctcc tcgcttggtc tccgtccgga cgggacattt 28980
cagatcggcg gcgccggccg ctcttcattc acgcctcgtc aggcaatcct aactctgcag 29040
acctcgtcct ctgagccgcg ctctggaggc attggaactc tgcaatttat tgaggagttt 29100
gtgccatcgg tctactttaa ccccttctcg ggacctcccg gccactatcc ggatcaattt 29160
```

-continued

```
attcctaact ttgacgcggt aaaggactcg gcggacggct acgactgaat gttaagtgga  29220
gaggcagagc aactgcgcct gaaacacctg gtccactgtc gccgccacaa gtgctttgcc  29280
cgcgactccg gtgagttttg ctactttgaa ttgcccgagg atcatatcga gggcccggcg  29340
cacggcgtcc ggcttaccgc ccagggagag cttgcccgta gcctgattcg ggagtttacc  29400
cagcgccccc tgctagttga gcgggacagg ggaccctgtg ttctcactgt gatttgcaac  29460
tgtcctaacc ctggattaca tcaagatctt tgttgccatc tctgtgctga gtataataaa  29520
tacagaaatt aaaatatact ggggctccta tcgccatcct gtaaacgcca ccgtcttcac  29580
ccgcccaagc aaaccaaggc gaaccttacc tggtactttt aacatctctc cctctgtgat  29640
ttacaacagt ttcaacccag acggagtgag tctacgagag aacctctccg agctcagcta  29700
ctccatcaga aaaaacacca ccctccttac ctgccgggaa cgtacgagtg cgtcaccggc  29760
cgctgcacca cacctaccgc ctgaccgtaa accagacttt ttccggacag acctcaataa  29820
ctctgtttac cagaacagga ggtgagctta gaaaaccctt agggtattag gccaaaggcg  29880
cagctactgt ggggtttatg aacaattcaa gcaactctac gggctattct aattcaggtt  29940
tctctagaat cggggttggg gttattctct gtcttgtgat tctctttatt cttatactaa  30000
cgcttctctg cctaaggctc gccgcctgct gtgtgcacat ttgcatttat tgtcagcttt  30060
ttaaacgctg gggtcgccac ccaagatgat taggtacata atcctaggtt tactcaccct  30120
tgcgtcagcc cacggtacca cccaaaaggt ggattttaag gagccagcct gtaatgttac  30180
attcgcagct gaagctaatg agtgcaccac tcttataaaa tgcaccacag aacatgaaaa  30240
gctgcttatt cgccacaaaa acaaaattgg caagtatgct gtttatgcta tttggcagcc  30300
aggtgacact acagagtata atgttacagt tttccagggt aaaagtcata aaacttttat  30360
gtatactttt ccattttatg aaatgtgcga cattaccatg tacatgagca aacagtataa  30420
gttgtggccc ccacaaaatt gtgtggaaaa cactggcact ttctgctgca ctgctatgct  30480
aattacagtg ctcgctttgg tctgtaccct actctatatt aaatacaaaa gcagacgcag  30540
ctttattgag gaaaagaaaa tgccttaatt tactaagtta caaagctaat gtcaccacta  30600
actgctttac tcgctgcttg caaaacaaat tcaaaaagtt agcattataa ttagaatagg  30660
atttaaaccc cccggtcatt tcctgctcaa taccattccc ctgaacaatt gactctatgt  30720
gggatatgct ccagcgctac aaccttgaag tcaggcttcc tggatgtcag catctgactt  30780
tggccagcac ctgtcccgcg gatttgttcc agtccaacta cagcgaccca ccctaacaga  30840
gatgaccaac acaaccaacg cggccgccgc taccggactt acatctacca caaatacacc  30900
ccaagtttct gcctttgtca ataactggga taacttgggc atgtggtggt tctccatagc  30960
gcttatgttt gtatgcctta ttattatgtg gctcatctgc tgcctaaagc gcaaacgcgc  31020
ccgaccaccc atctatagtc ccatcattgt gctacaccca aacaatgatg gaatccatag  31080
attggacgga ctgaaacaca tgttcttttc tcttacagta tgattaaatg agacatgatt  31140
cctcgagttt ttatattact gacccttgtt gcgctttttt gtgcgtgctc cacattggct  31200
gcggtttctc acatcgaagt agactgcatt ccagccttca cagtctattt gctttacgga  31260
tttgtcaccc tcacgctcat ctgcagcctc atcactgtgg tcatcgcctt tatccagtgc  31320
attgactggg tctgtgtgcg ctttgcatat ctcagacacc atccccagta cagggacagg  31380
actatagctg agcttcttag aattctttaa ttatgaaatt tactgtgact tttctgctga  31440
ttatttgcac cctatctgcg ttttgttccc cgacctccaa gcctcaaaga catatatcat  31500
gcagattcac tcgtatatgg aatattccaa gttgctacaa tgaaaaaagc gatctttccg  31560
```

```
aagcctggtt atatgcaatc atctctgtta tggtgttctg cagtaccatc ttagccctag  31620
ctatatatcc ctaccttgac attggctgga acgcaataga tgccatgaac cacccaactt  31680
tccccgcgcc cgctatgctt ccactgcaac aagttgttgc cggcggcttt gtcccagcca  31740
atcagcctcg cccaccttct cccaccccca ctgaaatcag ctactttaat ctaacaggag  31800
gagatgactg acaccctaga tctagaaatg gacggaatta ttacagagca gcgcctgcta  31860
gaaagacgca gggcagcggc cgagcaacag cgcatgaatc aagagctcca agacatggtt  31920
aacttgcacc agtgcaaaag ggtatctttt tgtctcgtaa agcaggccaa agtcacctac  31980
gacagtaata ccaccggaca ccgccttagc tacaagttgc caaccaagcg tcagaaattg  32040
gtggtcatgg tgggagaaaa gcccattacc ataactcagc actcggtaga aaccgaaggc  32100
tgcattcact caccttgtca aggacctgag gatctctgca cccttattaa gaccctgtgc  32160
ggtctcaaag atcttattcc ctttaactaa taaaaaaaaa taataaagca tcacttactt  32220
aaaatcagtt agcaaatttc tgtccagttt attcagcagc acctccttgc cctcctccca  32280
gctctggtat tgcagcttcc tcctggctgc aaactttctc cacaatctaa atggaatgtc  32340
agtttcctcc tgttcctgtc catccgcacc cactatcttc atgttgttgc agatgaagcg  32400
cgcaagaccg tctgaagata ccttcaaccc cgtgtatcca tatgacacgg aaaccggtcc  32460
tccaactgtg ccttttctta ctcctccctt tgtatccccc aatgggtttc aagagagtcc  32520
ccctggggta ctctctttgc gcctatccga acctctagtt acctccaatg gcatgcttgc  32580
gctcaaaatg ggcaacggcc tctctctgga cgaggccggc aaccttacct cccaaaatgt  32640
aaccactgtg agcccacctc tcaaaaaaac caagtcaaac ataaacctgg aaatatctgc  32700
acccctcaca gttacctcag aagccctaac tgtggctgcc gccgcacctc taatggtcgc  32760
gggcaacaca ctcaccatgc aatcacaggc cccgctaacc gtgcacgact ccaaacttag  32820
cattgccacc caaggacccc tcacagtgtc agaaggaaag ctagccctgc aaacatcagg  32880
cccctcacc accaccgata gcagtaccct tactatcact gcctcacccc ctctaactac  32940
tgccactggt agcttgggca ttgacttgaa agagcccatt tatacacaaa atggaaaact  33000
aggactaaag tacggggctc ctttgcatgt aacagacgac ctaaacactt tgaccgtagc  33060
aactggtcca ggtgtgacta ttaataatac ttccttgcaa actaaagtta ctggagcctt  33120
gggttttgat tcacaaggca atatgcaact taatgtagca ggaggactaa ggattgattc  33180
tcaaaacaga cgccttatac ttgatgttag ttatccgttt gatgctcaaa accaactaaa  33240
tctaagacta ggacagggcc ctctttttat aaactcagcc cacaacttgg atattaacta  33300
caacaaaggc ctttacttgt ttacagcttc aaacaattcc aaaaagcttg aggttaacct  33360
aagcactgcc aaggggttga tgtttgacgc tacagccata gccattaatg caggagatgg  33420
gcttgaattt ggttcaccta atgcaccaaa cacaaatccc ctcaaaacaa aaattggcca  33480
tggcctagaa tttgattcaa acaaggctat ggttcctaaa ctaggaactg gccttagttt  33540
tgacagcaca ggtgccatta cagtaggaaa caaaaataat gataagctaa ctttgtggac  33600
cacaccagct ccatctccta actgtagact aaatgcagag aaagatgcta aactcacttt  33660
ggtcttaaca aaatgtggca gtcaaatact tgctacagtt tcagttttgg ctgttaaagg  33720
cagtttggct ccaatatctg gaacagttca aagtgctcat cttattataa gatttgacga  33780
aaatggagtg ctactaaaca attccttcct ggacccagaa tattggaact ttagaaatgg  33840
agatcttact gaaggcacag cctatacaaa cgctgttgga tttatgccta acctatcagc  33900
ttatccaaaa tctcacggta aaactgccaa aagtaacatt gtcagtcaag tttacttaaa  33960
```

```
cggagacaaa actaaacctg taacactaac cattacacta aacggtacac aggaaacagg  34020

agacacaact ccaagtgcat actctatgtc attttcatgg gactggtctg gccacaacta  34080

cattaatgaa atatttgcca catcctctta cactttttca tacattgccc aagaataaag  34140

aatcgtttgt gttatgtttc aacgtgttta tttttcaatt gcagaaaatt tcaagtcatt  34200

tttcattcag tagtatagcc ccaccaccac atagcttata cagatcaccg taccttaatc  34260

aaactcacag aaccctagta ttcaacctgc cacctccctc ccaacacaca gagtacacag  34320

tcctttctcc ccggctggcc ttaaaaagca tcatatcatg ggtaacagac atattcttag  34380

gtgttatatt ccacacggtt tcctgtcgag ccaaacgctc atcagtgata ttaataaact  34440

ccccgggcag ctcacttaag ttcatgtcgc tgtccagctg ctgagccaca ggctgctgtc  34500

caacttgcgg ttgcttaacg ggcggcgaag gagaagtcca cgcctacatg ggggtagagt  34560

cataatcgtg catcaggata gggcggtggt gctgcagcag cgcgcgaata aactgctgcc  34620

gccgccgctc cgtcctgcag gaatacaaca tggcagtggt ctcctcagcg atgattcgca  34680

ccgcccgcag cataaggcgc cttgtcctcc gggcacagca gcgcaccctg atctcactta  34740

aatcagcaca gtaactgcag cacagcacca caatattgtt caaaatccca cagtgcaagg  34800

cgctgtatcc aaagctcatg gcggggacca cagaacccac gtggccatca taccacaagc  34860

gcaggtagat taagtggcga cccctcataa acacgctgga cataaacatt acctcttttg  34920

gcatgttgta attcaccacc tcccggtacc atataaacct ctgattaaac atggcgccat  34980

ccaccaccat cctaaaccag ctggccaaaa cctgcccgcc ggctatacac tgcagggaac  35040

cgggactgga acaatgacag tggagagccc aggactcgta accatggatc atcatgctcg  35100

tcatgatatc aatgttggca caacacaggc acacgtgcat acacttcctc aggattacaa  35160

gctcctcccg cgttagaacc atatcccagg gaacaaccca ttcctgaatc agcgtaaatc  35220

ccacactgca gggaagacct cgcacgtaac tcacgttgtg cattgtcaaa gtgttacatt  35280

cgggcagcag cggatgatcc tccagtatgg tagcgcgggt ttctgtctca aaaggaggta  35340

gacgatccct actgtacgga gtgcgccgag acaaccgaga tcgtgttggt cgtagtgtca  35400

tgccaaatgg aacgccggac gtagtcatat ttcctgaagc aaaaccaggt gcgggcgtga  35460

caaacagatc tgcgtctccg gtctcgccgc ttagatcgct ctgtgtagta gttgtagtat  35520

atccactctc tcaaagcatc caggcgcccc ctggcttcgg gttctatgta aactccttca  35580

tgcgccgctg ccctgataac atccaccacc gcagaataag ccacacccag ccaacctaca  35640

cattcgttct gcgagtcaca cacgggagga gcgggaagag ctggaagaac catgtttttt  35700

tttttattcc aaaagattat ccaaaacctc aaaatgaaga tctattaagt gaacgcgctc  35760

ccctccggtg gcgtggtcaa actctacagc caaagaacag ataatggcat ttgtaagatg  35820

ttgcacaatg gcttccaaaa ggcaaacggc cctcacgtcc aagtggacgt aaaggctaaa  35880

cccttcaggg tgaatctcct ctataaacat tccagcacct tcaaccatgc ccaaataatt  35940

ctcatctcgc caccttctca atatatctct aagcaaatcc cgaatattaa gtccggccat  36000

tgtaaaaatc tgctccagag cgccctccac cttcagcctc aagcagcgaa tcatgattgc  36060

aaaaattcag gttcctcaca gacctgtata agattcaaaa gcggaacatt aacaaaaata  36120

ccgcgatccc gtaggtccct tcgcagggcc agctgaacat aatcgtgcag gtctgcacgg  36180

accagcgcgg ccacttcccc gccaggaacc atgacaaaag aacccacact gattatgaca  36240

cgcatactcg gagctatgct aaccagcgta gccccgatgt aagcttgttg catgggcggc  36300

gatataaaat gcaaggtgct gctcaaaaaa tcaggcaaag cctcgcgcaa aaaagaaagc  36360
```

```
acatcgtagt catgctcatg cagataaagg caggtaagct ccggaaccac cacagaaaaa  36420

gacaccattt ttctctcaaa catgtctgcg ggtttctgca taaacacaaa ataaaataac  36480

aaaaaaacat ttaaacatta gaagcctgtc ttacaacagg aaaaacaacc cttataagca  36540

taagacggac tacggccatg ccggcgtgac cgtaaaaaaa ctggtcaccg tgattaaaaa  36600

gcaccaccga cagctcctcg gtcatgtccg gagtcataat gtaagactcg gtaaacacat  36660

caggttgatt cacatcggtc agtgctaaaa agcgaccgaa atagcccggg ggaatacata  36720

cccgcaggcg tagagacaac attacagccc ccataggagg tataacaaaa ttaataggag  36780

agaaaaacac ataaacacct gaaaaaccct cctgcctagg caaaatagca ccctcccgct  36840

ccagaacaac atacagcgct tccacagcgg cagccataac agtcagcctt accagtaaaa  36900

aagaaaacct attaaaaaaa caccactcga cacggcacca gctcaatcag tcacagtgta  36960

aaaaagggcc aagtgcagag cgagtatata taggactaaa aaatgacgta acggttaaag  37020

tccacaaaaa acacccagaa aaccgcacgc gaacctacgc ccagaaacga aagccaaaaa  37080

acccacaact tcctcaaatc gtcacttccg ttttcccacg ttacgtcact tcccatttta  37140

agaaaactac aattcccaac acatacaagt tactccgccc taaaacctac gtcacccgcc  37200

ccgttcccac gccccgcgcc acgtcacaaa ctccaccccc tcattatcat attggcttca  37260

atccaaaata aggtatatta ttgatgatg                                     37289
```

```
<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15

gagaggtcga atcggcctag                                                  20


<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16

cttcgcaggg ccagctgaac                                                  20


<210> SEQ ID NO 17
<211> LENGTH: 19
<212> TYPE: DNA
<213> ORGANISM: Artificial
<220> FEATURE:
<223> OTHER INFORMATION: primer

<400> SEQUENCE: 17

taacgagcct gggcaacct                                                   19


<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18

gtcggtcaag ccttgccttg                                                  20
```

<210> SEQ ID NO 19
<211> LENGTH: 21
<212> TYPE: DNA
<213> ORGANISM: Artificial
<220> FEATURE:
<223> OTHER INFORMATION: primer

<400> SEQUENCE: 19
ccttataagc ataagacgga c 21

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
cagctcaatc agtcacagtg 20

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
gtcaagaaga cagggccagg 20

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
ggctgtggaa tgtatcgagg 20

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23
taatgttgtc tctacgcctg 20

<210> SEQ ID NO 24
<211> LENGTH: 19
<212> TYPE: DNA
<213> ORGANISM: Artificial
<220> FEATURE:
<223> OTHER INFORMATION: primer

<400> SEQUENCE: 24
aaccgcacgc gaacctacg 19

<210> SEQ ID NO 25
<211> LENGTH: 19
<212> TYPE: DNA
<213> ORGANISM: Artificial
<220> FEATURE:
<223> OTHER INFORMATION: primer

```
<400> SEQUENCE: 25

ggccgaacac tcgtgctgg                                    19


<210> SEQ ID NO 26
<211> LENGTH: 19
<212> TYPE: DNA
<213> ORGANISM: Artificial
<220> FEATURE:
<223> OTHER INFORMATION: primer

<400> SEQUENCE: 26

tctgcgaaac cgcctcctc                                    19


<210> SEQ ID NO 27
<211> LENGTH: 32
<212> TYPE: DNA
<213> ORGANISM: Artificial
<220> FEATURE:
<223> OTHER INFORMATION: spacer sequence

<400> SEQUENCE: 27

atagatctcg agaattcacg cgaattcggc tt                     32


<210> SEQ ID NO 28
<211> LENGTH: 21
<212> TYPE: DNA
<213> ORGANISM: Artificial
<220> FEATURE:
<223> OTHER INFORMATION: spacer sequence

<400> SEQUENCE: 28

aagccgaatt cgcgtcgagc a                                 21


<210> SEQ ID NO 29
<211> LENGTH: 34
<212> TYPE: DNA
<213> ORGANISM: Artificial
<220> FEATURE:
<223> OTHER INFORMATION: spacer sequence

<400> SEQUENCE: 29

caacccggga tcctctagag tcgaaattcg gctt                   34
```